US009655904B2

(12) United States Patent
Howbert et al.

(10) Patent No.: US 9,655,904 B2
(45) Date of Patent: May 23, 2017

(54) SUBSTITUTED BENZOAZEPINES AS TOLL-LIKE RECEPTOR MODULATORS

(71) Applicants: VentiRx Pharmaceuticals, Inc., Seattle, WA (US); Array BioPharma, Inc., Boulder, CO (US)

(72) Inventors: James Jeffry Howbert, Redmond, WA (US); Gregory Dietsch, Snohomish, WA (US); Robert Hershberg, Seattle, WA (US); Laurence E. Burgess, Boulder, CO (US); Joseph P. Lyssikatos, Piedmont, CA (US); Brad Newhouse, Boulder, CO (US); Hong-Woon Yang, Potomac, MD (US)

(73) Assignees: VENTIRX PHARMACEUTICALS, INC., Seattle, WA (US); ARRAY BIOPHARMA, INC., Boulder, CO (US)

( * ) Notice: Subject to any disclaimer, the term of this patent is extended or adjusted under 35 U.S.C. 154(b) by 0 days.

(21) Appl. No.: 14/817,291

(22) Filed: Aug. 4, 2015

(65) Prior Publication Data
US 2016/0129010 A1    May 12, 2016

Related U.S. Application Data

(62) Division of application No. 14/180,939, filed on Feb. 14, 2014, now Pat. No. 9,126,940, which is a division of application No. 12/859,178, filed on Aug. 18, 2010, now Pat. No. 8,691,809.

(60) Provisional application No. 61/235,586, filed on Aug. 20, 2009, provisional application No. 61/234,969, filed on Aug. 18, 2009.

(51) Int. Cl.
| *A01N 43/00* | (2006.01) |
| *A61K 31/55* | (2006.01) |
| *C07D 223/14* | (2006.01) |
| *C07D 401/12* | (2006.01) |
| *C07D 401/14* | (2006.01) |
| *C07D 403/10* | (2006.01) |
| *C07D 223/16* | (2006.01) |
| *C07D 401/04* | (2006.01) |
| *C07D 405/04* | (2006.01) |
| *C07D 405/10* | (2006.01) |

(52) U.S. Cl.
CPC ............ *A61K 31/55* (2013.01); *C07D 223/14* (2013.01); *C07D 223/16* (2013.01); *C07D 401/04* (2013.01); *C07D 401/12* (2013.01); *C07D 401/14* (2013.01); *C07D 403/10* (2013.01); *C07D 405/04* (2013.01); *C07D 405/10* (2013.01)

(58) Field of Classification Search
USPC ....................................................... 514/213
See application file for complete search history.

(56) References Cited

U.S. PATENT DOCUMENTS

| 4,002,610 | A | 1/1977 | Mohrbacher et al. |
| 6,043,238 | A | 3/2000 | Cooper et al. |
| 8,691,809 | B2 | 4/2014 | Howbert et al. |
| 9,126,940 | B2 | 9/2015 | Howbert et al. |
| 2002/0128208 | A1 | 9/2002 | Snyder et al. |
| 2007/0197478 | A1 | 8/2007 | Jones et al. |
| 2008/0008682 | A1 | 1/2008 | Chong et al. |
| 2008/0057074 | A1 | 3/2008 | Takaoka et al. |
| 2008/0234251 | A1 | 9/2008 | Doherty et al. |
| 2008/0306050 | A1 | 12/2008 | Doherty et al. |
| 2010/0216988 | A1 | 8/2010 | Alonso et al. |
| 2011/0118235 | A1 | 5/2011 | Howbert et al. |

FOREIGN PATENT DOCUMENTS

| EP | 0 825 186 A1 | 2/1998 |
| EP | 1 790 637 A1 | 5/2007 |
| EP | 1 849 781 A1 | 10/2007 |
| WO | WO-96/12493 A1 | 5/1996 |
| WO | WO-98/55148 | 12/1998 |
| WO | WO-03/007955 A2 | 1/2003 |
| WO | WO-2004/096134 A2 | 11/2004 |
| WO | WO-2005/009973 A1 | 2/2005 |
| WO | WO-2005/035534 A1 | 4/2005 |
| WO | WO-2007/024612 A2 | 3/2007 |
| WO | WO-2007/040840 A2 | 4/2007 |
| WO | WO-2007/096151 A2 | 8/2007 |
| WO | WO-2007/128460 A1 | 11/2007 |
| WO | WO-2008/024892 A2 | 2/2008 |
| WO | WO-2008/109177 A2 | 9/2008 |
| WO | WO-2008/109180 A2 | 9/2008 |
| WO | WO-2008/109181 A2 | 9/2008 |
| WO | WO-2009/000412 A1 | 12/2008 |

OTHER PUBLICATIONS

Agrawal, et al., "Cutting Edge: Different Toll-Like Receptor Agonists Instruct Dendritic Cells to Induce Distinct the Responses via Differential Modulation of Extracellular Signal-Regulated Kinase-Mitogen-Activated Protein Kinase and c-Fos" J.Immunol., 171:4984-4989 (2003).
Breslin, H.J. et al., "Synthesis and Anti-HIV Activity of 1,3,4,5-Tetrahydro-2H-1,4-benzodiazepin-2-one (TBO) Derivatives. Truncated4,5,6,7-Tetrahydro-5-methylimidazo [4,5,1-jk] [1,4] benzodiazepin-2(1H)-ones (TIBO) Analogues," Bioorganic & Medicinal Chemistry, 7, (1999), pp. 2427-2436.
Czarniecki, M. "Small Molecule Modulators of Toll-like Receptors". J Medicinal Chem. vol. 51, No. 21, Nov. 13, 2008, pp. 6621-6626.

(Continued)

Primary Examiner — Marcos Sznaidman
(74) Attorney, Agent, or Firm — Marshall, Gerstein & Borun LLP

(57) ABSTRACT

Provided are compositions and methods useful for modulation of signaling through the Toll-like receptors TLR7 and/or TLR8. The compositions and methods have use in treating or preventing disease, including cancer, autoimmune disease, infectious disease, inflammatory disorder, graft rejection, and graft-versus-host disease.

8 Claims, No Drawings

(56) References Cited

OTHER PUBLICATIONS

Hemmi, H. et al., "Small anti-viral compounds activate immune cells via the TLR7 MyD88-dependant signaling pathway," Nature Immunology, vol. 3, No. 2, Feb. 2002, pp. 196-200.
Jurk, M. et al., "Human TLR7 or TLR8 independently confer responsiveness to the antiviral compound R-848," Nature Immunology, vol. 3, No. 6, Jun. 2002, p. 499.
Kiechl, et al., "Toll-Like Receptor 4 Polymorphisms and Atherogenesis" N. Engl. J. Med., 347(3):185-192 (2002).
Papageorgiou, C. and Borer, X., "A Non-Peptide Ligand for the Somatostatin Receptor Having a Benzodiazepinone Structure," Bioorganic & Medicinal Chemistry Letters, Vo. 6, No. 3, 1996, pp. 267-272.

SUBSTITUTED BENZOAZEPINES AS TOLL-LIKE RECEPTOR MODULATORS

RELATED APPLICATIONS

This application is a division of U.S. patent application Ser. No. 14/180,939, filed Feb. 14, 2014 (now allowed), which is a division of U.S. patent application Ser. No. 12/859,178, filed Aug. 18, 2010 (now U.S. Pat. No. 8,691, 809), which claims priority to and the benefit of U.S. Provisional Patent Application No. 61/234,969 filed on Aug. 18, 2009 and U.S. Provisional Patent Application No. 61/235,586 filed on Aug. 20, 2009. The contents of each of the aforementioned applications are hereby incorporated by reference in their entireties.

BACKGROUND OF THE INVENTION

Field of the Invention

This invention relates to methods and compositions for modulating immune function. More specifically, this invention relates to compositions and methods for modulating TLR7- and/or TLR8-mediated signaling.

Description of the State of the Art

Stimulation of the immune system, which includes stimulation of either or both innate immunity and adaptive immunity, is a complex phenomenon that can result in either protective or adverse physiologic outcomes for the host. In recent years there has been increased interest in the mechanisms underlying innate immunity, which is believed to initiate and support adaptive immunity. This interest has been fueled in part by the recent discovery of a family of highly conserved pattern recognition receptor proteins known as Toll-like receptors (TLRs) believed to be involved in innate immunity as receptors for pathogen associated molecular patterns (PAMPs). Compositions and methods useful for modulating innate immunity are therefore of great interest, as they may affect therapeutic approaches to conditions involving autoimmunity, inflammation, allergy, asthma, graft rejection, graft versus host disease (GvHD), infection, cancer, and immunodeficiency.

Toll-like receptors (TLRs) are type I transmembrane proteins that allow organisms (including mammals) to detect microbes and initiate an innate immune response (Beutler, B., *Nature* 2004, 430:257-263). They contain homologous cytoplasmic domains and leucine-rich extracellular domains and typically form homodimers that sense extracellular (or internalized) signals and subsequently initiate a signal transduction cascade via adaptor molecules such as MyD88 (myeloid differentiation factor 88). There is such high homology in the cytoplasmic domains of the TLRs that, initially, it was suggested that similar signaling pathways exist for all TLRs (Re, F., Strominger, J. L., *Immunobiology* 2004, 209:191-198). Indeed, all TLRs can activate NF-kB and MAP kinases; however, the cytokine/chemokine release profiles derived from TLR activation appears unique to each TLR. Additionally, the signaling pathway that TLRs stimulate is very similar to the pathway that the cytokine receptor IL-1R induces. This may be due to the homology that these receptors share, i.e., TIR (Toll/IL-1R homology) domains. Once the TIR domain is activated in TLRs and MyD88 is recruited, activation of the IRAK family of serine/threonine kinases results which eventually promotes the degradation of Ik-B and activation of NF-kB (Means T. K., et al. *Life Sci.* 2000, 68:241¬258). While it appears that this cascade is designed to allow extracellular stimuli to promote intracellular events, there is evidence that some TLRs migrate to endosomes where signaling can also be initiated. This process may allow for intimate contact with engulfed microbes and fits with the role that these receptors play in the innate immune response (Underhill, D. M., et al., *Nature* 1999, 401:811-815). This process might also allow host nucleic acids, released by damaged tissues (for example, in inflammatory disease) or apoptosis to trigger a response via endosomal presentation. Among mammals, there are 11 TLRs that coordinate this rapid response. A hypothesis put forward years ago (Janeway, C. A., Jr., *Cold Spring Harb. Syrup. Quant. Biol.* 1989, 54:1-13) that the innate immune response initiates the adaptive immune response through the pattern of TLR activation caused by microbes has now been substantiated. Thus, the pathogen-associated molecular patterns (PAMPs) presented by a diverse group of infectious organisms results in a innate immune response involving certain cytokines, chemokines and growth factors followed by a precise adaptive immune response tailored to the infectious pathogen via antigen presentation resulting in antibody production and cytotoxic T cell generation.

Gram-negative bacterial lipopolysaccharide (LPS) has long been appreciated as an adjuvant and immune-stimulant and as a pharmacological tool for inducing an inflammatory reaction in mammals similar to septic shock. Using a genetic approach, TLR4 was identified as the receptor for LPS. The discovery that LPS is an agonist of TLR4 illustrates the usefulness of TLR modulation for vaccine and human disease therapy (Aderem, A.; Ulevitch, R. J., *Nature* 2000, 406:782-787). It is now appreciated that various TLR agonists can activate B cells, neutrophils, mast cells, eosinophils, endothelial cells and several types of epithelia in addition to regulating proliferation and apoptosis of certain cell types.

To date, TLR7 and TLR8, which are somewhat similar, have been characterized as receptors for single-stranded RNA found in endosomal compartments and thus thought to be important for the immune response to viral challenge. Imiquimod, an approved topical anti-viral/anti-cancer drug, has recently been described as a TLR7 agonist that has demonstrated clinical efficacy in certain skin disorders (Miller R. L., et al., *Int. J. Immunopharm.* 1999, 21:1-14). This small molecule drug has been described as a structural mimetic of ssRNA. TLR8 was first described in 2000 (Du, X., et al., *European Cytokine Network* 2000 (September), 11(3):362-371) and was rapidly ascribed to being involved with the innate immune response to viral infection (Miettinen, M., et al., *Genes and Immunity* 2001 (October), 2(6):349-355).

Recently it was reported that certain imidazoquinoline compounds having antiviral activity are ligands of TLR7 and TLR8 (Hemmi H., et al. (2002) *Nat. Immunol.* 3:196-200; Jurk M., et al. (2002) *Nat. Immunol.* 3:499). Imidazoquinolines are potent synthetic activators of immune cells with antiviral and antitumor properties. Using macrophages from wildtype and MyD88-deficient mice, Hemmi et al. recently reported that two imidazoquinolines, imiquimod and resiquimod (R848), induce tumor necrosis factor (TNF) and interleukin-12 (IL-12) and activate NF-icB only in wildtype cells, consistent with activation through a TLR (Hemmi H., et al. (2002) *Nat. Immunol.* 3:196-200). Macrophages from mice deficient in TLR7 but not other TLRs produced no detectable cytokines in response to these imidazoquinolines. In addition, the imidazoquinolines induced dose-dependent proliferation of splenic B cells and the activation of intracellular signaling cascades in cells from wildtype but not TLR7−/− mice. Luciferase analysis established that expression of human TLR7, but not TLR2 or TLR4, in human embryonic kidney cells results in NF-κB activation in response to resiquimod. The findings of Hemmi et al. thus suggest that these imidazoquinoline compounds are non-natural ligands of TLR7 that can induce signaling through TLR7. Recently it was reported that R848 is also a ligand for human TLR8 (Jurk M., et al. (2002) Nat. Immunol. 3:499).

In view of the great therapeutic potential for compounds that modulate toll-like receptors, and despite the work that has already been done, there is a substantial ongoing need to expand their use and therapeutic benefits.

SUMMARY OF THE INVENTION

The compositions described herein are useful for modulating immune responses in vitro and in vivo. Such compositions will find use in a number of clinical applications, such as in methods for treating or preventing conditions involving unwanted immune activity, including inflammatory and autoimmune disorders.

Specifically, the invention relates to a compound having the formula I:

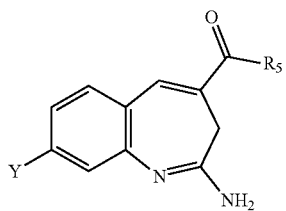

(I)

or a tautomer, enantiomer or salt thereof, wherein:
Y is —(O)$_x$(CH$_2$)$_y$R$^{11}$;
  x is selected from 0 and 1;
  y is selected from 0, 1, 2, and 3;
  R$^{11}$ is selected from aryl, heteroaryl, and saturated or partially saturated heterocycle, wherein when x is 0, said aryl or heteroaryl is substituted with —C(O)NR$^1$R$^2$ or T;
  R$^1$ and R$^2$ are independently selected from hydrogen and alkyl, wherein said alkyl is optionally substituted with —C(O)O(CH$_2$)$_t$R$^{12}$ or R$^1$ and R$^2$ together with the nitrogen atom to which they are attached form a saturated heterocyclic ring;
  t is selected from 0, 1, 2, and 3;
  R$^{12}$ is selected from cycloalkyl and aryl;
  T is selected from heterocycle, —(CHR$^7$)$_z$OR$^9$, —(O)$_u$(CH$_2$)$_s$C(O)R$^8$, —OSO$_2$R$^{13}$, and —CH(OH)CH$_2$OH;
  R$^7$ is selected from H or —OH;
  R$^8$ is selected from —OR$^{10}$ and alkyl;
  R$^9$ is selected from alkyl and H;
  R$^{10}$ is selected from alkyl, —(CH$_2$)R$^{12}$, and hydrogen, wherein said alkyl is optionally substituted with halogen, amine, alkylamine, or dialkylamine;
  R$^{13}$ is selected from —OH, alkyl, CF$_3$, cycloalkyl, heterocycle, aryl, and heteroaryl;
  u is selected from 0 and 1;
  z is selected from 1, 2, and 3;
  s is selected from 1 and 2;
  R$^5$ is selected from —NR$^3$R$^4$ and —OR$^{10}$;
  R$^3$ and R$^4$ are independently selected from H, alkyl, —(O)$_q$(CH$_2$)$_r$P; wherein said alkyl is optionally substituted with one or more —OH;
  q is selected from 0 and 1;
  r is selected from 0, 1, 2, and 3;
  P is selected from aryl, —SO$_2$R$^6$, —C(O)NH$_2$, and heterocycle; and
  R$^6$ is selected from —NH$_2$, —NH(alkyl), —N(alkyl)$_2$, provided that when R$^{11}$ is aryl or heteroaryl, then
  a) x+y≥1;
  or
  b) R$^{11}$ is substituted with T;
  or
  c) R$^5$ is NR$^3$R$^4$ and at least one of R$^3$ or R$^4$ is [(O)$_q$(CH$_2$)$_r$P] and q+r≥1;
  or
  d) at least one of R$^1$ or R$^2$ is alkyl substituted with —C(O)O(CH$_2$)R$^{12}$.

The invention also relates to a compound having the formula II:

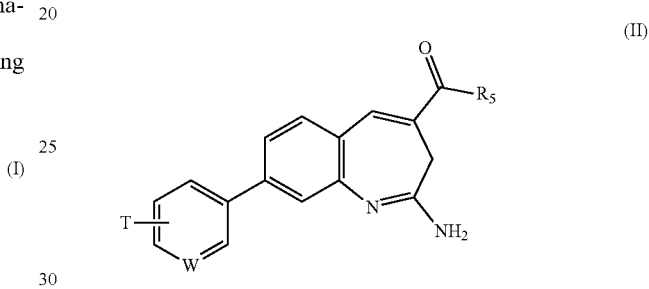

(II)

or a tautomer, enantiomer or salt thereof wherein:
W is selected from N, C-T and CH; and T and R$^5$ are as defined in formula I.

The invention also relates to a compound having the formula III:

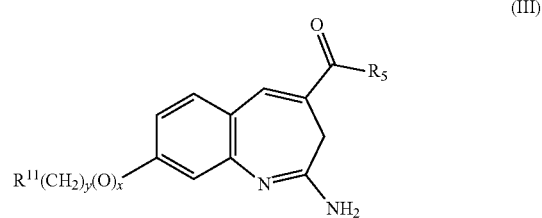

(III)

or a tautomer, enantiomer or salt thereof, wherein x, y, R$^{11}$ and R$^5$ are as defined in formula I;
provided that when R$^{11}$ is aryl or heteroaryl, then x+y≥1.

The invention also relates to a compound having the formula IV:

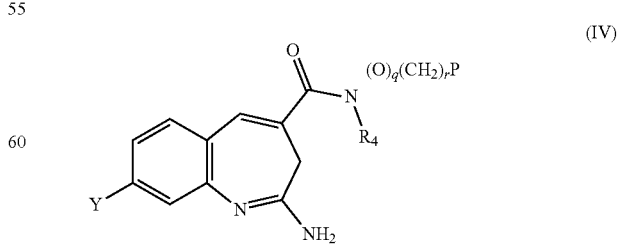

(IV)

or a tautomer, enantiomer or salt thereof, wherein Y, R$^4$, q, r and P are eas defined in formula I, and q+r≥1.

The invention also relates to a compound having the formula V:

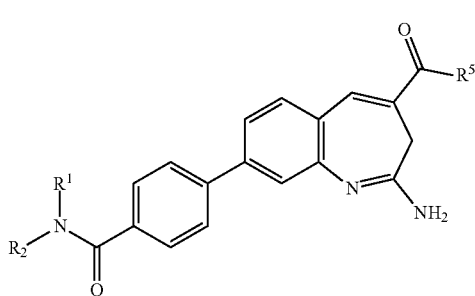

or a tautomer, enantiomer or salt thereof, wherein
$R^1$, $R^2$ and $R^5$ are as defined in formula I; and at least one of $R^1$ or $R^2$ is alkyl substituted with —C(O)O(CH$_2$)R$^{12}$.

The invention also relates to a compound having the formula VI:

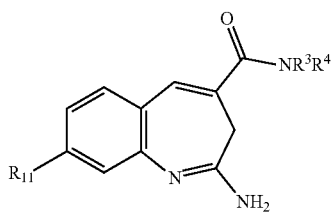

or a tautomer, enantiomer or salt thereof, wherein:
$R^{11}$ is selected from aryl and saturated or partially saturated heterocycle, wherein said aryl is substituted with T;
T is selected from heterocycle, —(O)$_u$(CH$_2$)$_s$C(O)R$^8$, and —CH(OH)CH$_2$OH;
$R^8$ is selected from —OR$^{10}$ and alkyl;
$R^{10}$ is selected from alkyl, —(CH$_2$)R$^{12}$, and hydrogen, wherein said alkyl is optionally substituted with halogen, amine, alkylamine, or dialkylamine;
$R^{12}$ is selected from cycloalkyl and aryl;
u is selected from 0 and 1;
s is selected from 1 and 2; and
$R^3$ and $R^4$ are independently alkyl; wherein said alkyl is optionally substituted with one or more —OH.

The compounds of the invention may be used in combination with other known therapeutic agents. Accordingly, this invention also relates to pharmaceutical compositions comprising a therapeutically effective amount of a compound of the invention or a salt thereof, in combination with a second therapeutic agent.

This invention further provides methods of modulating TLR7- and/or TLR8-mediated signaling, comprising contacting a cell expressing TLR7 and/or TLR8 with an effective amount of a compound of the invention, or a salt thereof. In one aspect, the method inhibits TLR7- and/or TLR8-mediated immunostimulatory signaling.

This invention further provides methods of modulating TLR7- and/or TLR8-mediated immunostimulation in a subject, comprising administering to a patient having or at risk of developing TLR7- and/or TLR8-mediated immunostimulation a compound of the invention, or a salt thereof, in an amount effective to inhibit TLR7- and/or TLR8-mediated immunostimulation in the subject.

This invention further provides methods of modulating TLR7- and/or TLR8-mediated immunostimulation in a subject, comprising administering to a patient having or at risk of developing TLR7- and/or TLR8-mediated immunostimulation a compound of the invention, or a salt thereof, in an amount effective to promote TLR7- and/or TLR8-mediated immunostimulation in the subject.

This invention further provides methods of treating or preventing a disease or condition by modulation of TLR7- and/or TLR8-mediated cellular activities, comprising administering to a warm-blooded animal, such as a mammal, for example a human, having or at risk of developing said disease or condition, a compound of the invention, or a salt thereof.

This invention further provides methods of modulating the immune system of a mammal, comprising administering to a mammal a compound of the invention, or a salt thereof, in an amount effective to modulate said immune system.

Further provided is a compound of the invention, or a salt thereof for use as a medicament in the treatment of the diseases or conditions described herein (e.g., cancer, autoimmune disease, infectious disease, inflammatory disorder, graft rejection, and graft-versus-host disease) in a mammal, for example, a human, suffering from such disease or condition. Also provided is the use of a compound of the invention, a salt thereof, in the preparation of a medicament for the treatment of the diseases and conditions described herein (e.g., cancer, autoimmune disease, infectious disease, inflammatory disorder, graft rejection, and graft-versus-host disease) in a mammal, for example a human, suffering from such disease or condition.

Further provided is a compound of the invention, or a salt thereof for use as a medicament in the prevention of the diseases or conditions described herein (e.g., cancer, autoimmune disease, infectious disease, inflammatory disorder, graft rejection, and graft-versus-host disease) in a mammal, for example, a human, exposed to or predisposed to the disease or condition, but the mammal does not yet experience or display symptoms of such disease or condition. Also provided is the use of a compound of the invention, a salt thereof, in the preparation of a medicament for the treatment of the diseases and conditions described herein (e.g., cancer, autoimmune disease, infectious disease, inflammatory disorder, graft rejection, and graft-versus-host disease) in a mammal, for example a human, suffering from such disease or condition.

The disease or condition is selected from, for example, cancer, autoimmune disease, infectious disease, inflammatory disorder, graft rejection, and graft-versus-host disease.

This invention further provides kits comprising one or more compounds of the invention, or a salt thereof. The kit may further comprise a second compound or formulation comprising a second pharmaceutical agent.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

In certain aspects, the invention provides compositions and methods useful for modulating TLR7- and/or TLR8- mediated signaling. More specifically, one aspect of this invention provides a compound having the formula I:

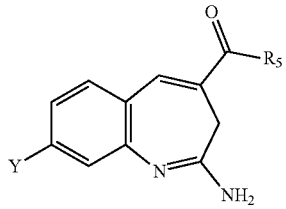

(I)

or a tautomer, enantiomer or salt thereof, wherein:
Y is —(O)$_x$(CH$_2$)$_y$R$^{11}$;
x is selected from 0 and 1;
y is selected from 0, 1, 2, and 3;
R$^{11}$ is selected from aryl, heteroaryl, and saturated or partially saturated heterocycle, wherein when x is 0, said aryl or heteroaryl is substituted with —C(O)NR$^1$R$^2$ or T;
R$^1$ and R$^2$ are independently selected from hydrogen and alkyl, wherein said alkyl is optionally substituted with —C(O)O(CH$_2$)$_t$R$^{12}$ or R$^1$ and R$^2$ together with the nitrogen atom to which they are attached form a saturated heterocyclic ring;
t is selected from 0, 1, 2, and 3;
R$^{12}$ is selected from cycloalkyl and aryl;
T is selected from heterocycle, —(CHR$^7$)$_z$OR$^9$, —(O)$_u$(CH$_2$)$_s$C(O)R$^8$, —OSO$_2$R$^{13}$, and —CH(OH)CH$_2$OH;
R$^7$ is selected from H or —OH;
R$^8$ is selected from —OR$^{10}$ and alkyl;
R$^9$ is selected from alkyl and H;
R$^{10}$ is selected from alkyl, —(CH$_2$)R$^{12}$, and hydrogen, wherein said alkyl is optionally substituted with halogen, amine, alkylamine, or dialkylamine;
R$^{13}$ is selected from —OH, alkyl, CF$_3$, cycloalkyl, heterocycle, aryl, and heteroaryl;
u is selected from 0 and 1;
z is selected from 1, 2, and 3;
s is selected from 1 and 2;
R$^5$ is selected from —NR$^3$R$^4$ and —OR$^{10}$;
R$^3$ and R$^4$ are independently selected from H, alkyl, —(O)$_q$(CH$_2$)$_r$P; wherein said alkyl is optionally substituted with one or more —OH;
q is selected from 0 and 1;
r is selected from 0, 1, 2, and 3;
P is selected from aryl, —SO$_2$R$^6$, —C(O)NH$_2$, and heterocycle; and
R$^6$ is selected from —NH$_2$, —NH(alkyl), —N(alkyl)$_2$,
provided that when R$^{11}$ is aryl or heteroaryl, then
a) x+y≥1;
or
b) R$^{11}$ is substituted with T;
or
c) R$^5$ is NR$^3$R$^4$ and at least one of R$^3$ or R$^4$ is [(O)$_q$(CH$_2$)$_r$P] and q+r≥1;
or
d) at least one of R$^1$ or R$^2$ is alkyl substituted with —C(O)O(CH$_2$)$_t$R$^{12}$.

In one embodiment, the invention relates to a compound having the formula I where R$^{11}$ is aryl or heteroaryl, and x+y≥1.

In another embodiment, the invention relates to a compound having the formula I where R$^{11}$ is aryl or heteroaryl, and R$^{11}$ is substituted with T.

In another embodiment, the invention relates to a compound having the formula I where R$^{11}$ is aryl or heteroaryl, and R$^5$ is NR$^3$R$^4$ where at least one of R$^3$ or R$^4$ is [(O)$_q$(CH$_2$)$_r$P] and q+r≥1.

In another embodiment, the invention relates to a compound having the formula I where R$^{11}$ is aryl or heteroaryl, and at least one of R$^1$ or R$^2$ is alkyl substituted with —C(O)O(CH$_2$)$_t$R$^{12}$.

In another embodiment, the invention relates to a compound having the formula I where R$^{11}$ is aryl or heteroaryl, R$^{11}$ is substituted with T, T is —(O)$_u$(CH$_2$)$_s$C(O)R$^8$ and u+s≥2.

In another embodiment, the invention relates to a compound having the formula I where R$^{11}$ is aryl or heteroaryl, R$^{11}$ is substituted with T, and T is selected from heterocycle, —(CHR$^7$)$_z$OR$^9$, —(O)$_u$(CH$_2$)$_s$C(O)R$^8$, and —OSO$_2$R$^{13}$.

In another embodiment, the invention relates to a compound having the formula I where R$^{11}$ is selected from C$_6$-C$_{10}$ aryl, heteroaryl comprising 1-4 heteroatoms selected from N, O and S, and saturated or partially saturated heterocycle comprising 1-4 heteroatoms selected from N, O and S, wherein when x is 0, said C$_6$-C$_{10}$ aryl or heteroaryl comprising 1-4 heteroatoms selected from N, O and S is substituted with —C(O)NR$^1$R$^2$ or T.

One aspect of the invention relates to a compound having the formula II:

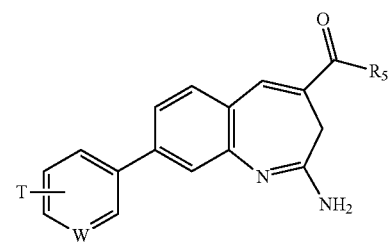

(II)

or a tautomer, enantiomer or salt thereof wherein:
W is selected from N, C-T and CH and T and R$^5$ are as defined above in formula I.

In one embodiment, the invention relates to a compound having the formula IIa:

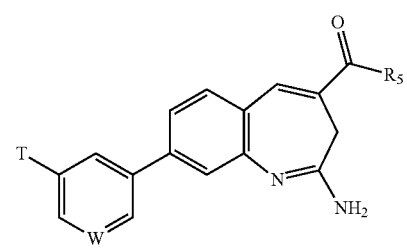

(IIa)

or a tautomer, enantiomer or salt thereof. In another embodiment, the invention relates to a compound having the formula IIb:

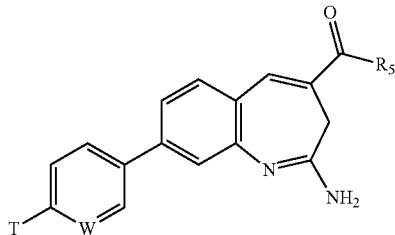

(IIb)

or a tautomer, enantiomer or salt thereof wherein
W is selected from N, C-T and CH and T and $R^5$ are as defined above in formula I.

In one embodiment, the invention relates to a compound of formula II, IIa, or IIb or a salt thereof, wherein W is CH.

In another embodiment, the invention relates to a compound of formula I, II, IIa, or IIb or a salt thereof, wherein T is —(O)$_u$(CH$_2$)$_s$C(O)R$^8$. In one embodiment, the invention relates to a compound or a salt thereof, wherein u is 1 and s is 1. In one embodiment, the invention relates to a compound or a salt thereof, wherein u is 0 and s is 1. In one embodiment, the invention relates to a compound or a salt thereof, wherein u is 0 and s is 2. In one embodiment, the invention relates to a compound or a salt thereof, wherein $R^8$ is —O-alkyl. In one embodiment, the invention relates to a compound or a salt thereof, wherein $R^8$ is —O-alkyl and alkyl is selected from methyl, ethyl, isopropyl, and isobutyl.

In another embodiment, the invention relates to a compound of formula I, II, IIa, or IIb or a salt thereof, wherein T is heterocycle. In one embodiment, the invention relates to a compound or a salt thereof, wherein the heterocycle is selected from dihydrofuranone and dioxolanone. In one embodiment, the invention relates to a compound, wherein heterocycle is selected from

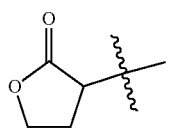 and 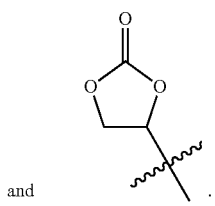.

In another embodiment, the invention relates to a compound of formula I, II, IIa, or IIb or a salt thereof, wherein T is —(CHR$^7$)$_z$OR$^9$.

In another embodiment, the invention relates to a compound of formula I, II, IIa, or IIb or a salt thereof, wherein T is —OSO$_2$R$^{13}$. In one embodiment, the invention relates to a compound or a salt thereof, wherein $R^{13}$ is —CF$_3$.

In another embodiment, the invention relates to a compound of formula II, IIa, or IIb or a salt thereof, wherein W is N. In one embodiment, the invention relates to a compound or a salt thereof, wherein T is —(CHR$^7$)$_z$OR$^9$. In one embodiment, the invention relates to a compound or a salt thereof, wherein z is 1 and $R^7$ and $R^9$ are both hydrogen. In one embodiment, the invention relates to a compound or a salt thereof, wherein z is 2, $R^7$ is OH or H and $R^9$ is H.

Another aspect of the invention relates to a compound having the formula III:

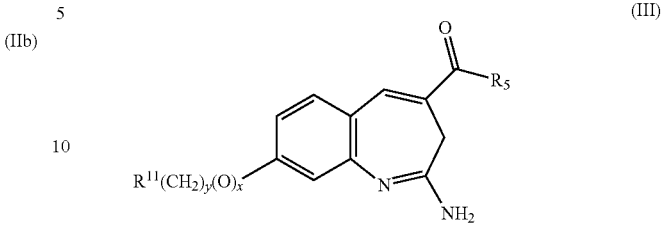

(III)

or a tautomer, enantiomer or salt thereof, wherein $R^5$, $R^{11}$, x and y are as defined above in formula I; provided that when $R^{11}$ is aryl or heteroaryl, then x+y≥1.

In one embodiment, the invention relates to a compound having the formula IIIa:

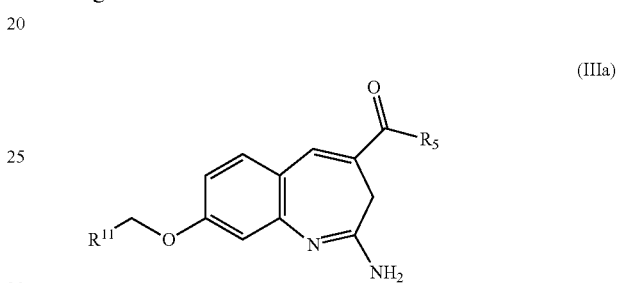

(IIIa)

or a tautomer, enantiomer or salt thereof.

In one embodiment, the invention relates to a compound having the formula IIIb:

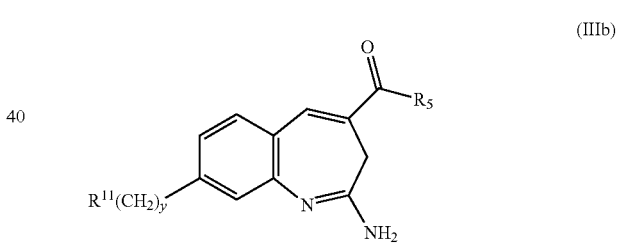

(IIIb)

or a tautomer, enantiomer or salt thereof, wherein y is 1, 2, or 3.

In one embodiment, the invention relates to a compound having the formula IIIc:

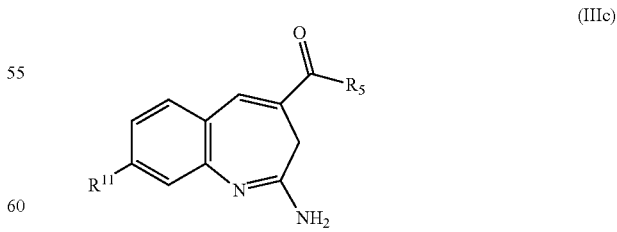

(IIIc)

or a tautomer, enantiomer or salt thereof, wherein $R^{11}$ is saturated or partially saturated heterocycle.

In one embodiment, the invention relates to a compound or a salt thereof, having the formula I, III, IIIa, or IIIb, wherein x=0 and y=3.

In one embodiment, the invention relates to a compound or a salt thereof, having the formula I, III, IIIa, or IIIb, wherein $R^{11}$ is phenyl.

In one embodiment, the invention relates to a compound or a salt thereof, having the formula I, III, IIIa, or IIIb, wherein $R^{11}$ is heterocycle. In one embodiment, the invention relates to a compound or a salt thereof, wherein said heterocycle is partially saturated heterocycle. In one embodiment, the invention relates to a compound or a salt thereof, wherein said heterocycle is morpholine. In one embodiment, the invention relates to a compound or a salt thereof, wherein said heterocycle is isobenzofuranone. In one embodiment, the invention relates to a compound or a salt thereof, wherein said isobenzofuranone is selected from

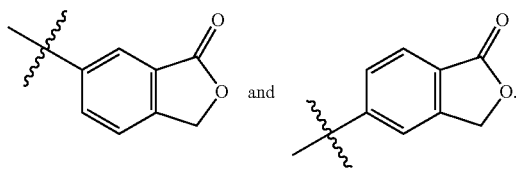 [SMILES: *c1ccc2c(c1)C(=O)OC2 ; "and" ; *c1ccc2c(c1)COC2=O]

Another aspect of the invention relates to a compound or a salt thereof having the formula I, II, IIa, IIb, III, IIIa, or IIIb, wherein $R^5$ is —$OR^{10}$. In one embodiment, the invention relates to a compound or a salt thereof, wherein $R^{10}$ is alkyl. In one embodiment, the invention relates to a compound or a salt thereof, wherein $R^{10}$ is ethyl.

Another aspect of the invention relates to a compound or salt thereof having the formula I, II, IIa, IIb, III, IIIa, or IIIb, wherein $R^5$ is —$NR^3R^4$. In one embodiment, the invention relates to a compound or a salt thereof, wherein, $R^3$ and $R^4$ are both alkyl. In one embodiment, the invention relates to a compound or a salt thereof, wherein $R^3$ and $R^4$ are both propyl. In one embodiment, the invention relates to a compound or a salt thereof, wherein at least one of $R^3$ or $R^4$ is alkyl substituted with one —OH. In one embodiment, the invention relates to a compound or a salt thereof, wherein at least one of $R^3$ or $R^4$ is

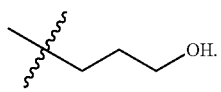 [SMILES: *CCCO]

In another embodiment, the invention relates to a compound or a salt thereof, wherein one of $R^3$ or $R^4$ is

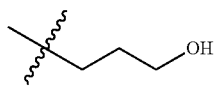 [SMILES: *CCCO]

and the remaining $R^3$ or $R^4$ is propyl.

Another aspect of the invention relates to a compound having the formula IV:

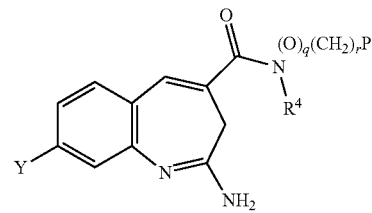

or a tautomer, enantiomer or salt thereof, wherein Y, $R^4$, P, u and t are as defined above in formula I; provided that q+r is ≥1.

In one embodiment, the invention relates to a compound having the formula IVa:

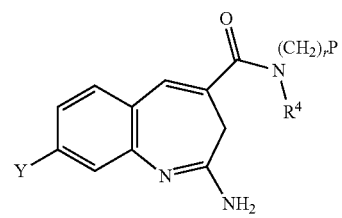

or a tautomer, enantiomer or salt thereof, wherein r is selected from 1, 2, or 3.

In one embodiment, the invention relates to a compound having the formula IVb:

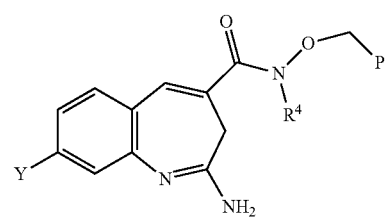

or a tautomer, enantiomer or salt thereof.

In one embodiment, the invention relates to a compound of formula I or IV or a salt thereof, wherein t=3.

In one embodiment, the invention relates to a compound of formula I, IV, IVa, or IVb, or a salt thereof, wherein P is selected from aryl, heterocycle and —$SO_2R^6$.

In one embodiment, the invention relates to a compound of formula I, IV, IVa, or IVb, or a salt thereof, wherein P is heterocycle. In one embodiment, the invention relates to a compound or salt thereof, wherein P is selected from piperidine and pyrrolidine.

In one embodiment, the invention relates to a compound of formula I, IV, IVa, or IVb, or a salt thereof, wherein P is aryl.

In one embodiment, the invention relates to a compound of formula I, IV, IVa, or IVb, or a salt thereof, wherein P is —$SO_2R^6$. In one embodiment, the invention relates to a compound or a salt thereof, wherein said $R^6$ is —$NH_2$.

In one embodiment, the invention relates to a compound of formula I, IV, IVa, or IVb, or a salt thereof, wherein x=0 and y=0. In one embodiment, the invention relates to a compound or a salt thereof, wherein $R^{11}$ is aryl. In one embodiment, the invention relates to a compound or a salt thereof, wherein said aryl is substituted with —C(O)NR$^1$R$^2$. In one embodiment, the invention relates to a compound or a salt thereof, wherein said R$^1$ and R$^2$ together with the nitrogen atom to which they are attached form a saturated heterocyclic ring. In one embodiment, the invention relates to a compound or a salt thereof, wherein said saturated heterocyclic ring is a pyrrolidine ring.

Another aspect of the invention relates to a compound having the formula V:

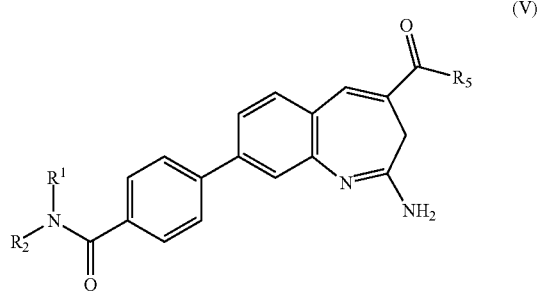

or a tautomer, enantiomer or salt thereof, wherein R$^1$, R$^2$ and R$^5$ are as defined above in formula I, and further wherein at least one of R$^1$ or R$^2$ is alkyl substituted with —C(O)O(CH$_2$)$_r$R$^{12}$.

In one embodiment, the invention relates to a compound of formula V or a salt thereof, wherein at least one of R$^1$ or R$^2$ is alkyl substituted with —C(O)O(CH$_2$)$_r$R$^{12}$. In one embodiment, the invention relates to a compound or a salt thereof, wherein said R$^{12}$ is aryl. In one embodiment, the invention relates to a compound or a salt thereof, wherein R$^1$ or R$^2$ is H.

In another embodiment, the invention relates to a compound having the formula VI:

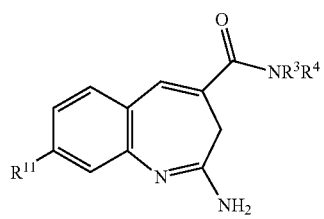

or a tautomer, enantiomer or salt thereof, wherein:
R$^{11}$ is selected from aryl and saturated or partially saturated heterocycle, wherein said aryl is substituted with T;
T is selected from heterocycle, —(O)$_u$(CH$_2$)$_s$C(O)R$^8$, and —CH(OH)CH$_2$OH;
R$^8$ is selected from —OR$^{10}$ and alkyl;
R$^{10}$ is selected from alkyl, —(CH$_2$)R$^{12}$, and hydrogen, wherein said alkyl is optionally substituted with halogen, amine, alkylamine, or dialkylamine;
R$^{12}$ is selected from cycloalkyl and aryl;
u is selected from 0 and 1;
s is selected from 1 and 2; and
R$^3$ and R$^4$ are independently alkyl; wherein said alkyl is optionally substituted with one or more —OH.

In one embodiment, the invention relates to a compound of formula VI or a salt thereof, wherein R$^{11}$ is aryl substituted with —(O)$_u$(CH$_2$)$_s$C(O)R$^8$. In another embodiment, said R$^8$ is —OR$^{10}$.

In another embodiment, the invention relates to a compound having the formula VI, wherein:
R$^{11}$ is selected from aryl and saturated or partially saturated heterocycle, wherein said aryl is substituted with T;
T is selected from heterocycle and —(O)$_u$(CH$_2$)$_s$C(O)R$^8$;
R$^8$ is selected from —OR$^{10}$ and alkyl;
R$^{10}$ is selected from alkyl, —(CH$_2$)R$^{12}$, and hydrogen, wherein said alkyl is optionally substituted with halogen, amine, alkylamine, or dialkylamine;
R$^{12}$ is selected from cycloalkyl and aryl;
u is selected from 0 and 1;
s is selected from 1 and 2; and
R$^3$ and R$^4$ are independently alkyl; wherein said alkyl is optionally substituted with one or more —OH.

In another embodiment, the invention relates to a compound having the formula VI, wherein:
R$^{11}$ is aryl substituted with T;
T is selected from —(O)$_u$(CH$_2$)$_s$C(O)R$^8$, and —CH(OH)CH$_2$OH;
R$^8$ is selected from —OR$^{10}$ and alkyl;
R$^{10}$ is selected from alkyl, —(CH$_2$)R$^{12}$, and hydrogen, wherein said alkyl is optionally substituted with halogen, amine, alkylamine, or dialkylamine;
R$^{12}$ is selected from cycloalkyl and aryl;
u is selected from 0 and 1;
s is selected from 1 and 2; and
R$^3$ and R$^4$ are independently alkyl; wherein said alkyl is optionally substituted with one or more —OH.

In another embodiment, the invention relates to a compound having the formula VI, wherein R$^3$ and R$^4$ are independently alkyl; and further wherein one of R$^3$ and R$^4$ is substituted with one or more —OH while the other is unsubstituted. In another embodiment, the invention relates to a compound having the formula VI, wherein R$^3$ and R$^4$ are independently unsubstituted alkyl. In another embodiment, the invention relates to a compound having the formula VI, wherein R$^{11}$ is aryl. In another embodiment, the invention relates to a compound having the formula VI, wherein R$^{11}$ is phenyl. In another embodiment, the invention relates to a compound having the formula VI, wherein R$^{11}$ is saturated or partially saturated heterocycle.

Another aspect of the invention relates to a compound or a salt thereof, selected from a compound in Table 1. In one embodiment, the invention relates to a compound or a salt thereof, selected from Compound 196, 197, 183, 191, 192, 193, 199, 205, 213, 214, 215, 216, 217, 218, 219, 223, 224, 226, and 225. In one embodiment, the invention relates to a compound or a salt thereof, selected from Compound 113, 175, 116, 118, and 177. In one embodiment, the invention relates to a compound or a salt thereof, selected from Compound 148, 185, 184, 200, 198, 221, and 222. In one embodiment, the invention relates to a compound or a salt thereof, selected from Compound 198, 225, 191, 192, 193, 196, 197, 221, 205, 213, 214, 215, 216, 217, 218, 219, 222, 223 and 224. In one embodiment, the invention relates to a compound or a salt thereof, selected from Compound 198, 225, 191, 192, 193, 197, 221, 205, 213, 214, 215, 216, 217, 218, 219, 222 and 223. In one embodiment, the invention relates to a compound or a salt thereof, selected from Compound 191, 196, and 224.

In one embodiment, the invention relates to a compound having the formula I. In one embodiment, the invention relates to a compound having the formula II. In one embodiment, the invention relates to a compound having the formula IIa. In one embodiment, the invention relates to a compound having the formula IIb. In one embodiment, the invention relates to a compound having the formula III. In one embodiment, the invention relates to a compound having the formula IIIa. In one embodiment, the invention relates to a compound having the formula IIIb. In one embodiment, the invention relates to a compound having the formula IIIc. In one embodiment, the invention relates to a compound having the formula IV. In one embodiment, the invention relates to a compound having the formula IVa. In one embodiment, the invention relates to a compound having the formula IVb. In one embodiment, the invention relates to a compound having the formula V. In one embodiment, the invention relates to a compound having the formula VI.

Another aspect of the invention relates to a compound of the invention or salt thereof, wherein the salt is a pharmaceutically acceptable salt.

Another aspect of the invention relates to a kit for treating a TLR7- and/or TLR8-mediated condition, comprising:
(a) a first pharmaceutical composition comprising a compound of the invention or salt thereof; and (b) optionally instructions for use.

In one embodiment, the kit further comprises (c) a second pharmaceutical composition, wherein the second pharmaceutical composition comprises a second compound for treating a TLR7- and/or TLR8-mediated condition.

In one embodiment, the kit further comprises instructions for the simultaneous, sequential or separate administration of said first and second pharmaceutical compositions to a patient in need thereof.

Another aspect of the invention relates to a pharmaceutical composition, which comprises a compound of the invention or salt thereof, together with a pharmaceutically acceptable diluent or carrier.

Another aspect of the invention relates to a compound of the invention, or salt thereof, for use as a medicament for treating a TLR7 and/or TLR8-mediated condition in a human or animal. In one embodiment, the invention relates to the use of a compound of the invention or salt thereof, in the manufacture of a medicament for the treatment of an abnormal cell growth condition in a human or animal.

Another aspect of the invention relates to a method of treating a TLR7- and/or TLR8-mediated condition, comprising administering to a patient in need thereof an effective amount of a compound of the invention or salt thereof.

Another aspect of the invention relates to a method of modulating a patient's immune system, comprising administering to a patient in need thereof an effective amount of a compound of the invention or salt thereof.

The invention includes a compound selected from the compounds listed in Table 1.

TABLE 1

| # | Chemical Structure | # | Chemical Structure |
|---|---|---|---|
| 113 | 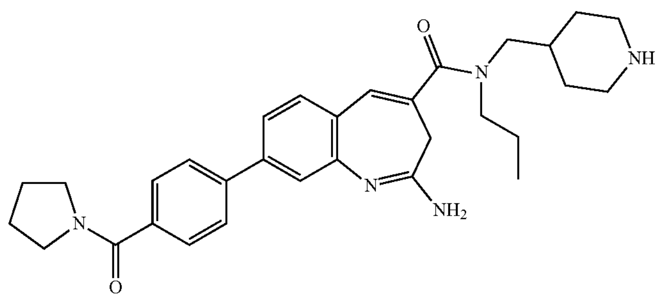 [SMILES: CCCN(CC1CCNCC1)C(=O)C1=Cc2ccc(-c3ccc(C(=O)N4CCCC4)cc3)cc2N=C(N)C1] | 116 | 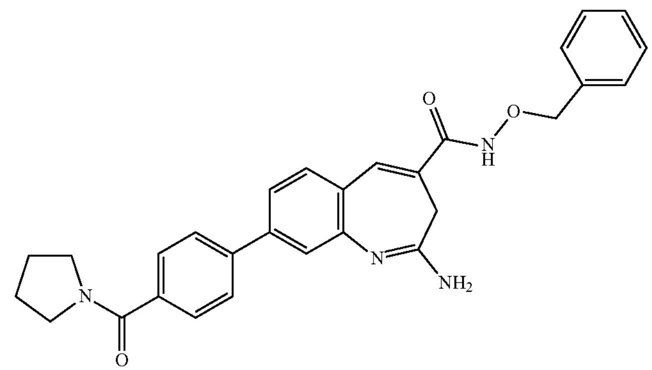 [SMILES: NC1=Nc2cc(-c3ccc(C(=O)N4CCCC4)cc3)ccc2C=C(C(=O)NOCc2ccccc2)C1] |
| 148 | 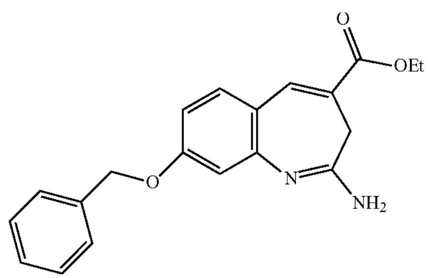 [SMILES: CCOC(=O)C1=Cc2ccc(OCc3ccccc3)cc2N=C(N)C1] | 118 | 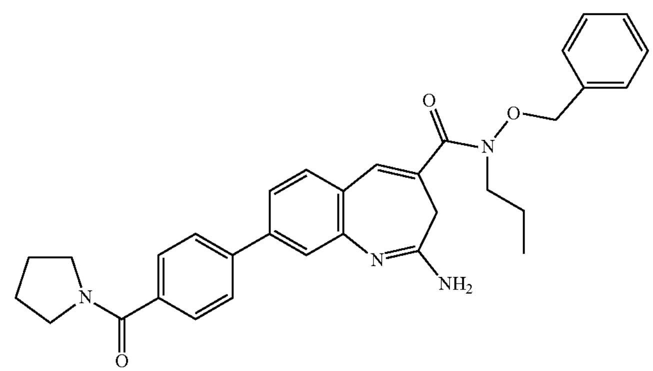 [SMILES: CCCN(OCc1ccccc1)C(=O)C1=Cc2ccc(-c3ccc(C(=O)N4CCCC4)cc3)cc2N=C(N)C1] |

TABLE 1-continued

| # | Chemical Structure |
|---|---|
| 175 | (structure) |
| 177 | (structure) |
| 183 | (structure) |
| 184 | (structure) |

TABLE 1-continued

| # | Chemical Structure | # | Chemical Structure |
|---|---|---|---|
| 185 | 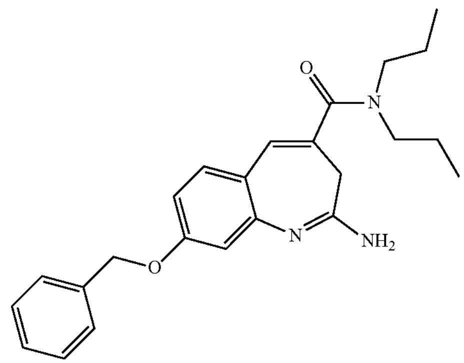 [SMILES: CCCN(CCC)C(=O)C1=Cc2ccc(OCc3ccccc3)cc2N=C(N)C1] | 225 | 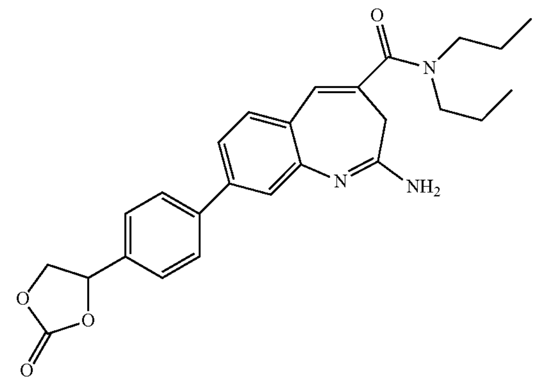 [SMILES: CCCN(CCC)C(=O)C1=Cc2ccc(-c3ccc(C4COC(=O)O4)cc3)cc2N=C(N)C1] |
| 191 | 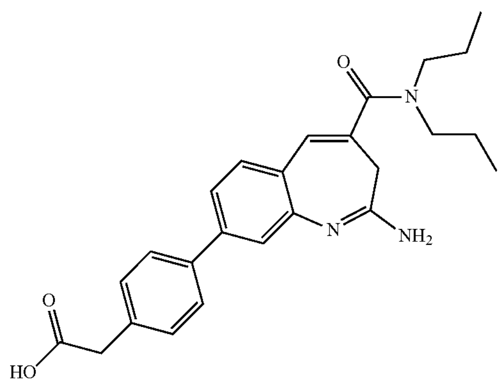 [SMILES: CCCN(CCC)C(=O)C1=Cc2ccc(-c3ccc(CC(=O)O)cc3)cc2N=C(N)C1] | 192 | 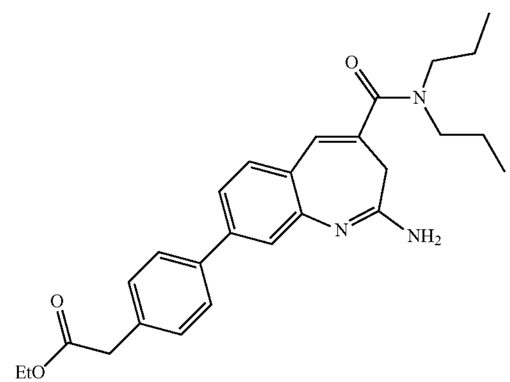 [SMILES: CCCN(CCC)C(=O)C1=Cc2ccc(-c3ccc(CC(=O)OCC)cc3)cc2N=C(N)C1] |

TABLE 1-continued

| # | Chemical Structure |
|---|---|
| 193 | (structure) |
| 196 | (structure) |
| 197 | (structure) |
| 198 | (structure) |

TABLE 1-continued

| # | Chemical Structure | # | Chemical Structure |
|---|---|---|---|
| 199 | (structure) | 200 | (structure) |
| 205 | (structure) | 213 | (structure) |
| 214 | (structure) | 215 | (structure) |

TABLE 1-continued

| # | Chemical Structure |
|---|---|
| 216 | |
| 217 | |
| 218 | |
| 219 | |
| 221 | |
| 222 | |

TABLE 1-continued

| # | Chemical Structure | # | Chemical Structure |
|---|---|---|---|
| 223 | 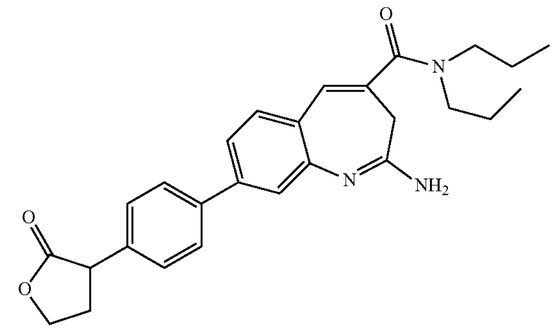 [SMILES: CCCN(CCC)C(=O)C1=Cc2ccc(-c3ccc(C4CCOC4=O)cc3)cc2N=C(N)C1] | 224 | 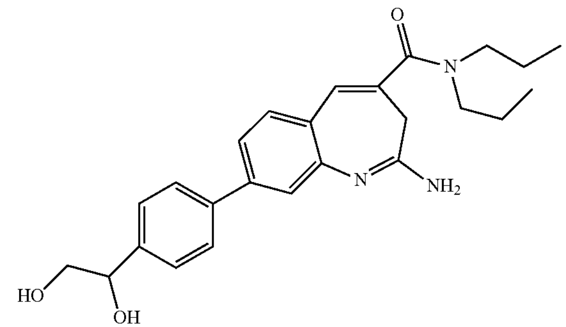 [SMILES: CCCN(CCC)C(=O)C1=Cc2ccc(-c3ccc(C(O)CO)cc3)cc2N=C(N)C1] |
| 226 | 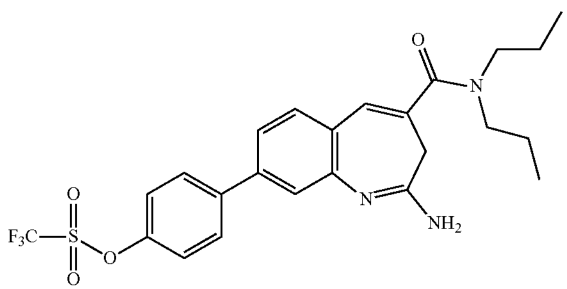 [SMILES: CCCN(CCC)C(=O)C1=Cc2ccc(-c3ccc(OS(=O)(=O)C(F)(F)F)cc3)cc2N=C(N)C1] | 201 | 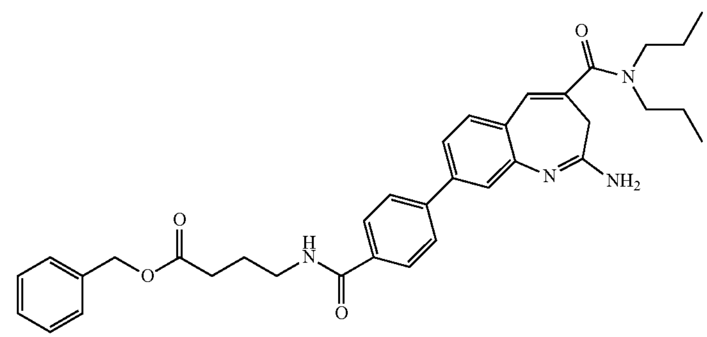 [SMILES: CCCN(CCC)C(=O)C1=Cc2ccc(-c3ccc(C(=O)NCCCC(=O)OCc4ccccc4)cc3)cc2N=C(N)C1] |
| 227 | 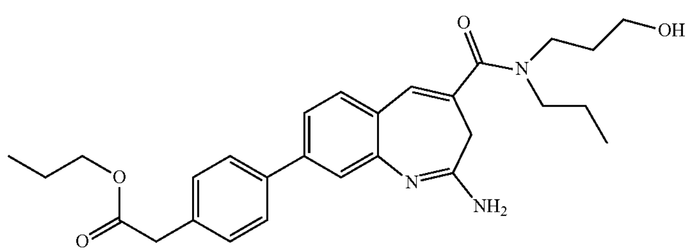 [SMILES: CCCOC(=O)Cc1ccc(-c2ccc3c(c2)N=C(N)CC(C(=O)N(CCC)CCCO)=C3)cc1] | 228 | 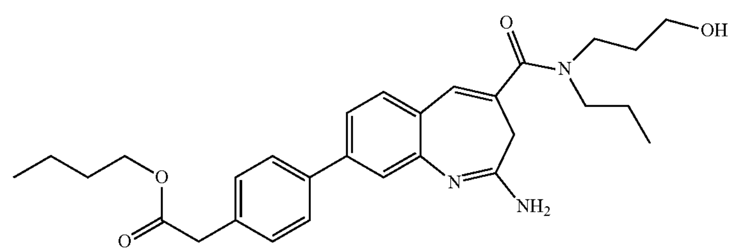 [SMILES: CCCCOC(=O)Cc1ccc(-c2ccc3c(c2)N=C(N)CC(C(=O)N(CCC)CCCO)=C3)cc1] |

TABLE 1-continued

| # | Chemical Structure | # | Chemical Structure |
|---|---|---|---|
| 229 | (structure) | 230 | (structure) |
| 231 | (structure) | 232 | (structure) |
| 233 | (structure) | 234 | (structure) |

TABLE 1-continued
| # | Chemical Structure | # | Chemical Structure |
|---|---|---|---|
| 235 | 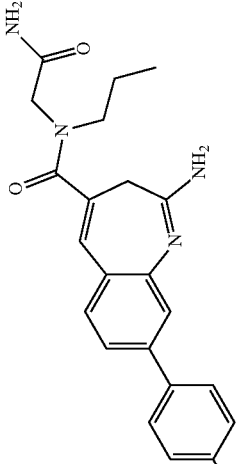 | 236 | 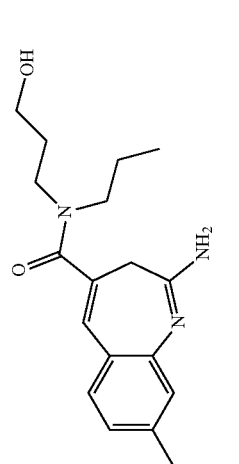 |
| 237 | 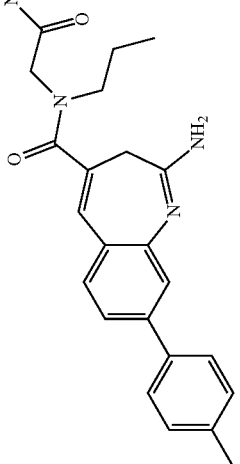 | 238 | 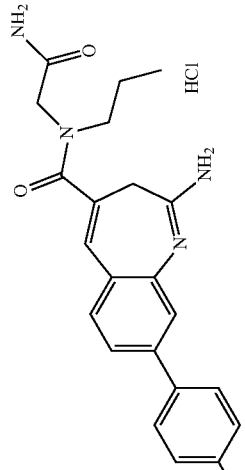 |

In one aspect, the invention includes a compound, or salt thereof, with an $MC_{50}$ value≤25,000 nM for TLR8. In another aspect, the invention includes a compound or salt thereof, with an $MC_{50}$ value≤10,000 nM for TLR8. In another aspect, the invention includes a compound or salt thereof, with an $MC_{50}$ value≤1,000 nM for TLR8. In another aspect, the invention includes a compound or salt thereof, with an $MC_{50}$ value≤100 nM for TLR8. In another aspect, the invention includes a compound or salt thereof, with an $MC_{50}$ value≤25 nM for TLR8.

In one aspect, the invention includes a compound or salt thereof, with an $MC_{50}$ value≤25,000 nM for TLR7. In another aspect, the invention includes a compound or salt thereof, with an $MC_{50}$ value≤10,000 nM for TLR7. In another aspect, the invention includes a compound or salt thereof, with an $MC_{50}$ value≤1,000 nM for TLR7. In another aspect, the invention includes a compound or salt thereof, with an $MC_{50}$ value≤100 nM for TLR7. In another aspect, the invention includes a compound or salt thereof, with an $MC_{50}$ value≤25 nM for TLR7.

In one aspect, the invention does not include a compound or salt thereof, with an $MC_{50}$>25,000 for TLR7. In one aspect, the invention does not include a compound or salt thereof, with an $MC_{50}$>25,000 for TLR8. In one aspect, the invention does not include a compound or salt thereof, with $MC_{50}$ values>25,000 for both TLR7 and for TLR8.

Another aspect of the invention relates to soft drugs (also known as "antedrugs"). "Soft drugs" can be defined as biologically active chemical compounds (drugs) which are metabolically deactivated after they achieve their therapeutic role at their designed site of action. The use of soft drugs, instead of their non-deactivatable analogs, can avoid unwanted side effects. In one aspect, the metabolic disposition of the soft drugs takes place with a controllable rate in a predictable manner. One embodiment of the invention relates to compounds that are soft drugs. Specifically, the invention relates to compounds that are designed to cleave in vivo, after achieving their therapeutic effect, to a less active moiety. The invention relates to compounds that are designed to cleave in vivo, after achieving their therapeutic effect, to a non-toxic moiety. Soft drugs of the invention include compounds such as Compound 225, 192, 193, 197, 198, 205, 213, 214, 215, 216, 217, 218, 219, 221, 222 and 223.

The term "compound of the invention" refers to exemplified compounds and compounds covered under the formulae described herein.

The term "substituted," as used herein, means that any one or more hydrogen atoms on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

A chemical structure showing a dotted line representation for a chemical bond indicates that the bond is optionally present. For example, a dotted line drawn next to a solid single bond indicates that the bond can be either a single bond or a double bond.

When a bond to a substituent is shown to cross a bond connecting two atoms in a ring, then such substituent can be bonded to any atom on the ring.

The term "alkyl" as used herein refers to a saturated linear or branched-chain monovalent hydrocarbon radical having one to twelve, including one to ten carbon atoms ($C_1$-$C_{10}$), one to six carbon atoms ($C_1$-$C_6$) and one to four carbon atoms ($C_1$-$C_4$), wherein the alkyl radical may be optionally substituted independently with one or more substituents described below. Examples of alkyl radicals include hydrocarbon moieties such as, but not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, and 1-octyl.

The term "alkenyl" refers to a linear or branched-chain monovalent hydrocarbon radical having two to 10 carbon atoms ($C_2$-$C_{10}$), including two to six carbon atoms ($C_2$-$C_6$) and two to four carbon atoms ($C_2$-$C_4$), and at least one double bond, and includes, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations. The term "alkenyl" includes allyl.

The term "alkynyl" refers to a linear or branched monovalent hydrocarbon radical of two to twelve carbon atoms ($C_2$-$C_{12}$), including two to 10 carbon atoms ($C_2$-$C_{10}$), two to six carbon atoms ($C_2$-$C_6$) and two to four carbon atoms ($C_2$-$C_4$), containing at least one triple bond. Examples include, but are not limited to, ethynyl, propynyl, butynyl, pentyn-2-yl and the like, wherein the alkynyl radical may be optionally substituted independently with one or more substituents described herein.

The terms "carbocycle," "carbocyclyl," or "cycloalkyl" are used interchangeably herein and refer to saturated or partially unsaturated cyclic hydrocarbon radical having from three to twelve carbon atoms ($C_3$-$C_{12}$), including from three to ten carbon atoms ($C_3$-$C_{10}$) and from three to six carbon atoms ($C_3$-$C_6$). The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system, or as bridged systems such as bicyclo[2.2.1]heptane, bicyclo [2.2.2]octane, and bicyclo[3.2.2]nonane. The cycloalkyl may be optionally substituted independently at one or more substitutable positions with one or more substituents described herein. Such cycloalkyl groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl and di($C_1$-$C_6$)alkylamino($C_1$-$C_6$)alkyl.

The term "cycloalkenyl" refers to a partially unsaturated cyclic hydrocarbon radical having from three to ten carbon atoms ($C_3$-$C_{10}$), including from three to six carbon atoms ($C_3$-$C_6$) and having at least one double bond within the carbocycle.

The term "heteroalkyl" refers to saturated linear or branched-chain monovalent hydrocarbon radical of one to twelve carbon atoms ($C_1$-$C_{12}$), including from one to six carbon atoms ($C_1$-$C_6$) and from one to four carbon atoms ($C_1$-$C_4$), wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" and "heterocyclyl" are used interchangeably herein and refer to a saturated or partially unsaturated carbocyclic radical of 3 to 8 ring atoms in which at least one ring atom is a heteroatom selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. The term further includes fused ring systems which include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, one or more groups independently selected from $C_1$-$C_6$ alkyl, $C_1$-$C_6$ alkoxy, halogen, hydroxy, cyano, nitro, amino, mono($C_1$-$C_6$)alkylamino, di($C_1$-$C_6$6)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl, etc.), which is optionally substituted with one or more substituents independently selected from, for example, halogen, lower alkyl, lower alkoxy, trifluoromethyl, aryl, heteroaryl and hydroxy. In one embodiment, the aryl is a 6-membered aryl. For example, aryl is phenyl.

The term "heteroaryl" refers to a monovalent aromatic radical of 5-, 6-, or 7-membered rings and includes fused ring systems (at least one of which is aromatic) of 5-10 atoms containing at least one and up to four heteroatoms selected from nitrogen, oxygen, and sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, isobenzofuran-1(3H)-one, and furopyridinyl. Spiro moieties are also included within the scope of this definition. Heteroaryl groups are optionally substituted with one or more substituents independently selected from, for example, halogen, lower alkyl, lower alkoxy, haloalkyl, aryl, heteroaryl, and hydroxy.

The term "halogen" represents fluorine, bromine, chlorine, and iodine.

The term "oxo" represents =O.

In general, the various moieties or functional groups of the compounds of the invention may be optionally substituted by one or more substituents. Examples of substituents suitable for purposes of this invention include, but are not limited to, oxo, halogen, cyano, nitro, trifluoromethyl, difluoromethoxy, trifluoromethoxy, azido, —NR"SO$_2$R', —SO$_2$NR'R", —C(O)R', —C(O)OR', —OC(O)R, —NR"C(O)OR', —NR"C(O)R', —C(O)NR'R", —NRC(O)NR", —NRC(NCN)NR'R", —OR', aryl, heteroaryl, arylalkyl, heteroarylalkyl, heterocyclyl, and heterocyclylalkyl, where R', R" and R''' are independently H, alkyl, heteroalkyl, cycloalkyl, heterocycloalkyl, alkenyl, alkynyl, aryl or heteroaryl.

An "(alkyl)aryl" group, as used herein, is an aryl substituent that is linked to a compound by a straight chain or branched alkyl group having from one to twelve carbon atoms. In one aspect, the aryl substituent is linked to a compound by a straight chain or branched alkyl group having 1-6 carbon atoms. The alkyl moiety of the (alkyl)aryl group is optionally substituted. In one embodiment, the aryl is a 6-membered aryl. For example, aryl is phenyl.

An "(alkyl)heterocycloalkyl" group, as used herein, is a heterocycle substituent that is linked to a compound by a straight chain or branched alkyl group having from one to twelve carbon atoms. In one aspect, the heterocycle substituent is linked to a compound by a straight chain or branched alkyl group having 1-6 carbon atoms. The alkyl moiety of the (alkyl)heterocycle group is optionally substituted.

An "(alkyl)cycloalkyl" group, as used herein, is a cycloalkyl substituent that is linked to a compound by a straight chain or branched alkyl group having from one to twelve carbon atoms. In one aspect, the cycloalkyl substituent is linked to a compound by a straight chain or branched alkyl group having 1-6 carbon atoms. The alkyl moiety of the (alkyl)cycloalkyl group is optionally substituted.

An "(alkyl)cycloalkenyl" group, as used herein, is a cycloalkenyl substituent that is linked to a compound by a straight chain or branched alkyl group having from one to twelve carbon atoms. In one aspect, the cycloalkenyl substituent is linked to a compound by a straight chain or branched alkyl group having 1-6 carbon atoms. The alkyl moiety of the (alkyl)cycloalkenyl group is optionally substituted.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the compounds and formulae described herein.

Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. Enantiomers can also be separated by use of a chiral HPLC column. Methods for the determination of stereochemistry and the separation of stereoisomers are well known in the art (see discussion in Chapter 4 of "Advanced Organic Chemistry", 4th edition, J. March, John Wiley and Sons, New York, 1992).

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

A single stereoisomer, e.g. an enantiomer, substantially free of its stereoisomer may be obtained by resolution of the racemic mixture using a method such as formation of diastereomers using optically active resolving agents (Eliel, E. and Wilen, S. Stereochemistry of Organic Compounds, John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Drug Stereochemistry, Analytical Methods and Pharmacology, Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, a-methyl-13-phenyl-ethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, for example a menthyl ester such as (-) menthyl chloroformate, in the presence of base, or Mosher ester, a-methoxy¬ a-(trifluoromethyl)phenyl acetate (Jacob III, (1982) J. Org. Chem. 47:4165), of the racemic mixture, and analyzing the NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase (Chiral Liquid Chromatography (1989) W. J. Lough, Ed., Chapman and Hall, New York; Okamoto, (1990) J. of Chromatogr. 513:375-378). Enriched or purified enantiomers can be distinguished by methods used to distinguish other chiral molecules with asymmetric carbon atoms, such as optical rotation and circular dichroism.

"Tautomer" refers to a compound whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomer form.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

In addition to compounds of the invention, the invention also includes pharmaceutically acceptable salts of such compounds.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, pheylacetates, phenylpropionates, phenylbutyrates, citrates, lactates, y-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moieties, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N¬ methylglucosamine, plus salts formed with basic amino acids such as glycine, ornithine, histidine, phenylglycine, lysine and arginine.

The present invention also provides salts of compounds of the invention which are not necessarily pharmaceutically acceptable salts, but which may be useful as intermediates for preparing and/or purifying compounds of the invention and/or for separating enantiomers of compounds of the invention.

The inventive compounds may be prepared using the reaction routes and synthesis schemes as described in Scheme I, employing the techniques available in the art using starting materials that are readily available.

Scheme I

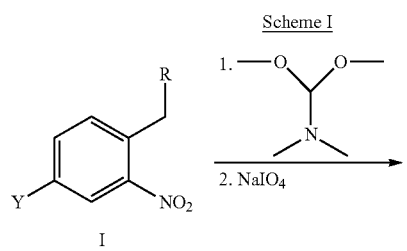

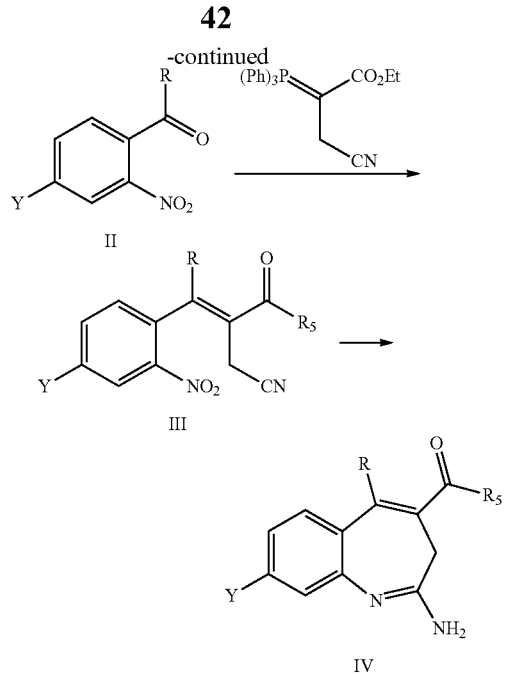

In Scheme I, compounds of Formula II may be prepared from an alkyl arene of Formula I by treatment with dimethylformamide dimethyl acetal with or without the use of pyrrolidine (J. Org. Chem., (1986), 51(26), 5106-5110) in DMF at 70-90° C. The crude intermediate (not shown) may be cleaved to the aldehyde of Formula II with NaIO4 in THF/pH 7.2 phosphate buffer at or around room temperature. The aldehyde of Formula II may be olefinated with phosphonium glide in toluene at temperatures ranging from 70 to 110° C. (1-16 hours) to give compounds of Formula III. Compounds of Formula IV can be prepared from a compound of Formula III using iron powder in acetic acid. The reaction may be conducted at temperatures of about 90° C. for about 3-14 hours.

It is noted that some of the preparations of compounds of the invention described herein may require protection of remote functionalities. The need for such protection will vary depending on the nature of the functionality and the conditions used in the preparation methods and can be readily determined by those skilled in the art. Such protection/deprotection methods are well known to those skilled in the art.

The compounds of the invention find use in a variety of applications. For example, in certain aspects the invention provides methods for modulating TLR7- and/or TLR8-mediated signaling. The methods of the invention are useful, for example, when it is desirable to alter TLR7- and/or and/or TLR8-mediated signaling in response to a suitable TLR7 and/or TLR8 ligand or a TLR7 and/or TLR8 signaling agonist.

As used herein, the terms "TLR7 and/or TLR8 ligand," "ligand for TLR7 and/or TLR8," and "TLR7 and/or TLR8 signaling agonist" refer to a molecule, other than a compound of the invention, that interacts directly or indirectly with TLR7 and/or TLR8 and induces TLR7- and/or TLR8¬ mediated signaling. In certain embodiments, a TLR7 and/or TLR8 ligand is a natural ligand, i.e., a TLR7 and/or TLR8 ligand that is found in nature. In certain embodiments, a TLR7 and/or TLR8 ligand refers to a molecule other than a natural ligand of TLR7 and/or TLR8, e.g., a molecule prepared by human activity.

The term "modulate" as used herein with respect to the TLR7 and/or TLR8 receptors means the mediation of a pharmacodynamic response in a subject by (i) inhibiting or activating the receptor, or (ii) directly or indirectly affecting the normal regulation of the receptor activity. Compounds that modulate the receptor activity include agonists, antagonists, mixed agonists/antagonists and compounds that directly or indirectly affect regulation of the receptor activity.

The term "agonist" refers to a compound that, in combination with a receptor (e.g., a TLR), can produce a cellular response. An agonist may be a ligand that directly binds to the receptor. Alternatively, an agonist may combine with a receptor indirectly by, for example, (a) forming a complex with another molecule that directly binds to the receptor, or (b) otherwise resulting in the modification of another compound so that the other compound directly binds to the receptor. An agonist may be referred to as an agonist of a particular TLR (e.g., a TLR7 and/or TLR8 agonist). The term "partial agonist" refers to a compound that produces a partial but not a full cellular response. TLR7 and TLR8-related assays are known in the art (e.g., Gorden et al., *Journal of Immunology* 177, pp. 8164-8170 (2006) and Zhu et al., *Molecular Immunology*, vol. 45 (11), pp. 3238-3242 (2008)).

The term "antagonist" as used herein refers to a compound that competes with an agonist or partial agonist for binding to a receptor, thereby blocking the action of an agonist or partial agonist on the receptor. More specifically, an antagonist is a compound that inhibits the activity of a TRL7 or a TLR8 agonist at the TLR7 or TLR8 receptor, respectively.

"Inhibit" refers to any measurable reduction of biological activity. Thus, as used herein, "inhibit" or "inhibition" may be referred to as a percentage of a normal level of activity.

In one aspect of this invention, a method of treating or preventing a condition or disorder treatable by modulation of TLR7- and/or TLR8-mediated cellular activities in a subject comprises administering to said subject a composition comprising a compound of the invention in an amount effective to treat or prevent the condition or disorder. The term "TLR7- and/or TLR8-mediated" refers to a biological or biochemical activity that results from TLR7- and/or TLR8 function.

Conditions and disorders that can be treated by the methods of this invention include, but are not limited to, cancer, immune complex-associated diseases, autoimmune diseases or disorders, inflammatory disorders, immunodeficiency, graft rejection, graft-versus-host disease, allergies, cardiovascular disease, fibrotic disease, asthma, infection, and sepsis.

More specifically, methods useful in the treatment of conditions involving cancer (therapeutic or cancer vaccine), allergic disease (e.g., atopic dermatitis, allergic rhinitis, asthma), infectious disease (prophylaxis with vaccine and anti-viral), and immunodeficiency will employ compounds of the invention that inhibit TLR7- and/or TLR8-mediated signaling.

Alternatively, methods useful in the treatment of conditions involving autoimmune disease, CF, sepsis, graft rejection, and GVHD generally will employ compounds of the invention that augment TLR7- and/or TLR8-mediated signaling.

In some instances the compositions can be used to inhibit or promote TLR7- and/or TLR8-mediated signaling in response to a TLR7 and/or TLR8 ligand or signaling agonist.

In other instances the compositions can be used to inhibit or promote TLR7- and/or TLR8-mediated immunostimulation in a subject.

The term "treating" as used herein, unless otherwise indicated, means at least the mitigation of a disease or condition and includes, but is not limited to, modulating and/or inhibiting an existing disease or condition, and/or alleviating the disease or condition to which such term applies, or one or more symptoms of such disease or condition. The term "treatment," as used herein, unless otherwise indicated, refers to the act of treating as "treating" is defined immediately above. Therapeutic treatment refers to treatment initiated after observation of symptoms and/or a suspected exposure to a causative agent of the disease or condition. Generally, therapeutic treatment may reduce the severity and/or duration of symptoms associated with the disease or condition.

As used herein, "preventing" means causing the clinical symptoms of a disease or condition not to develop i.e., inhibiting the onset of a disease or condition in a subject that may be exposed to or predisposed to the disease or condition, but does not yet experience or display symptoms of the disease or condition. Prophylatic treatment means that a compound of the invention is administered to a subject prior to observation of symptoms and/or a suspected exposure to a causative agent of the condition (e.g., a pathogen or carcinogen). Generally, prophylactic treatment may reduce (a) the likelihood that a subject that receives the treatment develops the condition and/or (b) the duration and/or severity of symptoms in the event the subject develops the condition.

As used herein, the terms "autoimmune disease," "autoimmune disorder" and "autoimmunity" refer to immunologically mediated acute or chronic injury to a tissue or organ derived from the host. The terms encompass both cellular and antibody-mediated autoimmune phenomena, as well as organ-specific and organ-nonspecific autoimmunity. Autoimmune diseases include insulin-dependent diabetes mellitus, rheumatoid arthritis, systemic lupus erythematosus, multiple sclerosis, atherosclerosis, and inflammatory bowel disease. Autoimmune diseases also include, without limitation, ankylosing spondylitis, autoimmune hemolytic anemia, Bechet's syndrome, Goodpasture's syndrome, Graves' disease, Guillain Barre syndrome, Hashimoto's thyroiditis, idiopathic thrombocytopenia, myasthenia gravis, pernicious anemia, polyarteritis nodosa, polymyositis/dermatomyositis, primary biliary sclerosis, psoriasis, sarcoidosis, sclerosing cholangitis, Sjogren's syndrome, systemic sclerosis (scleroderma and CREST syndrome), Takayasu's arteritis, temporal arteritis, and Wegener's granulomatosis. Autoimmune diseases also include certain immune complex-associated diseases.

As used here in, the term "fibrotic disease" refers to diseases or disorders involving excessive and persistent formation of scar tissue associated with organ failure in a variety of chronic diseases affecting the lungs, kidneys, eyes, heart, liver, and skin. Although tissue remodeling and scarring is part of the normal wound healing process, repeated injury or insult can lead to persistent and excessive scarring and, ultimately, organ failure.

Fibrotic conditions include diffuse fibrotic lung disease, chronic kidney disease, including diabetic kidney disease; liver fibrosis (e.g., chronic liver disease (CLD) caused by continuous and repeated insults to the liver from causes such as are viral hepatitis B and C, alcoholic cirrhosis or non-alcoholic fatty liver disease (NAFLD), or primary sclerosing cholangitis (PSC), a rare disease characterized by fibrosing inflammatory destruction of the bile ducts inside and outside the liver, leading to bile stasis, liver fibrosis, and ultimately to cirrhosis, and end-stage liver disease); lung fibrosis (e.g., idiopathic pulmonary fibrosis (IPF)); and systemic sclerosis (a degenerative disorder in which excessive fibrosis occurs in multiple organ systems, including the skin, blood vessels, heart, lungs, and kidneys).

Other examples include cystic fibrosis of the pancreas and lungs; injection fibrosis, which can occur as a complication of intramuscular injections, especially in children; endomyocardial fibrosis; mediastinal fibrosis, myelofibrosis; retroperitoneal fibrosis; progressive massive fibrosis, a complication of coal workers' pneumoconiosis; nephrogenic systemic fibrosis; and complication of certain types of surgical implants (e.g. occurrence in attempts at creating an artificial pancreas for the treatment of diabetes mellitus.

As used herein, the term "cardiovascular disease" refers to diseases or disorders of the cardiovascular system involving an inflammatory component, and/or the accumulation of plaque, including without limitation coronary artery disease, cerebrovascular disease, peripheral arterial disease, atherosclerosis, and arteriosclerosis.

As used herein, the terms "cancer" and, "tumor" refer to a condition in which abnormally replicating cells of host origin are present in a detectable amount in a subject. The cancer can be a malignant or non-malignant cancer. Cancers or tumors include, but are not limited to, biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; thyroid cancer; as well as other carcinomas and sarcomas. Cancers can be primary or metastatic.

As used herein, the terms "inflammatory disease" and inflammatory disorder" refer to a condition characterized by inflammation e.g., a localized protective reaction of tissue to irritation, injury, or infection, characterized by pain, redness, swelling, and sometimes loss of function. Inflammatory diseases or disorders include e.g., allergy, asthma, and allergic rash.

As used herein, the term "immune complex-associated disease" refers to any disease characterized by the production and/or tissue deposition of immune complexes (i.e., any conjugate including an antibody and an antigen specifically bound by the antibody), including, but not limited to systemic lupus erythematosus (SLE) and related connective tissue diseases, rheumatoid arthritis, hepatitis C- and hepatitis B-related immune complex disease (e.g., cryoglobulinemia), Bechet's syndrome, autoimmune glomerulonephritides, and vasculopathy associated with the presence of LDL/anti-LDL immune complexes.

As used herein, "immunodeficiency" refers to a disease or disorder in which the subject's immune system is not functioning in normal capacity or in which it would be useful to boost a subject's immune response, for example to eliminate a tumor or cancer (e.g., tumors of the brain, lung (e.g., small cell and non-small cell), ovary, breast, prostate, colon, as well as other carcinomas and sarcomas) or an infection in a subject. The immunodeficiency can be acquired or it can be congenital.

As used herein, "graft rejection" refers to immunologically mediated hyperacute, acute, or chronic injury to a tissue or organ derived from a source other than the host. The term thus encompasses both cellular and antibody-mediated rejection, as well as rejection of both allografts and xenografts.

"Graft-versus-host disease" (GvHD) is a reaction of donated bone marrow against a patient's own tissue. GVHD is seen most often in cases where the blood marrow donor is unrelated to the patient or when the donor is related to the patient but not a perfect match. There are two forms of GVHD: an early form called acute GVHD that occurs soon after the transplant when the white cells are on the rise and a late form called chronic GVHD.

$T_{H2}$-mediated, atopic diseases include, but are not limited to, atopic dermatitis or eczema, eosinophilia, asthma, allergy, allergic rhinitis, and Ommen's syndrome.

As used herein, "allergy" refers to acquired hypersensitivity to a substance (allergen). Allergic conditions include eczema, allergic rhinitis or coryza, hay fever, asthma, urticaria (hives) and food allergies, and other atopic conditions As used herein, "asthma" refers to a disorder of the respiratory system characterized by inflammation, narrowing of the airways and increased reactivity of the airways to inhaled agents. Asthma is frequently, although not exclusively associated with atopic or allergic symptoms. For example, asthma can be precipitated by exposure to an allergen, exposure to cold air, respiratory infection, and exertion.

As used herein, the terms "infection" and, equivalently, "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

As used herein, the term "sepsis" refers to the presence of bacteria (bacteremia) or other infectious organisms or their toxins in the blood (septicemia) or in other tissue of the body.

Further provided is a compound of the invention, or a salt thereof, for use as a medicament in the treatment of the diseases or conditions described above in a mammal, for example, a human, suffering from such disease or condition. Also provided is the use of a compound of the invention, or a salt thereof, in the preparation of a medicament for the treatment of the diseases and conditions described above in a mammal, for example a human, suffering from such disorder.

This invention also encompasses pharmaceutical compositions containing a compound of the invention and methods of treating or preventing conditions and disorders by modulation of TLR7- and/or TLR8-mediated cellular activities by administering a pharmaceutical composition comprising a compound of the invention, or a salt thereof, to a patient in need thereof.

In order to use a compound of the invention or a salt thereof for the therapeutic treatment (including prophylactic treatment) of mammals including humans, it is normally formulated in accordance with standard pharmaceutical practice as a pharmaceutical composition.

According to this aspect of the invention there is provided a pharmaceutical composition that comprises a compound of the invention, or a salt thereof, as defined hereinbefore in association with a pharmaceutically acceptable diluent or carrier.

To prepare the pharmaceutical compositions according to this invention, a therapeutically or prophylactically effective amount of a compound of the invention or a salt thereof (alone or together with an additional therapeutic agent as disclosed herein) is intimately admixed, for example, with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, antibacterial and antifungal agents, isotonic and absorption delaying agents, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of the invention, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as *arachis* oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or *arachis* oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. For parenteral formulations, the carrier will usually comprise sterile water, aqueous sodium chloride solution, 1,3-butanediol, or any other suitable non toxic parenterally acceptable diluent or solvent. Other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 micron or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for transdermal administration may be in the form of those transdermal skin patches that are well known to those of ordinary skill in the art. Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Compositions may be administered in the form of a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's Pharmaceutical Sciences, Ed. By Arthur Osol, p. 1445 (1980)). Of course, the ordinary artisan can readily determine a suitable saline content and pH for an innocuous aqueous carrier for nasal administration.

Other, non-limiting examples of intranasal dosage forms containing the composition include nasal gels, creams, pastes or ointments with a viscosity of, e.g., from about 10 to about 3000 cps, or from about 2500 to 6500 cps, or greater, which may provide a more sustained contact with the nasal mucosal surfaces. Such carrier viscous formulations may be based upon, simply by way of example, polymeric carriers such as alkylcelluloses and/or other biocompatible carriers of high viscosity well known to the art (see e.g., Remington's, cited supra). The carrier containing the composition may also be soaked into a fabric material, such as gauze, that can be applied to the nasal mucosal surfaces to allow for active substances in the isolated fraction to penetrate to the mucosa.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation.

Further, for nasal administration of solutions or suspensions of the composition, various devices are available in the art for the generation of drops, droplets and sprays. For example, solutions comprising the isolated fraction can be administered into the nasal passages by means of a simple dropper (or pipet) that includes a glass, plastic or metal dispensing tube from which the contents are expelled drop by drop by means of air pressure provided by a manually powered pump, e.g., a flexible rubber bulb, attached to one end. Fine droplets and sprays can be provided by a manual or electrically powered intranasal pump dispenser or squeeze bottle as well known to the art, e.g., that is designed to blow a mixture of air and fine droplets into the nasal passages.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, for example, about 0.05 to about 35 mg/kg/day, in single or divided doses. For example a dosage is about 0.0005 to about 2.5 g/day. For example, a dosage is about 0.0005 to about 1 g/day in single or divided dosages. In some instances, dosage levels below the lower limit of the aforesaid range may be more than adequate, while in other cases still larger doses may be employed without causing any harmful side effect, provided that such larger doses are first divided into several small doses for administration throughout the day.

For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

The size of the dose for therapeutic or prophylactic purposes of a compound of the invention will naturally vary according to the nature and severity of the conditions, the age and sex of the animal or patient and the route of administration, according to well known principles of medicine. It will be understood that the specific dosage level and frequency of dosage for any particular subject may be varied and will depend upon a variety of factors including the activity of the specific compound of the invention, the species, age, body weight, general health, sex and diet of the subject, the mode and time of administration, rate of excretion, drug combination, and severity of the particular condition, but can nevertheless be routinely determined by one skilled in the art.

A compound of the invention or salt thereof, is in some aspects administered to a subject in combination (e.g., in the same formulation or in separate formulations) with another therapeutic agent ("combination therapy"). The compound of the invention is administered in admixture with another therapeutic agent or is administered in a separate formulation. When administered in separate formulations, a compound of the invention and another therapeutic agent is administered substantially simultaneously or sequentially. In one aspect, a compound of the invention is administered to a subject in combination with another therapeutic agent for treating a condition or disease. In one aspect, a compound of the invention is administered to a subject in combination with another therapeutic agent for preventing a condition or disease. In one aspect, a compound of the invention is administered to a subject in combination with a vaccine for preventing a condition or disease. In one aspect, a compound of the invention is administered to a subject in combination with an infectious disease vaccine. In one aspect, a compound of the invention is administered to a subject in combination with a cancer vaccine.

A compound of the invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

A compound of the invention may also be helpful in individuals having compromised immune function. For example, a compound of the invention may be used for treating or preventing the opportunistic infections and tumors that occur after suppression of cell mediated immunity in, for example, transplant patients, cancer patients and HIV patients.

Such combination treatment may involve, in addition to a compound of the invention, conventional surgery or radiotherapy or chemotherapy. Such chemotherapy may include one or more of the following categories of anti-tumor agents: (i) antiproliferative/anti-neoplastic drugs and combinations thereof; (ii) cytostatic agents; (iii) agents which inhibit cancer cell invasion; (iv) inhibitors of growth factor function; (v) antiangiogenic agents; (vi) vascular damaging agents; (vii) antisense therapies; (viii) gene therapy approaches; (ix) interferon; and (x) immunotherapy approaches.

Therapeutic agents for treating or preventing respiratory diseases which may be administered in combination with a compound of the invention in a subject method include, but are not limited to beta adrenergics which include bronchodilators including albuterol, isoproterenol sulfate, metaproterenol sulfate, terbutaline sulfate, pirbuterol acetate and sahneterol formotorol; steroids including beclomethasone dipropionate, flunisolide, fluticasone, budesonide and triamcinolone acetonide. Anti-inflammatory drugs used in connection with the treatment or preventing of respiratory diseases include steroids such as beclomethasone dipropionate, triamcinolone acetonide, flunisolide and fluticasone. Other anti-inflammatory drugs include cromoglycates such as cromolyn sodium. Other respiratory drugs which would qualify as bronchodilators include anticholenergics including ipratropium bromide. Anti-histamines include, but are not limited to, diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine. Particular anti-histamines include rhinolast (Astelin®), claratyne (Claritin®), claratyne D (Claritin D®), telfast (Allegra®), Zyrtec®, and beconase.

In some embodiments, a compound of the invention is administered as a combination therapy with interferon-gamma (IFN-gamma), a corticosteroid such as prednisone, prednisolone, methyl prednisolone, hydrocortisone, cortisone, dexamethasone, betamethasone, etc., or a combination thereof, for the treatment or preventing of interstitial lung disease, e.g., idiopathic pulmonary fibrosis.

In some embodiments, a compound of the invention is administered in combination therapy with a known therapeutic agent used in the treatment of cystic fibrosis ("CF"). Therapeutic agents used in the treatment of CF include, but are not limited to, antibiotics; anti-inflammatory agents; DNAse (e.g., recombinant human DNAse; pulmozyme; dornase alfa); mucolytic agents (e.g., N-acetylcysteine; Mucomyst™; Mucosil™); decongestants; bronchodilators (e.g., theophylline; ipratropium bromide); and the like.

In some embodiments, a compound of the invention is administered prophylactically for the prevention of cardiovascular disease, e.g., atherosclerosis.

In another embodiment of the invention, an article of manufacture, or "kit", containing materials useful for the treatment or prevention of the diseases described above is provided.

In one embodiment, the kit comprises a container comprising a composition of the invention, or pharmaceutically acceptable salt thereof. In one embodiment, the invention provides a kit for treating or preventing a TLR7- and/or TLR8-mediated disorder. In another embodiment, the invention provides a kit for a condition or disorder treatable by selective modulation of the immune system in a subject. The kit may further comprise a label or package insert on or associated with the container. Suitable containers include, for example, bottles, vials, syringes, blister pack, etc. The container may be formed from a variety of materials such as glass or plastic. The container holds a compound of the invention or a pharmaceutical formulation thereof in an amount effective for treating or preventing the condition, and may have a sterile access port (for example, the container may be an intravenous solution bag or a vial having a stopper pierceable by a hypodermic injection needle). The label or package insert indicates that the composition is used for treating or preventing the condition of choice. In one embodiment, the label or package inserts indicates that the composition comprising a compound of the invention can be used, for example, to treat or prevent a disorder treatable by modulation of TLR7- and/or TLR8-mediated cellular activities. The label or package insert may also indicate that the composition can be used to treat or prevent other disorders. Alternatively, or additionally, the kit may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of the invention and, if present, the second pharmaceutical formulation. For example, if the kit comprises a first composition comprising a compound of the invention and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of the invention, such as tablets or capsules. Such a kit includes, for example, a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, the kit may comprise (a) a first container with a compound of the invention contained therein; and optionally (b) a second container with a second pharmaceutical formulation contained therein, wherein the second pharmaceutical formulation comprises a second compound which may be effective in treating or preventing a condition or disorder by selective modulation of TLR7- and/or TLR8-mediated cellular activities. Alternatively, or additionally, the kit may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a pharmaceutical formulation of a compound of the invention and a second formulation comprising a second therapeutic agent, the kit may comprise a container for containing the separate formulations, such as a divided bottle or a divided foil packet; however, the separate compositions may also be contained within a single, undivided container. Typically, the kit comprises directions for the administration of the separate components. The kit form is particularly advantageous when the separate components are administered in different dosage forms (e.g., oral and parenteral), are administered at different dosage intervals, or when titration of the individual components of the combination is desired by the prescribing physician.

Activity of the compounds can be assessed according to procedures described in, e.g., Gorden et al., *Journal of Immunology* 177, pp. 8164-8170 (2006) and Zhu et al., *Molecular Immunology*, vol. 45 (11), pp. 3238-3242 (2008).

$MC_{50}$ values for TLR8 activity are, for example, as shown below:

| Compound | Structure | TLR8 ($MC_{50}$) |
|---|---|---|
| 183 | 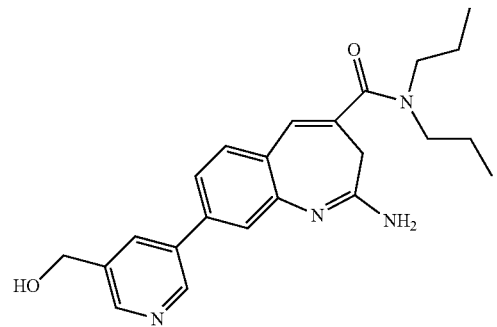 [SMILES: CCCN(CCC)C(=O)C1=Cc2ccc(-c3cncc(CO)c3)cc2N=C(N)C1] | 8 nM |
| 214 | 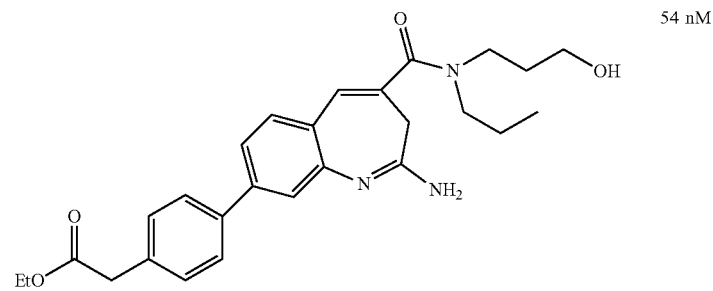 | 54 nM |

| Compound | Structure | TLR8 (MC$_{50}$) |
|---|---|---|
| 222 | 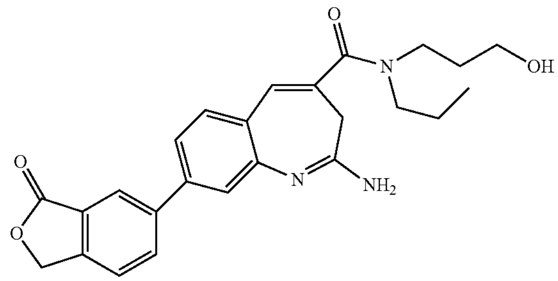 [SMILES: CCCN(CCCO)C(=O)C1=Cc2ccc(-c3ccc4c(c3)C(=O)OC4)cc2N=C(N)C1] | 33 nM |
| 223 | 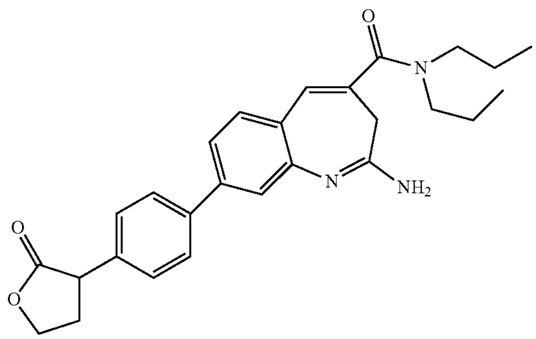 [SMILES: CCCN(CCC)C(=O)C1=Cc2ccc(-c3ccc(C4CCOC4=O)cc3)cc2N=C(N)C1] | 195 nM |
| 224 | 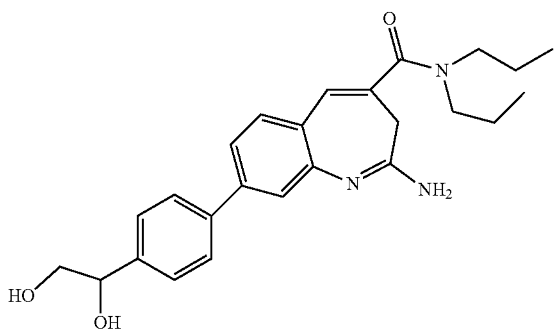 [SMILES: CCCN(CCC)C(=O)C1=Cc2ccc(-c3ccc(C(O)CO)cc3)cc2N=C(N)C1] | 363 nM |

MC$_{50}$ values for TLR7 activity are, for example, as shown below:

| Compound | Structure | TLR7 (MC$_{50}$) |
|---|---|---|
| 222 | 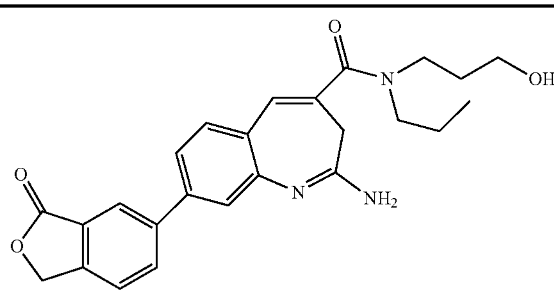 | 358 nM |

EXAMPLES

In order to illustrate the invention, the following examples are included. However, it is to be understood that these examples do not limit the invention and are only meant to suggest a method of practicing the invention. Persons skilled in the art will recognize that chemical reactions described may be readily adapted to prepare a number of other compounds of the invention, and alternative methods for preparing the compounds of this invention are also deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, Acros, TCI, Alfa Aesar or Maybridge, and were used without further purification unless otherwise indicated.

In the examples described below, the term "Example ###" refers to "Compound ###". For example, Example 113 is directed to Compound 113 and/or synthetic procedures relating to Compound 113.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heated dried.

Microwave reactions were performed on the Biotage Initiator system.

Column chromatography was done on a Biotage system or Isolute Flash Si SPE column (manufacturer: Biotage AB) having a silica gel column or on a silica SepPak cartridge (Waters). $^1$H and $^{19}$F NMR spectra were recorded on a Varian instrument operating at 400 MHz and 376 MHz, respectively. $^1$H-NMR spectra were obtained as CDCl$_3$ or d$_6$-DMSO solutions (reported in ppm), using chloroform (7.26 ppm) or tetramethylsilane (0 ppm) as the reference standards. When peak multiplicities are reported, the following abbreviations are used: s (singlet), d (doublet), t (triplet), q (quartet), br (broadened), dd (doublet of doublets), dt (double of triplets), m (multiplet).

Example 1

Synthetic Procedures

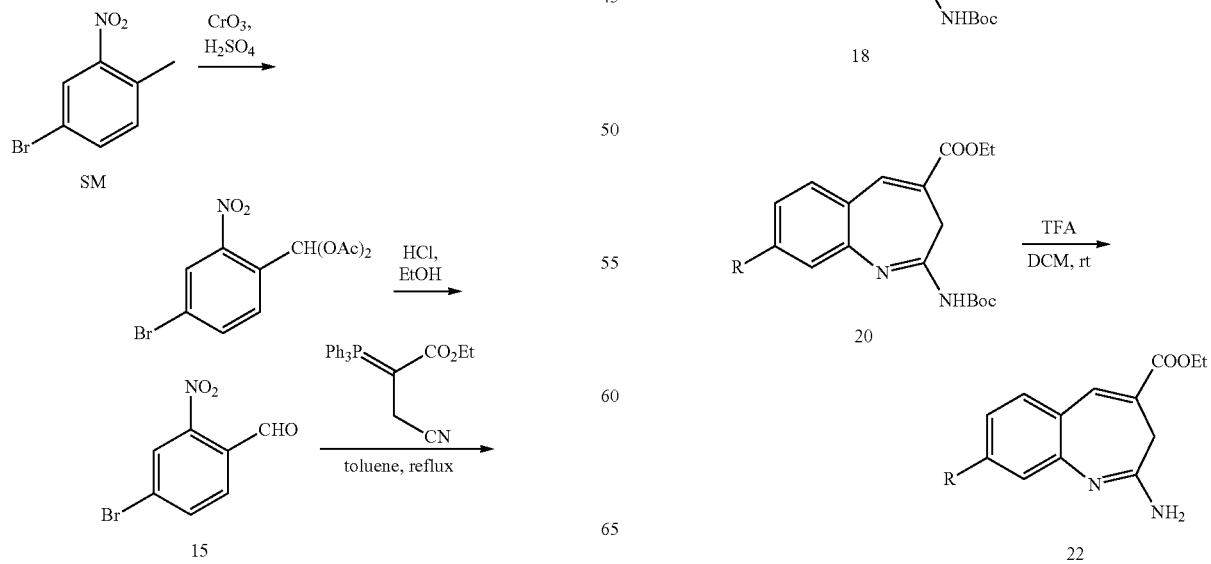

1. Synthesis of Compound 15

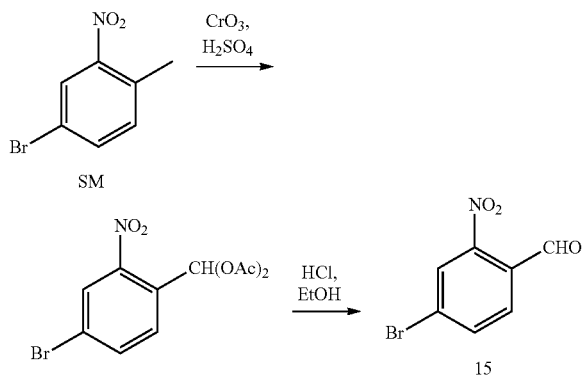

In a three-necked flask provided with a mechanical stirrer, dropping funnel, and thermometer, surrounded by an ice-salt bath, are placed 400 mL of acetic anhydride and 50 g (0.23 mole) of 4-bromo-1-methyl-2-nitrobenzene. To this solution is added slowly with stirring 54 mL of concentrated sulfuric acid. When the mixture has cooled to 0° C., a solution of 64 g of chromium trioxide in 360 mL of acetic anhydride is added slowly with stirring; at such a rate that the temperature does not exceed 10 and stirring is continued for 2 hours at 5-10° C. in an ice-water bath after the addition is complete. The contents of the flask are poured into the mixture of ice and water. The solid was filtered and washed with water until the washings are colorless. The product is suspended in 300 mL of 2% aqueous sodium carbonate solution and stirred. After thorough mixing, the solid was filtered and washed with water and dried.

A suspension of the diacetate in a mixture of 272 mL of concentrated hydrochloric acid, 250 ml, of water, and 80 mL of ethanol was stirred and refluxed for 45 minutes. The mixture was then cooled to RT and the solid was filtered and washed with water. The crude product is purified by column (22 g, 42%).

2. Synthesis of Compound 16

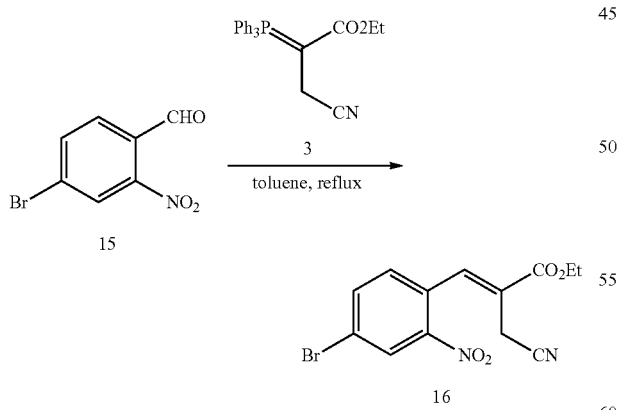

A mixture of the aldehyde (0.73 g, 3.17 mmol) and the ylide (1.42 g, 3.65 mmol) in toluene (8 mL) was gently refluxed for 2.5 hrs. The reaction mixture was cooled to room temperature and concentrated under reduced pressure to give the crude material that was used directly without further purification.

3. Synthesis of Compound 17 and 17B

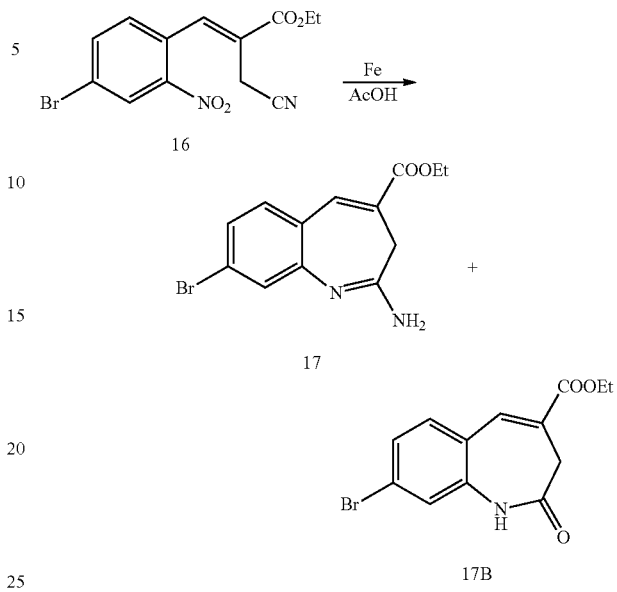

To a solution of the crude nitrile in AcOH (25 ml) was added iron (1.15 g, 20.61 mmol) at room temperature. The resulting mixture was heated at 85° C. for 4 h. The reaction mixture was cooled to room temperature and diluted with $CH_2Cl_2$ (8 mL). The resulting mixture was filtered, the solids were washed with $CH_2Cl_2$. The filtrate was concentrated under reduced pressure to give viscous oil. To the crude material was added $CH_2Cl_2$ (8 mL). aq. $Na_2CO_3$ followed by water was slowly added with stirring until its pH=9-10. The mixture was filtered off and washed with $CH_2Cl_2$. The organic layer was separated. The aqueous layer was extracted with $CH_2Cl_2$. The organic layer was separated. The aqueous layer was extracted with $CH_2Cl_2$. The combined organic layers were washed with brine, dried over $Na_2SO_4$, the mixture was concentrated under reduced pressure to give the crude material that was purified by silica gel flash column chromatography to afford 0.329 g (33% for two steps) of the desired product was obtained based on $^1$H-NMR.

4. Synthesis of Compound 18

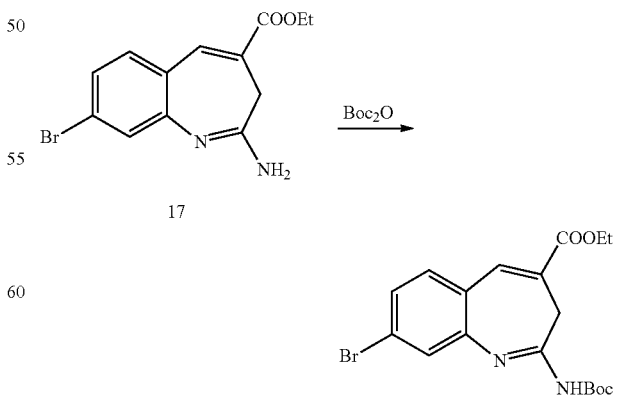

To the benzazepine (2.34 g, 7.57 mmol) in DCM (25 mL) was added Boc₂O (2.06 g, 9.46 mmol) at room temperature. The reaction mixture was stirred for 20 hrs. The resulting mixture was consecutively washed with saturated aq. NaHCO₃ and brine. The organic layer was separated and dried over Na₂SO₄, filtered, and concentrated under reduced pressure to give the crude product that was purified by silica gel flash column chromatography (10% EtOAc in hexanes) to afford 1.64 g (52.9%) of the desired product.

5. Synthesis of Species

Example 113

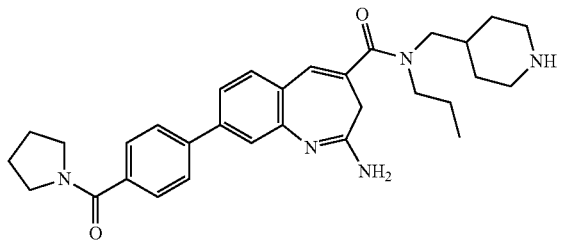 [SMILES: CCCN(CC1CCNCC1)C(=O)C1=Cc2ccc(-c3ccc(C(=O)N4CCCC4)cc3)cc2N=C(N)C1]

(1E,4E)-2-amino-N-(piperidin-4-ylmethyl)-N-propyl-8-(4-(pyrrolidine-1-carbonyl)phenyl)-3H-benzo[b]azepine-4-carboxamide Step A: Preparation of tert-butyl 4-((benzyloxycarbonylamino)methyl)piperidine-1-carboxylate tert-Butyl 4-(aminomethyl)piperidine-1-carboxylate (0.611 g, 2.851 mmol) and diisopropylethylamine (0.479 g, 3.706 mmol) were dissolved in 30 mls of dry dichloromethane. To this mixture was added benzyl chloroformate (0.552 g, 3.136 mmol) and the mixture was stirred at room temperature for 2 hours. The mixture was then diluted with 50 mls of dichloromethane, washed once with 1N aqueous HCl, one with saturated sodium bicarbonate solution, dried over sodium sulfate and concentrated under reduced pressure to 950 mgs (96%) of the title compound and used directly without further purification.

Step B: Preparation of tert-butyl 4-(((benzyloxycarbonyl)(propyl)amino)methyl)piperidine-1-carboxylate tert-Butyl 4-((benzyloxycarbonylamino)methyl)piperidine-1-carboxylate (0.950 g, 2.726 mmol) was dissolved in dry DMF (25 mls). To this was added sodium hydride (0.164 g, 4.090 mmole, 60% dispersion in mineral oil) and the reaction mixture was stirred at room temperature for 30 minutes. Propyl iodide (0.695 g, 4.090 mmole) was then added and the mixture stirred at room temperature for 16 hours, then diluted with brine (200 mls), extracted twice with EtOAc, extracts washed twice with brine, dried over sodium sulfate and concentrated under reduced pressure. The resulting oil was purified by flash chromatography (100 g Biotage Snap cartridge, 30% EtOAc/Hexanes) to give 0.280 g (26%) of the title compound.

Step C: Preparation of tert-butyl 4-((propylamino)methyl)piperidine-1-carboxylate To a solution of tert-butyl 4-(((benzyloxycarbonyl)(propyl)amino)methyl)piperidine-1-carboxylate (0.280 g, 0.717 mmol) in 7 mls of methanol was added palladium(II) hydroxide (0.200 g, 20 wt % Pd(OH)₂ on carbon, Degussa type). This mixture was hydrogenated under a balloon of hydrogen for 1.5 hours, then filtered through GF/F filter paper and the filtrate concentrated. Obtained 0.169 g (92%) of the title compound and used directly without further purification.

Step D: Preparation of (1E,4E)-2-amino-N-(piperidin-4-ylmethyl)-N-propyl-8-(4-(pyrrolidine-1-carbonyl)phenyl)-3H-benzo[b]azepine-4-carboxamide The title compound was prepared by these procedures using (1E,4E)-2-(tert-butoxycarbonylamino)-8-(4-(pyrrolidine-1-carbonyl)phenyl)-3H-benzo[b]azepine-4-carboxylic acid and tert-butyl 4-((propylamino)methyl)piperidine-1-carboxylate. Preparation of tert-butyl (1E,4E)-4-(propylcarbamoyl)-8-(4-(pyrrolidine-1-carbonyl)phenyl)-3H-benzo[b]azepin-2-ylcarbamate: A mixture of (1E,4E)-2-(tert-butoxycarbonylamino)-8-(4-(pyrrolidine-1-carbonyl)phenyl)-3H-benzo[b]azepine-4-carboxylic acid (200 mg, 0.42 mmol), HOBt (114 mg, 0.84 mmol), and EDCI (161 mg, 0.84 mmol) in DMF (5 mL) was stirred for 1 h at room temperature. To this mixture was added triethylamine (0.12 mL, 0.84 mmol) and propan-1-amine (0.043 mL, 0.53 mmol) at room temperature. The resulting solution was stirred for additional 2 h. The reaction mixture was diluted with EtOAc (5 mL) and washed with saturated aq NH₄Cl. The aqueous layer was separated and extracted with EtOAc (3×5 mL). The combined organic layers were washed with brine (5 mL), saturated aq NaHCO₃ (5 mL), and brine (5 mL). The organic layer was dried over MgSO₄, filtered, and concentrated under reduced pressure to give the crude tert-butyl (1E,4E)-4-(propylcarbamoyl)-8-(4-(pyrrolidine-1-carbonyl)phenyl)-3H-benzo[b]azepin-2-ylcarbamate that was used directly without further purification. Preparation of (1E,4E)-2-amino-N-propyl-8-(4-(pyrrolidine-1-carbonyl)phenyl)-3H-benzo[b]azepine-4-carboxamide: To a solution of tert-butyl (1E,4E)-4-(propylcarbamoyl)-8-(4-(pyrrolidine-1-carbonyl)phenyl)-3H-benzo[b]azepin-2-ylcarbamate (450 mg, 0.87 mmol) in CH₂Cl₂ (5 mL) was added 2,2,2-trifluoroacetic acid (1.36 mL, 17.4 mmol) at 0° C. The reaction mixture was warmed to room temperature and stirred for 2 h. The reaction mixture was concentrated under reduced pressure to give the crude material that was diluted with CH₂Cl₂ (10 mL) and saturated aq NaHCO₃ (15 mL) again. The resulting mixture was stirred for 30 min at room temperature. The aqueous layer was separated and extracted with CH₂Cl₂ (1×10 mL). The combined organic layers were washed with saturated aq NaHCO₃ (2×10 mL) and brine (1×10 mL), dried over MgSO₄, filtered, and concentrated under reduced pressure to give the crude material again that was purified by silica gel flash column chromatography (1 to 5% MeOH in CH₂Cl₂, gradient). m/z (APCI-pos) M+1=514.3.

The following example, 116, was prepared by these procedures using (1E,4E)-2-(tert-butoxycarbonylamino)-8-(4-(pyrrolidine-1-carbonyl)phenyl)-3H-benzo[b]azepine-4-carboxylic acid and the appropriate amines (2-methyl-1-(propylamino)propan-2-ol was prepared by the procedure reported in J. Am. Chem. Soc. 1939, 61, 3562) or the hydroxylamine. Preparation of tert-butyl (1E,4E)-4-(propylcarbamoyl)-8-(4-(pyrrolidine-1-carbonyl)phenyl)-3H-benzo[b]azepin-2-ylcarbamate: A mixture of (1E,4E)-2-(tert-butoxycarbonylamino)-8-(4-(pyrrolidine-1-carbonyl)phenyl)-3H-benzo[b]azepine-4-carboxylic acid (200 mg, 0.42 mmol), HOBt (114 mg, 0.84 mmol), and EDCI (161 mg, 0.84 mmol) in DMF (5 mL) was stirred for 1 h at room temperature. To this mixture was added triethylamine (0.12 mL, 0.84 mmol) and propan-1-amine (0.043 mL, 0.53 mmol) at room temperature. The resulting solution was stirred for additional 2 h. The reaction mixture was diluted with EtOAc (5 mL) and washed with saturated aq NH₄Cl. The aqueous layer was separated and extracted with EtOAc (3×5 mL). The combined organic layers were washed with brine (5 mL), saturated aq NaHCO₃ (5 mL), and brine (5 mL). The organic layer was dried over MgSO₄, filtered, and concentrated under reduced pressure to give the crude tert-butyl (1E,4E)-4-(propylcarbamoyl)-8-(4-(pyrrolidine-1-carbonyl)phenyl)-3H-benzo[b]azepin-2-ylcarbamate that was used directly without further purification. Preparation of (1E,4E)-2-amino-N-propyl-8-(4-(pyrrolidine-1-carbonyl) phenyl)-3H-benzo[b]azepine-4-carboxamide: To a solution of tert-butyl (1E,4E)-4-(propylcarbamoyl)-8-(4-(pyrrolidine-1-carbonyl)phenyl)-3H-benzo[b]azepin-2-ylcarbamate (450 mg, 0.87 mmol) in CH₂Cl₂ (5 mL) was added 2,2,2-trifluoroacetic acid (1.36 mL, 17.4 mmol) at 0° C. The reaction mixture was warmed to room temperature and stirred for 2 h. The reaction mixture was concentrated under reduced pressure to give the crude material that was diluted with CH₂Cl₂ (10 mL) and saturated aq NaHCO₃ (15 mL) again. The resulting mixture was stirred for 30 min at room temperature. The aqueous layer was separated and extracted with CH₂Cl₂ (1×10 mL). The combined organic layers were washed with saturated aq NaHCO₃ (2×10 mL) and brine (1×10 mL), dried over MgSO₄, filtered, and concentrated under reduced pressure to give the crude material again that was purified by silica gel flash column chromatography (1 to 5% MeOH in CH₂Cl₂, gradient).

Example 116

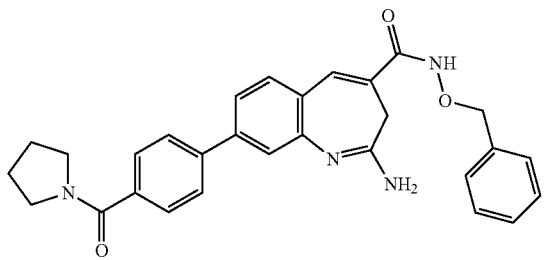 [SMILES: NC1=Nc2cc(-c3ccc(C(=O)N4CCCC4)cc3)ccc2C=C(C(=O)NOCc2ccccc2)C1]

(1E,4E)-2-amino-N-(benzyloxy)-8-(4-(pyrrolidine-1-carbonyl)phenyl)-3H-benzo[b]azepine-4-carboxamide ¹H-NMR (400 MHz, CDCl₃) δ 11.59 (br s, 1H), 7.74-7.78 (m, 2H), 7.61-7.65 (m, 2H), 7.33-7.53 (m, 8H), 4.91 (s, 2H), 3.40-3.53 (m, 4H), 3.03 (s, 2H), 1.80-1.92 (m, 4H); m/z (APCI-pos) M+1=481.2.

Example 118

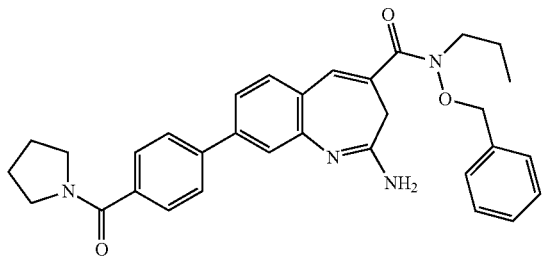 [SMILES: CCCN(OCc1ccccc1)C(=O)C1=Cc2ccc(-c3ccc(C(=O)N4CCCC4)cc3)cc2N=C(N)C1]

(1E,4E)-2-amino-N-(benzyloxy)-N-propyl-8-(4-(pyrrolidine-1-carbonyl)phenyl)-3H-benzo[b]azepine-4-carboxamide Step A: Preparation of O-benzyl-N-propylhydroxylamine To a solution of propan-1-ol (6.25 mL, 83.2 mmol) and 2,6-dimethylpyridine (11.6 mL, 99.8 mmol) in CH₂Cl₂ (500 mL) under a nitrogen atmosphere at −78° C. was added dropwise trifluoromethanesulfonic anhydride (14.0 mL, 83.2 mmol). After stirring for 30 min at −78° C., a solution of O-benzylhydroxylamine (10.7 ml, 91.5 mmol) in CH₂Cl₂ (10 mL) was added dropwise. The resulting mixture was stirred at −78° C. for 1 h, then warmed to room temperature, and stirred for additional 2 h. The reaction mixture was diluted with ice water (250 mL) and the organic layer was separated, washed with saturated aq. NaHCO₃ (100 mL) and brine (100 mL). The aqueous layers were extracted again with EtOAc (1×200 mL). The combined organic layers were dried over MgSO₄, filtered, and concentrated under reduced pressure to give the crude material that was purified by silica gel flash column chromatography (CH₂Cl₂). To the fraction containing product and 2,6-dimethylpyridine was added 2 M aq KOH (100 mL), that was then washed with MTBE. The aqueous layer was then brought to a pH of ~5 with 1 M aq HCl and then extracted with MTBE (3×50 mL). The combined organic layers were dried over MgSO₄, filtered, and concentrated under reduced pressure to afford 11.2 g (75%) of O-benzyl-N-propylhydroxylamine.

Step B: Preparation of tert-butyl (1E,4E)-4-(benzyloxy(propyl)carbamoyl)-8-(4-(pyrrolidine-1-carbonyl)phenyl)-3H-benzo[b]azepin-2-ylcarbamate The title compound was prepared by these procedures using (1E,4E)-2-(tert-butoxycarbonylamino)-8-(4-(pyrrolidine-1-carbonyl)phenyl)-3H-benzo[b]azepine-4-carboxylic acid and O-benzyl-N-propylhydroxylamine. Preparation of tert-butyl (1E,4E)-4-(propylcarbamoyl)-8-(4-(pyrrolidine-1-carbonyl)phenyl)-3H-benzo[b]azepin-2-ylcarbamate: A mixture of (1E,4E)-2-(tert-butoxycarbonylamino)-8-(4-(pyrrolidine-1-carbonyl)phenyl)-3H-benzo[b]azepine-4-carboxylic acid (200 mg, 0.42 mmol), HOBt (114 mg, 0.84 mmol), and EDCI (161 mg, 0.84 mmol) in DMF (5 mL) was stirred for 1 h at room temperature. To this mixture was added triethylamine (0.12 mL, 0.84 mmol) and propan-1-amine (0.043 mL, 0.53 mmol) at room temperature. The resulting solution was stirred for additional 2 h. The reaction mixture was diluted with EtOAc (5 mL) and washed with saturated aq NH₄Cl. The aqueous layer was separated and extracted with EtOAc (3×5 mL). The combined organic layers were washed with brine (5 mL), saturated aq NaHCO₃ (5 mL), and brine (5 mL). The organic layer was dried over MgSO₄, filtered, and concentrated under reduced pressure to give the crude tert-butyl (1E,4E)-4-(propylcarbamoyl)-8-(4-(pyrrolidine-1-carbonyl)phenyl)-3H-benzo[b]azepin-2-ylcarbamate that was used directly without further purification. Preparation of (1E,4E)-2-amino-N-propyl-8-(4-(pyrrolidine-1-carbonyl)phenyl)-3H-benzo[b]azepine-4-carboxamide: To a solution of tert-butyl (1E,4E)-4-(propylcarbamoyl)-8-(4-(pyrrolidine-1-carbonyl)phenyl)-3H-benzo[b]azepin-2-ylcarbamate (450 mg, 0.87 mmol) in CH₂Cl₂ (5 mL) was added 2,2,2-trifluoroacetic acid (1.36 mL, 17.4 mmol) at 0° C. The reaction mixture was warmed to room temperature and stirred for 2 h. The reaction mixture was concentrated under reduced pressure to give the crude material that was diluted with CH$_2$Cl$_2$ (10 mL) and saturated aq NaHCO$_3$ (15 mL) again. The resulting mixture was stirred for 30 min at room temperature. The aqueous layer was separated and extracted with CH$_2$Cl$_2$ (1×10 mL). The combined organic layers were washed with saturated aq NaHCO$_3$ (2×10 mL) and brine (1×10 mL), dried over MgSO$_4$, filtered, and concentrated under reduced pressure to give the crude material again that was purified by silica gel flash column chromatography (1 to 5% MeOH in CH$_2$Cl$_2$, gradient). $^1$H-NMR (400 MHz, CDCl$_3$) d 7.67-7.71 (m, 2H), 7.60-7.63 (m, 2H), 7.53-7.55 (m, 1H), 7.29-7.39 (m, 8H), 4.84 (s, 2H), 3.74-3.81 (m, 2H), 3.62-3.71 (m, 2H), 3.48-3.54 (m, 2H), 2.82 (s, 2H), 1.87-2.01 (m, 4H), 1.74-1.84 (m, 2H), 0.96-1.02 (m, 3H); m/z (APCI-pos) M+1=523.2.

Example 148

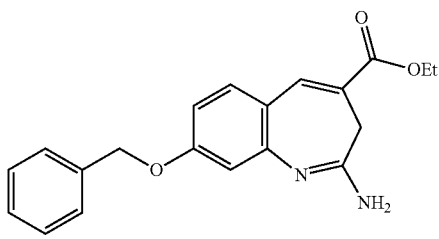 [SMILES: CCOC(=O)C1=Cc2ccc(OCc3ccccc3)cc2N=C(N)C1]

(1E,4E)-ethyl 2-amino-8-(benzyloxy)-3H-benzo[b]azepine-4-carboxylate

The title compound was prepared by these procedures using 4-(benzyloxy)-1-methyl-2-nitrobenzene. Preparation of (E)-1-(4-bromo-2-nitrostyryl)pyrrolidine: A solution of 4-bromo-2-nitrotoluene (100 g, 463 mmol), pyrrolidine (46.2 mL, 565 mmol), and N,N-dimethylformamide dimethylacetal (75.6 mL, 565 mmol) was refluxed for 4 hours at 110° C. The reaction mixture was cooled to room temperature and concentrated under reduced pressure to give the crude (E)-1-(4-bromo-2-nitrostyryl)pyrrolidine that was used directly without further purification. Preparation of 4-bromo-2-nitrobenzaldehyde: To a solution of sodium periodate (298 g, 1.40 mol) in THF-H$_2$O (4 L, 1:1) at 0° C. was added (E)-1-(4-bromo-2-nitrostyryl)pyrrolidine (138 g, 464 mmol). The mixture was stirred for 15 h and then filtered to remove solid precipitates. The aqueous layer from the filtrate was separated and extracted with EtOAc (4×200 mL). The combined organic layers were washed with H$_2$O (2×200 mL), dried over MgSO$_4$, filtered, and concentrated under reduced pressure to give the crude product that was purified by silica gel flash column chromatography (5% EtOAc in hexanes). Preparation of (E)-ethyl 2-(cyanomethyl)-3-(3-nitro-4'-(pyrrolidine-1-carbonyl)biphenyl-4-yl)acrylate: A mixture of 3-nitro-4'-(pyrrolidine-1-carbonyl)biphenyl-4-carbaldehyde (20.0 g, 61.7 mmol) and α-cyanomethylcarboethoxyethylidene triphenylphosphorane (26.3 g, 67.8 mmol) in toluene (200 mL) was gently refluxed for 2.5 h. The reaction mixture was cooled to room temperature and concentrated under reduced pressure to give the crude (E)-ethyl 2-(cyanomethyl)-3-(3-nitro-4'-(pyrrolidine-1-carbonyl)biphenyl-4-yl)acrylate that was used directly without further purification. Preparation of (1E,4E)-ethyl 2-amino-8-(4-(pyrrolidine-1-carbonyl)phenyl)-3H-benzo[b]azepine-4-carboxylate: To a solution of the crude (E)-ethyl 2-(cyanomethyl)-3-(3-nitro-4'-(pyrrolidine-1-car-bonyl)biphenyl-4-yl)acrylate in AcOH (650 mL) was added iron (29.1 g, 521 mmol) at room temperature. The resulting mixture was heated at 85° C. for 4 h. The reaction mixture was cooled to room temperature and diluted with CH$_2$Cl$_2$ (250 mL). The solids were filtered off and washed with CH$_2$Cl$_2$ (200 mL). The filtrate was concentrated under reduced pressure to give the crude material that was diluted with CH$_2$Cl$_2$ (250 mL) again. To this mixture was slowly added saturated aq Na$_2$CO$_3$ (~330 mL) with vigorous stirring until it became basic (pH ~9-10). The resulting mixture was filtered off and washed with CH$_2$Cl$_2$ (~250 mL). The aqueous layer was separated and extracted with CH$_2$Cl$_2$ (2×150 mL). The combined organic layers were washed with brine, dried over MgSO$_4$, and filtered to give the crude material that was diluted with EtOAc (70 mL). The mixture was kept for 16 h at room temperature. The suspension was filtered. The solids filtered off were washed with EtOAc (100 mL) to give the crude product that was washed with a small amount of CH$_2$Cl$_2$.

Example 175

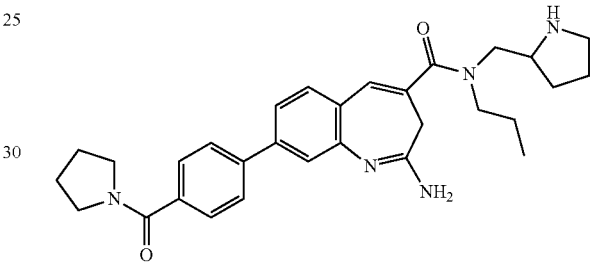

(1E,4E)-2-amino-N-propyl-N-(pyrrolidin-2-ylmethyl)-8-(4-(pyrrolidine-1-carbonyl)phenyl)-3H-benzo[b]azepine-4-carboxamide Step A: Preparation of pyrrolidin-2-ylmethanol To a solution of DL-proline (100 g, 869 mmol) in MeOH (1500 mL) was slowly added SOCl$_2$ at 0° C. The reaction mixture was stirred at room temperature overnight. The reaction mixture was concentrated under reduced pressure to give the crude material that was dissolved in THF (1700 mL) again. To this mixture was added portionwise LiAlH$_4$ (132 g, 3.47 mol) at 0° C. The resulting mixture was heated at 60° C. overnight. The excess LiAlH$_4$ was quenched with KOH. The reaction mixture was filtered and the solid was washed with MeOH (1000 mL). The combined organic layers were dried, filtered, and concentrated under reduced pressure to give the crude material that was purified by distillation to afford 15.8 g (18%) of pyrrolidin-2-ylmethanol.

Step B: Preparation of tert-butyl 2-(hydroxymethyl)pyrrolidine-1-carboxylate

To a solution of pyrrolidin-2-ylmethanol (505 mg, 4.99 mmol) and TEA (1.0 g, 9.9 mmol) in CH$_2$Cl$_2$ (5 mL) was added a solution of Boc$_2$O (1.31 g, 6 mmol) in CH$_2$Cl$_2$ (10 mL). The reaction mixture was stirred for 3 h at room temperature. The reaction mixture was quenched with water (100 mL) and extracted with CH$_2$Cl$_2$. The organic layer was washed with brine, dried over Na$_2$SO$_4$, filtered, and concentrated under reduced pressure to give the crude material that was purified by silica gel flash column chromatography (MeOH:CH$_2$Cl$_2$=1:100) to afford 14.2 g (48%) of tert-butyl 2-(hydroxymethyl)pyrrolidine-1-carboxylate. LCMS ESI (+) m/z 202 (M+1) detected.

Step C: Preparation of tert-butyl 2-((methylsulfonyloxy)methyl)pyrrolidine-1-carboxylate To a solution of tert-butyl 2-(hydroxymethyl)pyrrolidine-1-carboxylate (1.0 g, 5.0 mmol) and TEA (1.0 g, 9.9 mmol) in CH$_2$Cl$_2$ (40 mL) was slowly added MsCl (0.63 g, 5.5 mmol). The reaction mixture was stirred for 30 min at −20° C. and then water (60 mL) was added. The aqueous phase was separated and extracted with CH$_2$Cl$_2$. The combined organic layers were washed with brine, dried over Na$_2$SO$_4$, filtered, and concentrated under reduced pressure to afford the crude tert-butyl 2-((methylsulfonyloxy)methyl)pyrrolidine-1-carboxylate that was used directly without further purification.

Step D: Preparation of tert-butyl 2-((propylamino)methyl)pyrrolidine-1-carboxylate A solution of tert-butyl 2-((methylsulfonyloxy)methyl)pyrrolidine-1-carboxylate (5.0 g, 18 mmol) and propan-1-amine (20.0 g, 339 mmol) in toluene (50 mL) was heated at 100° C. overnight. The reaction mixture was cooled to room temperature and concentrated under reduced pressure to afford the crude tert-butyl 2-((propylamino)methyl)pyrrolidine-1-carboxylate that was used directly without further purification. LCMS ESI (+) m/z 243 (M+1) detected.

Step E: Preparation of (1E,4E)-2-amino-N-propyl-N-(pyrrolidin-2-ylmethyl)-8-(4-(pyrrolidine-1-carbonyl)phenyl)-3H-benzo[b]azepine-4-carboxamide The title compound was prepared by these procedures using (1E,4E)-2-(tert-butoxycarbonylamino)-8-(4-(pyrrolidine-1-carbonyl)phenyl)-3H-benzo[b]azepine-4-carboxylic acid and tert-butyl 2-((propylamino)methyl)pyrrolidine-1-carboxylate. Preparation of tert-butyl (1E,4E)-4-(propylcarbamoyl)-8-(4-(pyrrolidine-1-carbonyl)phenyl)-3H-benzo[b]azepin-2-ylcarbamate: A mixture of (1E,4E)-2-(tert-butoxycarbonylamino)-8-(4-(pyrrolidine-1-carbonyl)phenyl)-3H-benzo[b]azepine-4-carboxylic acid (200 mg, 0.42 mmol), HOBt (114 mg, 0.84 mmol), and EDCI (161 mg, 0.84 mmol) in DMF (5 mL) was stirred for 1 h at room temperature. To this mixture was added triethylamine (0.12 mL, 0.84 mmol) and propan-1-amine (0.043 mL, 0.53 mmol) at room temperature. The resulting solution was stirred for additional 2 h. The reaction mixture was diluted with EtOAc (5 mL) and washed with saturated aq NH$_4$Cl. The aqueous layer was separated and extracted with EtOAc (3×5 mL). The combined organic layers were washed with brine (5 mL), saturated aq NaHCO$_3$ (5 mL), and brine (5 mL). The organic layer was dried over MgSO$_4$, filtered, and concentrated under reduced pressure to give the crude tert-butyl (1E,4E)-4-(propylcarbamoyl)-8-(4-(pyrrolidine-1-carbonyl)phenyl)-3H-benzo[b]azepin-2-ylcarbamate that was used directly without further purification. Preparation of (1E,4E)-2-amino-N-(2-amino-2-oxoethyl)-N-propyl-8-(4-(pyrrolidine-1-carbonyl)phenyl)-3H-benzo[b]azepine-4-carboxamide: A solution of the crude tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. To this mixture was added saturated NaHCO$_3$ at 0° C. The aqueous layer was separated and extracted with CH$_2$Cl$_2$. The combined organic layers were dried over Na$_2$SO$_4$, filtered, and concentrated under reduced pressure to give the crude compound that was purified by silica gel flash column chromatography (MeOH:CH$_2$Cl$_2$=1:50).

In this case the product was obtained as HCl salt. MS APCI (+) m/z 536 (M+1) detected; 1H-NMR (400 MHz, CDCl$_3$) d 7.80 (s, 1H), 7.62-7.66 (m, 4H), 7.52 (d, 1H), 7.42 (d, 1H), 6.97 (s, 1H), 4.31 (br s, 1H), 4.08 (br s, 1H), 3.86 (br s, 1H), 3.68 (t, 2H), 3.48 (br s, 5H), 3.32 (m, 3H), 2.17 (br s, 2H), 1.92-1.99 (m, 8H), 0.87 (t, 3H).

Example 177

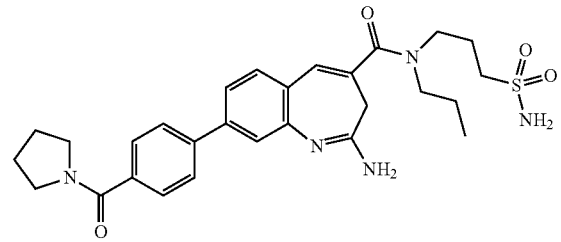 [SMILES: CCCN(CCCS(N)(=O)=O)C(=O)C1=Cc2ccc(-c3ccc(C(=O)N4CCCC4)cc3)cc2N=C(N)C1]

(1E,4E)-2-amino-N-propyl-8-(4-(pyrrolidine-1-carbonyl)phenyl)-N-(3-sulfamoylpropyl)-3H-benzo[b]azepine-4-carboxamide MS APCI (+) m/z 538 (M+1) detected; $^1$H-NMR (400 MHz, CDCl$_3$) δ 7.65 (d, 2H), 7.59 (d, 2H), 7.45 (s, 1H), 7.32 (d, 1H), 7.28 (d, 1H), 6.80 (s, 1H), 3.66 (t, 2H), 3.55 (t, 2H), 3.49 (t, 2H), 3.42 (br s, 2H), 3.14 (br s, 2H), 2.80 (s, 2H), 2.14 (br s, 2H), 1.87-1.99 (m, 4H), 1.59-1.64 (m, 2H), 0.87 (t, 3H).

Example 183

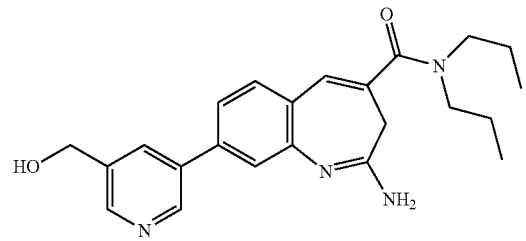 [SMILES: CCCN(CCC)C(=O)C1=Cc2ccc(-c3cncc(CO)c3)cc2N=C(N)C1]

(1E,4E)-2-amino-8-(5-(hydroxymethyl)pyridin-3-yl)-N,N-dipropyl-3H-benzo[b]azepine-4-carboxamide The title compound was prepared by these procedures using tert-butyl (1E,4E)-8-bromo-4-(dipropylcarbamoyl)-3H-benzo[b]azepin-2-ylcarbamate and 3-((tert-butyldimethylsilyloxy)methyl)phenylboronic acid. Preparation of 3-nitro-4'-(pyrrolidine-1-carbonyl)biphenyl-4-carbaldehyde, except in this case Cs$_2$CO$_3$ as a base was used: To a solution of 4-bromo-2-nitrobenzaldehyde (20.2 g, 87.9 mmol), 4-(pyrrolidine-1-carbonyl)phenylboronic acid (21.2 g, 96.7 mmol), and Pd(PPh$_3$)$_4$ (508 mg, 0.440 mmol) in toluene (200 mL) was added EtOH (40 mL) followed by Na$_2$CO$_3$ (70.0 mL, 140 mmol, 2 M aq solution) at room temperature. The resulting mixture was heated at 100° C. for 18 h. The reaction mixture was cooled to room temperature and the organic layer was separated. The aqueous layer was extracted with EtOAc (300 mL). The combined organic layers were washed with brine (500 mL), dried over MgSO$_4$, filtered, and concentrated under reduced pressure to give the crude material that was combined with another batch of the crude material obtained from an additional run in the same reaction scale. The combined crude material was purified by silica gel flash column chromatography (CH$_2$Cl$_2$ to 1% MeOH in CH$_2$Cl$_2$) to afford 51 g (90%) of 3-nitro-4'-(pyrrolidine-1-carbonyl)biphenyl-4-carbaldehyde. Preparation of tert-butyl (1E,4E)-4-(dipropylcarbamoyl)-8-(4-((R)-3-hydroxypyrrolidine-1-carbonyl)phenyl)-3H-benzo[b]azepin-2-ylcarbamate: To a solution of tert-butyl (1E,4E)-8-(4-((R)-3-(tert-butyldimethylsilyloxy)pyrrolidine-1-carbonyl)phenyl)-4-(dipropylcarbamoyl)-3H-benzo[b]azepin-2-ylcarbamate (225 mg, 0.327 mmol) in THF (4 mL) at 0° C. was added a solution of TBAF (0.34 mL, 0.34 mmol, 1 M solution in THF). The resulting mixture was warmed to room temperature and stirred for 1.5 hr. The reaction mixture was diluted with EtOAc and washed with brine (2×). The organic layer was dried over MgSO$_4$, filtered, and concentrated under reduced pressure to give the crude tert-butyl (1E,4E)-4-(dipropylcarbamoyl)-8-(4-((R)-3-hydroxypyrrolidine-1-carbonyl)phenyl)-3H-benzo[b]azepin-2-ylcarbamate that was used directly without further purification. Preparation of (1E,4E)-2-amino-N-(2-amino-2-oxoethyl)-N-propyl-8-(4-(pyrrolidine-1-carbonyl)phenyl)-3H-benzo[b]azepine-4-carboxamide: A solution of the crude tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. To this mixture was added saturated NaHCO$_3$ at 0° C. The aqueous layer was separated and extracted with CH$_2$Cl$_2$. The combined organic layers were dried over Na$_2$SO$_4$, filtered, and concentrated under reduced pressure to give the crude compound that was purified by silica gel flash column chromatography (MeOH:CH$_2$Cl$_2$=1:50).

MS APCI (+) m/z 393 (M+1) detected; $^1$H-NMR (400 MHz, CDCl$_3$) δ 8.77 (d, 1H), 8.55 (d, 1H), 7.95 (s, 1H), 7.41 (d, 1H), 7.36 (d, 1H), 7.25-7.28 (m, 1H), 6.82 (s, 1H), 4.80 (s, 2H), 3.47 (br s, 4H), 2.80 (s, 2H), 1.63-1.72 (m, 4H), 0.94 (t, 6H).

Example 184

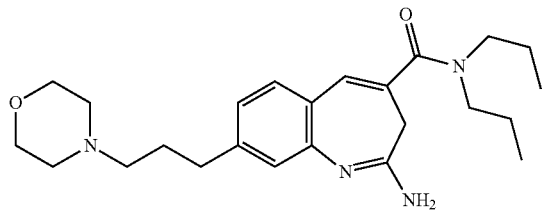 [SMILES: CCCN(CCC)C(=O)C1=Cc2ccc(CCCN3CCOCC3)cc2N=C(N)C1]

(1E,4E)-2-amino-8-(3-morpholinopropyl)-N,N-dipropyl-3H-benzo[b]azepine-4-carboxamide Step A: Preparation of 4-(3-(9-borabicyclo[3.3.1]nonan-9-yl)propyl)morpholine To a solution of 4-allylmorpholine (2.54 g, 20 mmol) in THF (40 mL) was added 9-BBN (2.44 g, 10 mmol). The reaction mixture was refluxed until the reaction was complete. After cooling to room temperature, the mixture was concentrated under reduced pressure to give the crude 4-(3-(9-borabicyclo[3.3.1]nonan-9-yl)propyl)morpholine that was used directly without further purification. LCMS ESI (+) m/z 250 (M+1) detected.

Step B: Preparation of (1E,4E)-2-amino-8-(3-morpholinopropyl)-N,N-dipropyl-3H-benzo[b]azepine-4-carboxamide The title compound was prepared by these procedures using tert-butyl (1E,4E)-8-bromo-4-(dipropylcarbamoyl)-3H-benzo[b]azepin-2-ylcarbamate and 4-(3-(9-borabicyclo[3.3.1]nonan-9-yl)propyl)morpholine. Preparation of 3-nitro-4'-(pyrrolidine-1-carbonyl)biphenyl-4-carbaldehyde, except in this case a co-solvent of EtOH/toluene/water (2:1:1) and Cs$_2$CO$_3$ as a base were used: To a solution of 4-bromo-2-nitrobenzaldehyde (20.2 g, 87.9 mmol), 4-(pyrrolidine-1-carbonyl)phenylboronic acid (21.2 g, 96.7 mmol), and Pd(PPh$_3$)$_4$ (508 mg, 0.440 mmol) in toluene (200 mL) was added EtOH (40 mL) followed by Na$_2$CO$_3$ (70.0 mL, 140 mmol, 2 M aq solution) at room temperature. The resulting mixture was heated at 100° C. for 18 h. The reaction mixture was cooled to room temperature and the organic layer was separated. The aqueous layer was extracted with EtOAc (300 mL). The combined organic layers were washed with brine (500 mL), dried over MgSO$_4$, filtered, and concentrated under reduced pressure to give the crude material that was combined with another batch of the crude material obtained from an additional run in the same reaction scale. The combined crude material was purified by silica gel flash column chromatography (CH$_2$Cl$_2$ to 1% MeOH in CH$_2$Cl$_2$). Preparation of (1E,4E)-2-amino-N-(2-amino-2-oxoethyl)-N-propyl-8-(4-(pyrrolidine-1-carbonyl)phenyl)-3H-benzo[b]azepine-4-carboxamide: A solution of the crude tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. To this mixture was added saturated NaHCO$_3$ at 0° C. The aqueous layer was separated and extracted with CH$_2$Cl$_2$. The combined organic layers were dried over Na$_2$SO$_4$, filtered, and concentrated under reduced pressure to give the crude compound that was purified by silica gel flash column chromatography (MeOH:CH$_2$Cl$_2$=1:50).

MS APCI (+) m/z 413 (M+1) detected; $^1$H-NMR (400 MHz, CDCl$_3$) δ 7.20 (d, 1H), 7.07 (br s, 1H), 6.90 (dd, 1H), 6.78 (s, 1H), 3.72 (t, 4H), 3.45 (br s, 4H), 2.76 (s, 2H), 2.67 (t, 2H), 2.43 (br s, 4H), 2.38 (t, 2H), 1.81-1.89 (m, 2H), 1.60-1.70 (m, 4H), 0.92 (t, 6H).

Example 185

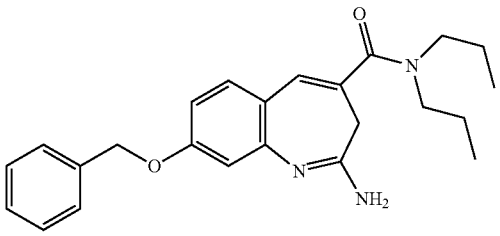 [SMILES: CCCN(CCC)C(=O)C1=Cc2ccc(OCc3ccccc3)cc2N=C(N)C1]

(1E,4E)-2-amino-8-(benzyloxy)-N,N-dipropyl-3H-benzo[b]azepine-4-carboxamide

The title compound was prepared by these procedures using (1E,4E)-ethyl 2-amino-8-(benzyloxy)-3H-benzo[b]azepine-4-carboxylate and dipropylamine. Preparation of (1E,4E)-ethyl 2-(tert-butoxycarbonylamino)-8-(4-(pyrrolidine-1-carbonyl)phenyl)-3H-benzo[b]azepine-4-carboxylate: To a mixture of (1E,4E)-ethyl 2-amino-8-(4-(pyrrolidine-1-carbonyl)phenyl)-3H-benzo[b]azepine-4-carboxylate (9.60 g, 23.8 mmol) in CH$_2$Cl$_2$ (100 mL) was added Boc$_2$O (5.97 mg, 27.4 mmol) at room temperature. The reaction mixture was stirred for 3 days. The resulting mixture was washed with saturated aq NaHCO$_3$ and brine. The organic layer was separated and dried over MgSO$_4$, filtered, and concentrated under reduced pressure to give 12.7 g of the crude (1E,4E)-ethyl 2-(tert-butoxycarbonylamino)-8-(4-(pyrrolidine-1-carbonyl)phenyl)-3H-benzo[b]azepine-4-carboxylate that was used directly without further purification. Preparation of (1E,4E)-2-(tert-butoxycarbonylamino)-8-(4-(pyrrolidine-1-carbonyl)phenyl)-3H-benzo[b]azepine-4-carboxylic acid: To a solution of (1E,4E)-ethyl 2-(tert-butoxycarbonylamino)-8-(4-(pyrrolidine-1-carbonyl)phenyl)-3H-benzo[b]azepine-4-carboxylate (12.0 g, 23.8 mmol) in THF-EtOH (60 mL/60 mL) was added 4 N aq. LiOH (23.8 mL, 95.3 mmol) at 0° C. The reaction mixture was warmed to room temperature and stirred for 21 h. Additional 6 mL of 4 N aq LiOH was added twice after 21 h and 24 h. After stirring for additional 6 h, the resulting mixture was concentrated under reduced pressure to give the crude material that was diluted with water (50 mL) and acidified to a pH of ~3.5 with 1 N aq phosphoric acid (~450 mL). ~250 mL of CH$_2$Cl$_2$ was added during acidification to extract the crude product out of the sticky suspension. The solids formed during acidification were filtered off using a glass filter packed with Celite. The aqueous layer was separated and extracted with CH$_2$Cl$_2$ (3×100 mL). The combined organic layers were dried over MgSO$_4$, filtered, and concentrated under reduced pressures to give the crude (1E,4E)-2-(tert-butoxycarbonylamino)-8-(4-(pyrrolidine-1-carbonyl)phenyl)-3H-benzo[b]azepine-4-carboxylic acid that was used directly without further purification. Preparation of tert-butyl (1E,4E)-4-(propylcarbamoyl)-8-(4-(pyrrolidine-1-carbonyl)phenyl)-3H-benzo[b]azepin-2-ylcarbamate: A mixture of (1E,4E)-2-(tert-butoxycarbonylamino)-8-(4-(pyrrolidine-1-carbonyl)phenyl)-3H-benzo[b]azepine-4-carboxylic acid (200 mg, 0.42 mmol), HOBt (114 mg, 0.84 mmol), and EDCI (161 mg, 0.84 mmol) in DMF (5 mL) was stirred for 1 h at room temperature. To this mixture was added triethylamine (0.12 mL, 0.84 mmol) and propan-1-amine (0.043 mL, 0.53 mmol) at room temperature. The resulting solution was stirred for additional 2 h. The reaction mixture was diluted with EtOAc (5 mL) and washed with saturated aq NH$_4$Cl. The aqueous layer was separated and extracted with EtOAc (3×5 mL). The combined organic layers were washed with brine (5 mL), saturated aq NaHCO$_3$ (5 mL), and brine (5 mL). The organic layer was dried over MgSO$_4$, filtered, and concentrated under reduced pressure to give the crude tert-butyl (1E,4E)-4-(propylcarbamoyl)-8-(4-(pyrrolidine-1-carbonyl)phenyl)-3H-benzo[b]azepin-2-ylcarbamate that was used directly without further purification. Preparation of (1E,4E)-2-amino-N-(2-amino-2-oxoethyl)-N-propyl-8-(4-(pyrrolidine-1-carbonyl)phenyl)-3H-benzo[b]azepine-4-carboxamide: A solution of the crude tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. To this mixture was added saturated NaHCO$_3$ at 0° C. The aqueous layer was separated and extracted with CH$_2$Cl$_2$. The combined organic layers were dried over Na$_2$SO$_4$, filtered, and concentrated under reduced pressure to give the crude compound that was purified by silica gel flash column chromatography (MeOH:CH$_2$Cl$_2$=1:50).

MS APCI (+) m/z 392 (M+1) detected; $^1$H-NMR (400 MHz, CDCl$_3$) δ 7.44-7.46 (m, 2H), 7.37-7.41 (m, 2H), 7.31-7.34 (m, 1H), 7.19 (d, 1H), 6.83 (d, 1H), 6.73-6.76 (m, 2H), 5.10 (s, 2H), 3.45 (br s, 4H), 2.77 (s, 2H), 1.60-1.70 (m, 4H), 0.92 (t, 6H).

Example 191

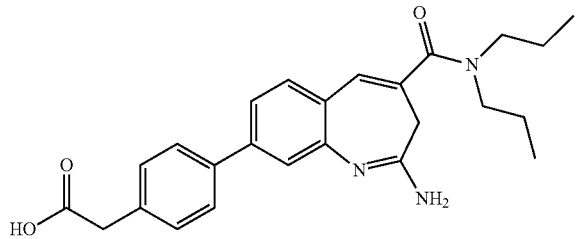 [SMILES: CCCN(CCC)C(=O)C1=Cc2ccc(-c3ccc(CC(=O)O)cc3)cc2N=C(N)C1]

2-(4-((1E,4E)-2-Amino-4-(dipropylcarbamoyl)-3H-benzo[b]azepin-8-yl)phenyl)acetic acid Step A: Benzyl 2-(4-(4,4,5,5-tetramethyl-1,3,2-dioxaborolan-2-yl)phenyl)acetate (41%) was prepared according to Example 192, Step A described below, benzyl alcohol for ethanol.

Step B: Benzyl 2-(4-((1E,4E)-2-amino-4-(dipropylcarbamoyl)-3H-benzo[b]azepin-8-yl)phenyl)acetate (33%) was prepared as follows, substituting benzyl 2-(4-(4,4,5,5-tetramethyl-1,3,2-dioxaborolan-2-yl)phenyl)acetate for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol), tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. m/z (APCI-pos) M+1=510.3.

Step C: 2-(4-((1E,4E)-2-Amino-4-(dipropylcarbamoyl)-3H-benzo[b]azepin-8-yl)phenyl)acetic acid (28%) was prepared as follows, substituting benzyl 2-(4-((1E,4E)-2-amino-4-(dipropylcarbamoyl)-3H-benzo[b]azepin-8-yl)phenyl)acetate for benzyl 4-((1E,4E)-2-amino-4-(dipropylcarbamoyl)-3H-benzo[b]azepin-8-yl)benzoate. Benzyl 4-((1E,4E)-2-amino-4-(dipropylcarbamoyl)-3H-benzo[b]azepin-8-yl)benzoate (0.025 g, 0.0504 mmol) was suspended in 1 ml of methanol, and 25 mgs of 10% Pd/C (Degussa type) was added and the mixture was hydrogenated under a balloon of hydrogen for one hour. This mixture was then filtered through GF/F filter paper, and the filtrate was concentrated. m/z (APCI-pos) M+1=420.2.

Example 192

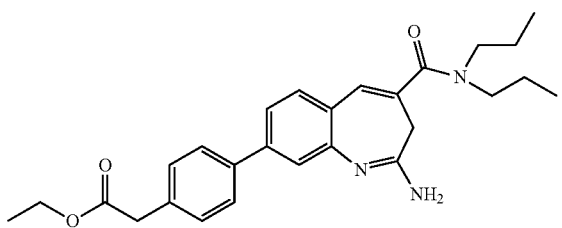 [SMILES: CCCN(CCC)C(=O)C1=Cc2ccc(-c3ccc(CC(=O)OCC)cc3)cc2N=C(N)C1]

Ethyl 2-(4-((1E,4E)-2-amino-4-(dipropylcarbamoyl)-3H-benzo[b]azepin-8-yl)phenyl)acetate Step A: 2-(4-(4,4,5,5-tetramethyl-1,3,2-dioxaborolan-2-yl)phenyl)acetic acid (0.18 mgs, 0.67 mmol) was dissolved in dry THF (7 mls). To this solution was added ethanol (0.037 mls, 0.81 mmol) and resin bound triphenylphosphine (0.93 g, 2.014 mmol, 2.16 mmol/g). This mixture was gently stirred at room temperature for 20 minutes. Diisopropylazidodicarboxylate (0.34 mls, 1.68 mmol) was then added and the mixture was stirred at room temperature for one hour, then filtered, and the resin rinsed several times with EtOAc. The filtrate was concentrated and the resulting material was purified by Flash 40 Biotage (40M cartridge, 30% EtOAc/Hexanes) to give 137 mgs (70%) of ethyl 2-(4-(4,4,5,5-tetramethyl-1,3,2-dioxaborolan-2-yl)phenyl)acetate as an orange oil.

Step B: Ethyl 2-(4-((1E,4E)-2-amino-4-(dipropylcarbamoyl)-3H-benzo[b]azepin-8-yl)phenyl)acetate (20%) was prepared as follows, substituting ethyl 2-(4-(4,4,5,5-tetramethyl-1,3,2-dioxaborolan-2-yl)phenyl)acetate for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. $^1$H NMR (400 MHz, CDCl$_3$) δ 7.59-7.65 (m, 2H), 7.48-7.53 (m, 1H), 7.30-7.39 (m, 4H), 6.84 (s, 1H), 5.50 (very broad s, 1H), 4.14-4.23 (m, 2H), 3.66 (s, 2H), 3.38-3.52 (m, 4H), 2.86 (m, 2H), 1.59-1.72 (m, 4H), 1.22-1.32 (m, 3H), 0.88-0.97 (m, 6H); m/z (APCI-pos) M+1=448.2.

Example 193

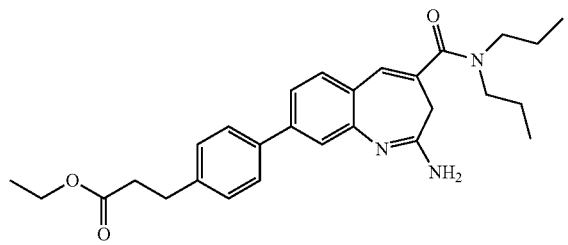 [SMILES: CCCN(CCC)C(=O)C1=Cc2ccc(-c3ccc(CCC(=O)OCC)cc3)cc2N=C(N)C1]

Ethyl 3-(4-((1E,4E)-2-amino-4-(dipropylcarbamoyl)-3H-benzo[b]azepin-8-yl)phenyl)propanoate Step A: Ethyl 3-(4-(4,4,5,5-tetramethyl-1,3,2-dioxaborolan-2-yl)phenyl)propanoate (24%) was prepared according to Example 192, Step A described above, substituting 3-(4-(4,4,5,5-tetramethyl-1,3,2-dioxaborolan-2-yl)phenyl)propanoic acid for 2-(4-(4,4,5,5-tetramethyl-1,3,2-dioxaborolan-2-yl)phenyl)acetic acid.

Step B: Ethyl 3-(4-((1E,4E)-2-amino-4-(dipropylcarbamoyl)-3H-benzo[b]azepin-8-yl)phenyl)propanoate (27%) was prepared as follows, substituting ethyl 3-(4-(4,4,5,5-tetramethyl-1,3,2-dioxaborolan-2-yl)phenyl)propanoate for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. $^1$H NMR (400 MHz, CDCl$_3$) δ 7.57-7.60 (m, 2H), 7.49-7.51 (m, 1H), 7.25-7.35 (m, 4H), 6.84 (s, 1H), 5.22 (very broad singlet, 1H), 4.11-4.17 (m, 2H), 3.41-3.51 (m, 4H), 2.95-3.04 (m, 2H), 2.83 (s, 2H), 2.64-2.69 (m, 2H), 1.58-1.72 (m, 4H), 1.20-1.30 (m, 3H), 0.88-0.99 (m, 6H); m/z (APCI-pos) M+1=462.3.

Example 196

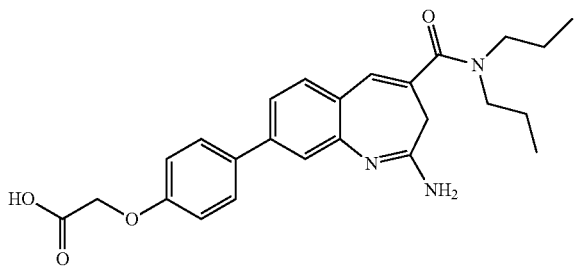 [SMILES: CCCN(CCC)C(=O)C1=Cc2ccc(-c3ccc(OCC(=O)O)cc3)cc2N=C(N)C1]

2-(4-((1E,4E)-2-Amino-4-(dipropylcarbamoyl)-3H-benzo[b]azepin-8-yl)phenoxy)acetic acid Step A: (1E,4E)-2-Amino-8-(4-(benzyloxy)phenyl)-N,N-dipropyl-3H-benzo[b]azepine-4-carboxamide (36%) was prepared as follows, substituting 4-(benzyloxy)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. m/z (APCI-pos) M+1=468.2.

Step B: (1E,4E)-2-Amino-8-(4-(benzyloxy)phenyl)-N,N-dipropyl-3H-benzo[b]azepine-4-carboxamide (0.100 g, 0.214 mmol), di-tert-butyl-dicarbonate (0.117 g, 0.535 mmol), and dimethylaminopyridine (0.026 g, 0.214 mmol) were combined in 3 mls of dry dichloromethane and stirred at room temperature for 16 hours. The mixture was then place directly on a Flash 40 Biotage column (40M, 3:1 Hexane:EtOAc) to give 0.056 g (40%) of product. m/z (APCI-pos) M+1=667.9.

Step C

The product from Step B (0.050 g, 0.075 mmol) was dissolved in 1 ml of EtOAc, and 0.050 g of 10% Pd/C were added. The mixture was hydrogenated under a balloon of hydrogen for 1 hour. Another 0.050 g of catalyst were added and the mixture hydrogenated for an additional 1.5 hours, then filtered through GF/F paper. The filtrate was concentrated under reduced pressure to give 37 mgs (87%) of product. m/z (APCI-pos) M+1=577.9.

Step D

The product from Step C (0.030 g, 0.519 mmol) was dissolved in 1 ml of dry DMF. To this was added cesium carbonate (0.051 g, 0.156 mmol) and benzyl-2-bromoacetate (0.012 mls, 0.078 mmol) and the mixture was stirred at room temperature for 16 hours. The reaction mixture was then diluted with EtOAc, washed several times with brine, dried over sodium sulfate and concentrated under reduced pressure. The resulting residue was then dissolved in 1 ml of dichloromethane, and 1 ml of TFA was then added. After 1 hour, the mixture was concentrated under reduced pressure and the resulting residue neutralized with concentrated ammonium hydroxide and water, extracted with dichloromethane, extracts dried over sodium sulfate and concentrated under reduced pressure. Preparative thin layer chromatography (2×0.5 mm plates, 7% MeOH/DCM) afforded 0.015 g (55%) of benzyl 2-(4-((1E,4E)-2-amino-4-(dipropylcarbamoyl)-3H-benzo[b]azepin-8-yl)phenoxy)acetate. m/z (APCI-pos) M+1=526.2.

Step E: 2-(4-((1E,4E)-2-amino-4-(dipropylcarbamoyl)-3H-benzo[b]azepin-8-yl)phenoxy)acetic acid (46%) was prepared as follows, substituting benzyl 2-(4-((1E,4E)-2-amino-4-(dipropylcarbamoyl)-3H-benzo[b]azepin-8-yl)phenoxy)acetate for benzyl 4-((1E,4E)-2-amino-4-(dipropylcarbamoyl)-3H-benzo[b]azepin-8-yl)benzoate.
Benzyl 4-((1E,4E)-2-amino-4-(dipropylcarbamoyl)-3H-benzo[b]azepin-8-yl)benzoate (0.025 g, 0.0504 mmol) was suspended in 1 ml of methanol, and 25 mgs of 10% Pd/C (Degussa type) was added and the mixture was hydrogenated under a balloon of hydrogen for one hour. This mixture was then filtered through GF/F filter paper, and the filtrate was concentrated. $^1$H NMR (400 MHz, DMSO-$d_6$) δ 7.48-7.56 (m, 2H), 7.33-7.42 (m, 1H), 7.21-7.30 (m, 3H), 6.93-7.00 (m, 3H), 6.77 (s, 1H), 4.43 (s, 2H), 2.87 (s, 2H), 1.45-1.61 (m, 4H), 0.74-0.92 (m, 6H); m/z (APCI-neg) M−1=434.0.

Example 197

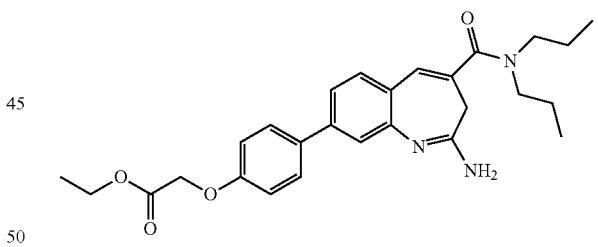

Ethyl 2-(4-((1E,4E)-2-amino-4-(dipropylcarbamoyl)-3H-benzo[b]azepin-8-yl)phenoxy)acetate Step A: Ethyl 2-(4-((1E,4E)-2-amino-4-(dipropylcarbamoyl)-3H-benzo[b]azepin-8-yl)phenoxy)acetate (21%) was prepared as follows, substituting ethyl 2-(4-(4,4,5,5-tetramethyl-1,3,2-dioxaborolan-2-yl)phenoxy)acetate for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl) phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol)

were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. $^1$H NMR (400 MHz, DMSO-$d_6$) δ 7.58-7.63 (m, 2H), 7.33-7.37 (m, 1H), 7.19-7.26 (m, 2H), 6.98-7.03 (m, 2H), 6.75 (s, 1H), 4.82 (s, 2H), 4.15-4.22 (m, 2H), 3.25-3.34 (m, 4H), 2.76 (s, 2H), 1.50-1.61 (m, 4H), 1.19-1.26 (m, 3H), 0.73-0.90 (m, 6H); m/z (APCI-pos) M+1=464.3.

Example 198

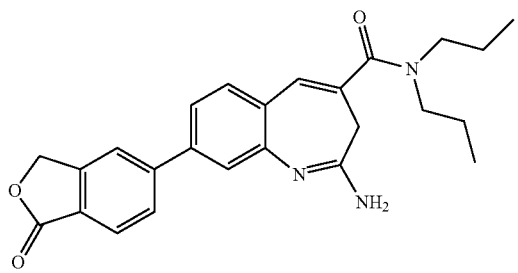 [SMILES: CCCN(CCC)C(=O)C1=Cc2ccc(-c3ccc4c(c3)COC4=O)cc2N=C(N)C1]

(1E,4E)-2-Amino-8-(1-oxo-1,3-dihydroisobenzo-furan-5-yl)-N,N-dipropyl-3H-benzo[b]azepine-4-carboxamide Step A: 5-(4,4,5,5-Tetramethyl-1,3,2-dioxaborolan-2-yl)isobenzofuran-1(3H)-one (57%) was prepared according to Example 224/225, Step C described below.

Step B: (1E,4E)-2-Amino-8-(1-oxo-1,3-dihydroisobenzofuran-5-yl)-N,N-dipropyl-3H-benzo[b]azepine-4-carboxamide was prepared as follows, substituting 5-(4,4,5,5-tetramethyl-1,3,2-dioxaborolan-2-yl)isobenzofuran-1(3H)-one for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. $^1$H NMR (400 MHz, CDCl$_3$) δ 7.96-8.00 (m, 1H), 7.78-7.82 (m, 1H), 7.72-7.74 (m, 1H), 7.52-7.55 (m, 1H), 7.38-7.42 (m, 1H), 7.30-7.35 (m, 1H), 6.85 (s, 1H), 5.37 (s, 2H), 3.60-3.71 (m, 2H), 3.39-3.53 (m, 4H), 2.85 (m, 2H), 1.59-1.75 (m, 4H), 0.90-0.99 (m, 6H); m/z (APCI-pos) M+1=418.2.

Example 199

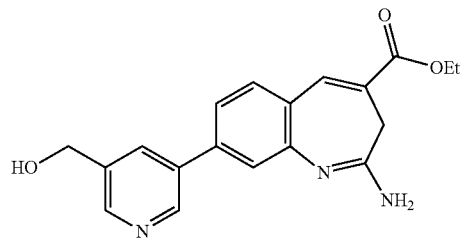 [SMILES: CCOC(=O)C1=Cc2ccc(-c3cncc(CO)c3)cc2N=C(N)C1]

(1E,4E)-ethyl 2-amino-8-(5-(hydroxymethyl)pyridin-3-yl)-3H-benzo[b]azepine-4-carboxylate The title compound was prepared by these procedures using (1E,4E)-ethyl 8-bromo-2-(tert-butoxycarbonylamino)-3H-benzo[b]azepine-4-carboxylate and 3-((tert-butyldimethylsilyloxy)methyl)phenylboronic acid. Preparation of 3-nitro-4'-(pyrrolidine-1-carbonyl)biphenyl-4-carbaldehyde, except in this case Cs$_2$CO$_3$ was used: To a solution of 4-bromo-2-nitrobenzaldehyde (20.2 g, 87.9 mmol), 4-(pyrrolidine-1-carbonyl)phenylboronic acid (21.2 g, 96.7 mmol), and Pd(PPh$_3$)$_4$ (508 mg, 0.440 mmol) in toluene (200 mL) was added EtOH (40 mL) followed by Na$_2$CO$_3$ (70.0 mL, 140 mmol, 2 M aq solution) at room temperature. The resulting mixture was heated at 100° C. for 18 h. The reaction mixture was cooled to room temperature and the organic layer was separated. The aqueous layer was extracted with EtOAc (300 mL). The combined organic layers were washed with brine (500 mL), dried over MgSO$_4$, filtered, and concentrated under reduced pressure to give the crude material that was combined with another batch of the crude material obtained from an additional run in the same reaction scale. The combined crude material was purified by silica gel flash column chromatography (CH$_2$Cl$_2$ to 1% MeOH in CH$_2$Cl$_2$). Preparation of tert-butyl (1E,4E)-4-(dipropylcarbamoyl)-8-(4-((R)-3-hydroxypyrrolidine-1-carbonyl)phenyl)-3H-benzo[b]azepin-2-ylcarbamate: To a solution of tert-butyl (1E,4E)-8-(4-((R)-3-(tert-butyldimethylsilyloxy)pyrrolidine-1-carbonyl)phenyl)-4-(dipropylcarbamoyl)-3H-benzo[b]azepin-2-ylcarbamate (225 mg, 0.327 mmol) in THF (4 mL) at 0° C. was added a solution of TBAF (0.34 mL, 0.34 mmol, 1 M solution in THF). The resulting mixture was warmed to room temperature and stirred for 1.5 hr. The reaction mixture was diluted with EtOAc and washed with brine (2×). The organic layer was dried over MgSO$_4$, filtered, and concentrated under reduced pressure to give the crude tert-butyl (1E,4E)-4-(dipropylcarbamoyl)-8-(4-((R)-3-hydroxypyrrolidine-1-carbonyl)phenyl)-3H-benzo[b]azepin-2-ylcarbamate that was used directly without further purification. Preparation of (1E,4E)-2-amino-N-(2-amino-2-oxoethyl)-N-propyl-8-(4-(pyrrolidine-1-carbonyl)phenyl)-3H-benzo[b]azepine-4-carboxamide: A solution of the crude tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. To this mixture was added saturated NaHCO$_3$ at 0° C. The aqueous layer was separated and extracted with CH$_2$Cl$_2$. The combined organic layers were dried over Na$_2$SO$_4$, filtered, and concentrated under reduced pressure to give the crude compound that was purified by silica gel flash column chromatography (MeOH:CH$_2$Cl$_2$=1:50).

MS APCI (+) m/z 338 (M+1) detected; $^1$H-NMR (400 MHz, CDCl$_3$) δ 8.78 (s, 1H), 8.57 (s, 1H), 7.96 (s, 1H), 7.84 (s, 1H), 7.49 (d, 1H), 7.42 (s, 1H), 7.31 (d, 1H), 4.80 (s, 2H), 4.33 (q, 2H), 3.00 (s, 2H), 1.40 (t, 3H).

Example 200

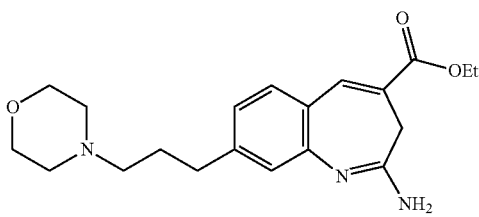 [SMILES: CCOC(=O)C1=Cc2ccc(CCCN3CCOCC3)cc2N=C(N)C1]

(1E,4E)-ethyl 2-amino-8-(3-morpholinopropyl)-3H-benzo[b]azepine-4-carboxylate

The title compound was prepared by these procedures using (1E,4E)-ethyl 8-bromo-2-(tert-butoxycarbonylamino)-3H-benzo[b]azepine-4-carboxylate and 4-(3-(9-borabicyclo[3.3.1]nonan-9-yl)propyl)morpholine. Preparation of 3-nitro-4'-(pyrrolidine-1-carbonyl)biphenyl-4-carbaldehyde, except in this case a co-solvent of EtOH/toluene/water (2:1:1) and Cs$_2$CO$_3$ were used: To a solution of 4-bromo-2-nitrobenzaldehyde (20.2 g, 87.9 mmol), 4-(pyrrolidine-1-carbonyl)phenylboronic acid (21.2 g, 96.7 mmol), and Pd(PPh$_3$)$_4$ (508 mg, 0.440 mmol) in toluene (200 mL) was added EtOH (40 mL) followed by Na$_2$CO$_3$ (70.0 mL, 140 mmol, 2 M aq solution) at room temperature. The resulting mixture was heated at 100° C. for 18 h. The reaction mixture was cooled to room temperature and the organic layer was separated. The aqueous layer was extracted with EtOAc (300 mL). The combined organic layers were washed with brine (500 mL), dried over MgSO$_4$, filtered, and concentrated under reduced pressure to give the crude material that was combined with another batch of the crude material obtained from an additional run in the same reaction scale. The combined crude material was purified by silica gel flash column chromatography (CH$_2$Cl$_2$ to 1% MeOH in CH$_2$Cl$_2$). Preparation of (1E,4E)-2-amino-N-(2-amino-2-oxoethyl)-N-propyl-8-(4-(pyrrolidine-1-carbonyl)phenyl)-3H-benzo[b]azepine-4-carboxamide: A solution of the crude tert-butyl (1E,4E)-4-((2-amino-2-oxoethyl)(propyl)carbamoyl)-8-(4-(pyrrolidine-1-carbonyl)phenyl)-3H-benzo[b]azepin-2-ylcarbamate in anhydrous CH$_2$Cl$_2$ (15 mL) was bubbled with HCl (gas) for 4 h at 0° C. The resulting mixture was warmed to room temperature and stirred until the reaction was complete. To this mixture was added saturated NaHCO$_3$ at 0° C. The aqueous layer was separated and extracted with CH$_2$Cl$_2$. The combined organic layers were dried over Na$_2$SO$_4$, filtered, and concentrated under reduced pressure to give the crude compound that was purified by silica gel flash column chromatography (MeOH:CH$_2$Cl$_2$=1:50).

MS APCI (+) m/z 358 (M+1) detected; $^1$H-NMR (400 MHz, CDCl$_3$) δ 7.78 (s, 1H), 7.30 (d, 1H), 7.06 (s, 1H), 6.92 (d, 1H), 4.30 (q, 2H), 3.72 (t, 4H), 2.94 (s, 2H), 2.67 (t, 2H), 2.43 (br s, 4H), 2.38 (t, 2H), 1.81-1.89 (m, 2H), 1.37 (t, 3H).

Example 201

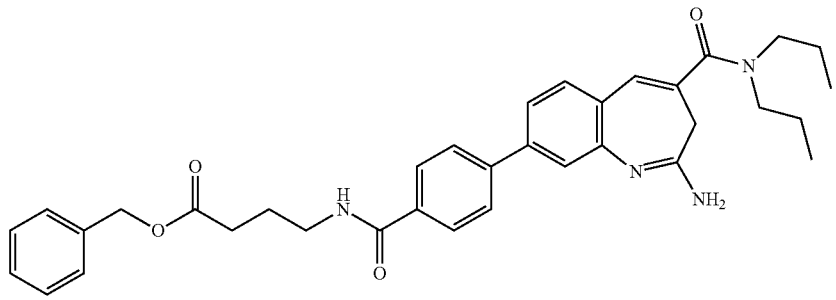 [SMILES: CCCN(CCC)C(=O)C1=Cc2ccc(-c3ccc(C(=O)NCCCC(=O)OCc4ccccc4)cc3)cc2N=C(N)C1]

benzyl 4-(4-((1E,4E)-2-amino-4-(dipropylcarbamoyl)-3H-benzo[b]azepin-8-yl)benzamido)butanoate Step A: Preparation of benzyl 4-(4-(4,4,5,5-tetramethyl-1,3,2-dioxaborolan-2-yl)benzamido)butanoate The title compound was prepared by these procedures using 4-(4,4,5,5-tetramethyl-1,3,2-dioxaborolan-2-yl)benzoic acid and benzyl 4-aminobutanoate 4-methylbenzenesulfonate. Preparation of tert-butyl (1E,4E)-4-(propylcarbamoyl)-8-(4-(pyrrolidine-1-carbonyl)phenyl)-3H-benzo[b]azepin-2-ylcarbamate: A mixture of (1E,4E)-2-(tert-butoxycarbonylamino)-8-(4-(pyrrolidine-1-carbonyl)phenyl)-3H-benzo[b]azepine-4-carboxylic acid (200 mg, 0.42 mmol), HOBt (114 mg, 0.84 mmol), and EDCI (161 mg, 0.84 mmol) in DMF (5 mL) was stirred for 1 h at room temperature. To this mixture was added triethylamine (0.12 mL, 0.84 mmol) and propan-1-amine (0.043 mL, 0.53 mmol) at room temperature. The resulting solution was stirred for additional 2 h. The reaction mixture was diluted with EtOAc (5 mL) and washed with saturated aq NH$_4$Cl. The aqueous layer was separated and extracted with EtOAc (3×5 mL). The combined organic layers were washed with brine (5 mL), saturated aq NaHCO$_3$ (5 mL), and brine (5 mL). The organic layer was dried over MgSO$_4$, filtered, and concentrated under reduced pressure to give the crude tert-butyl (1E,4E)-4-(propylcarbamoyl)-8-(4-(pyrrolidine-1-carbonyl)phenyl)-3H-benzo[b]azepin-2-ylcarbamate that was used directly without further purification. MS APCI (+) m/z 424 (M+1) detected.

Step B: Preparation of benzyl 4-(4-((1E,4E)-2-amino-4-(dipropylcarbamoyl)-3H-benzo[b]azepin-8-yl)benzamido)butanoate The title compound was prepared by these procedures using tert-butyl (1E,4E)-8-bromo-4-(dipropylcarbamoyl)-3H-benzo[b]azepin-2-ylcarbamate and benzyl 4-(4-(4,4,5,5-tetramethyl-1,3,2-dioxaborolan-2-yl)benzamido)butanoate. Preparation of tert-butyl (1E,4E)-8-(4-(dimethylcarbamoyl)phenyl)-4-(dipropylcarbamoyl)-3H-benzo[b]azepin-2-ylcarbamate, except in this case a co-solvent of MeCN-water (1.5:1) was used: To Na$_2$CO$_3$ (129 mg, 1.214 mmol) in a 50 mL round-bottom flask was added water (3.7 mL) was bubbled with N$_2$ for 10 min. To this mixture was added tert-butyl (1E,4E)-8-bromo-4-(dipropylcarbamoyl)-3H-benzo[b]azepin-2-ylcarbamate (200 mg, 0.40 mmol) in EtOH (4.9 mL) at room temperature. The resulting mixture was bubbled with N$_2$ for 10 min. Pd(OAc)$_2$ (9.3 mg, 0.040 mmol) and 4,4'-(phenylphosphinidene)bisbenzenesulfonic acid dipotassium hydrate (45 mg, 0.081 mmol) were added. The resulting mixture was warmed to 65° C. with N$_2$ bubbling. To this mixture was added a solution of 4-(dimethylcarbamoyl)phenylboronic acid (97 mg, 0.49 mmol) in EtOH (0.6 mL). The resulting mixture was stirred at 65° C. for 1 h. The reaction mixture was cooled to room temperature and concentrated under reduced pressure to give the crude material that was diluted with water (5 mL) and EtOAc (10 mL). The mixture was filtered through GF/F filter. The aqueous layer was separated and extracted with EtOAc (10 mL). The combined organic layers were washed with brine (10 mL), dried over MgSO$_4$, filtered, and concentrated under reduced pressure to give the crude product that was purified by silica gel flash column chromatography (CH$_2$Cl$_2$ to 2% MeOH in CH$_2$Cl$_2$). Preparation of (1E,4E)-2-amino-N-propyl-8-(4-(pyrrolidine-1-carbonyl)phenyl)-3H-benzo[b]azepine-4-carboxamide: To a solution of tert-butyl (1E,4E)-4-(propylcarbamoyl)-8-(4-(pyrrolidine-1-carbonyl)phenyl)-3H-benzo[b]azepin-2-ylcarbamate (450 mg, 0.87 mmol) in CH$_2$Cl$_2$ (5 mL) was added 2,2,2-trifluoroacetic acid (1.36 mL, 17.4 mmol) at 0° C. The reaction mixture was warmed to room temperature and stirred for 2 h. The reaction mixture was concentrated under reduced pressure to give the crude material that was diluted with CH$_2$Cl$_2$ (10 mL) and saturated aq NaHCO$_3$ (15 mL) again. The resulting mixture was stirred for 30 min at room temperature. The aqueous layer was separated and extracted with CH$_2$Cl$_2$ (1×10 mL). The combined organic layers were washed with saturated aq NaHCO$_3$ (2×10 mL) and brine (1×10 mL), dried over MgSO$_4$, filtered, and concentrated under reduced pressure to give the crude material again that was purified by silica gel flash column chromatography (1 to 5% MeOH in CH$_2$Cl$_2$, gradient).

MS APCI (+) m/z 581 (M+1) detected; $^1$H-NMR (400 MHz, CDCl$_3$) δ 7.82-7.84 (m, 2H), 7.70-7.72 (m, 2H), 7.51 (d, 1H), 7.30-7.38 (m, 7H), 6.83 (s, 1H), 6.53 (t, 1H), 5.13 (s, 2H), 3.54 (q, 2H), 3.47 (br s, 4H), 2.81 (s, 2H), 2.52 (t, 2H), 1.98-2.04 (m, 2H), 1.62-1.72 (m, 4H), 0.93 (t, 6H).

Example 205

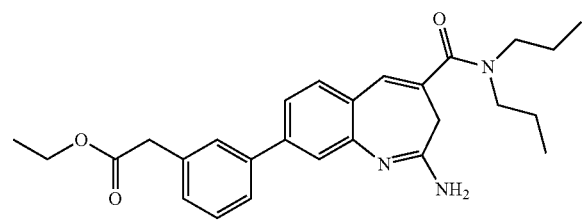 [SMILES: CCCN(CCC)C(=O)C1=Cc2ccc(-c3cccc(CC(=O)OCC)c3)cc2N=C(N)C1]

Ethyl 2-(3-((1E,4E)-2-amino-4-(dipropylcarbamoyl)-3H-benzo[b]azepin-8-yl)phenyl)acetate

Step A

To 2-(3-(4,4,5,5-tetramethyl-1,3,2-dioxaborolan-2-yl)phenyl)acetic acid (0.50 g, 1.91 mmol) in 20 mls of dry DMF was added cesium carbonate (1.24 g, 3.82 mmole) and iodoethane (0.20 mls, 2.48 mmol). This mixture was stirred at room temperature for 16 hours, then diluted with brine, extracted twice with EtOAc, extracts washed with brine (2×), dried over sodium sulfate and concentrated under reduced pressure to give 360 mgs (65%) of ethyl 2-(3-(4,4,5,5-tetramethyl-1,3,2-dioxaborolan-2-yl)phenyl)acetate as a clear oil.

Step B: Ethyl 2-(3-((1E,4E)-2-amino-4-(dipropylcarbamoyl)-3H-benzo[b]azepin-8-yl)phenyl)acetate was prepared as follows, substituting ethyl 2-(3-(4,4,5,5-tetramethyl-1,3,2-dioxaborolan-2-yl)phenyl)acetate for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. $^1$H NMR (400 MHz, CDCl$_3$) δ 7.49-7.60 (m, 3H), 7.26-7.42 (m, 4H), 6.83 (s, 1H), 5.20 (br s, 1H), 4.12-4.21 (m, 2H), 3.67 (s, 2H), 3.42-3.52 (m, 4H), 2.83 (s, 2H), 1.56-1.74 (m, 4H), 1.23-1.30 (m, 3H), 0.90-0.97 (m, 6H); m/z (APCI-pos) M+1=448.3.

Example 213

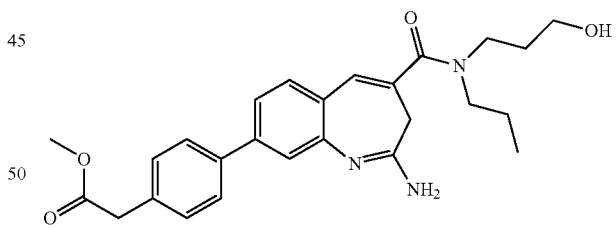

Methyl 2-(4-((1E,4E)-2-amino-4-((3-hydroxypropyl)(propyl)carbamoyl)-3H-benzo[b]azepin-8-yl)phenyl)acetate

Step A: Methyl 2-(4-((1E,4E)-2-amino-4-((3-hydroxypropyl)(propyl)carbamoyl)-3H-benzo[b]azepin-8-yl)phenyl)acetate was prepared as follows, substituting 4-(2-methoxy-2-oxoethyl)phenylboronic acid for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, CDCl$_3$) δ 7.59-7.66 (m, 2H), 7.48-7.51 (m, 1H), 7.28-7.39 (m, 4H), 6.87 (s, 1H), 3.72 (s, 3H), 3.57-3.70 (m, 6H), 3.45-3.53 (m, 2H), 2.83 (s, 2H), 1.79-1.88 (m, 2H), 1.65-1.75 (m, 2H), 0.90-0.96 (m, 3H); m/z (APCI-pos) M+1=450.2.

Example 214

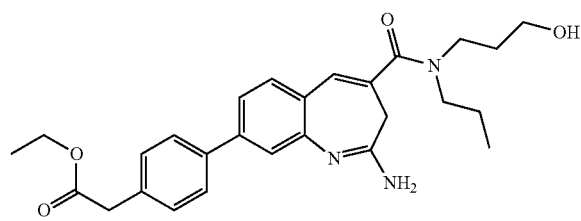 [SMILES: CCCN(CCCO)C(=O)C1=Cc2ccc(-c3ccc(CC(=O)OCC)cc3)cc2N=C(N)C1]

Ethyl 2-(4-((1E,4E)-2-amino-4-((3-hydroxypropyl)(propyl)carbamoyl)-3H-benzo[b]azepin-8-yl)phenyl)acetate Step A: Ethyl 2-(4-((1E,4E)-2-amino-4-((3-hydroxypropyl)(propyl)carbamoyl)-3H-benzo[b]azepin-8-yl)phenyl)acetate (40%) was prepared as follows, substituting 4-(2-ethoxy-2-oxoethyl)phenylboronic acid for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, DMSO-d$_6$) δ 7.60-7.68 (m, 2H), 7.20-7.41 (m, 5H), 6.73-6.85 (m, 3H), 4.42-4.52 (m, 1H), 4.05-4.16 (m, 2H), 3.71 (s, 2H), 3.24-3.52 (m, 6H, partially obscured by water peak), 2.75 (s, 2H), 1.66-1.78 (m, 2H), 1.50-1.65 (m, 2H), 1.15-1.23 (m, 3H), 0.75-0.92 (m, 3H); m/z (APCI-pos) M+1=464.2.

Example 215

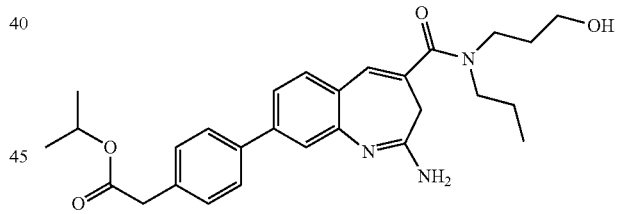

Isopropyl 2-(4-((1E,4E)-2-amino-4-((3-hydroxypropyl)(propyl)carbamoyl)-3H-benzo[b]azepin-8-yl)phenyl)acetate Step A: Isopropyl 2-(4-(4,4,5,5-tetramethyl-1,3,2-dioxaborolan-2-yl)phenyl)acetate (59%) was prepared according to Example 192, Step A described above, substituting 2-propanol for ethanol.

Step B: Isopropyl 2-(4-((1E,4E)-2-amino-4-((3-hydroxypropyl)(propyl)carbamoyl)-3H-benzo[b]azepin-8-yl)phenyl)acetate (42%) was prepared as follows, substituting isopropyl 2-(4-(4,4,5,5-tetramethyl-1,3,2-dioxaborolan-2-yl)phenyl)acetate for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, CDCl$_3$) δ 7.58-7.64 (m, 2H), 7.48-7.52 (m, 1H), 7.31-7.39 (m, 4H), 6.88 (s, 1H), 5.00-5.08 (m, 1H), 3.58-3.69 (m 6H), 3.44-3.51 (m, 2H), 2.85 (m, 2H), 1.79-1.88 (m, 2H), 1.65-1.75 (m, 2H), 1.23-1.28 (m, 6H), 0.90-0.97 (m, 3H); m/z (APCI-pos) M+1=478.3.

Example 216

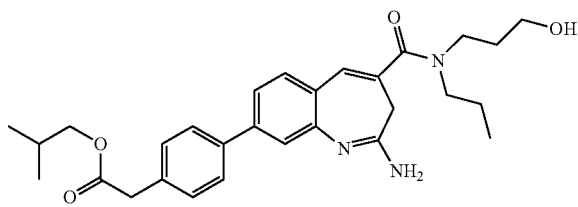 [SMILES: CCCN(CCCO)C(=O)C1=Cc2ccc(-c3ccc(CC(=O)OCC(C)C)cc3)cc2N=C(N)C1]

Isobutyl 2-(4-((1E,4E)-2-amino-4-((3-hydroxypropyl)(propyl)carbamoyl)-3H-benzo[b]azepin-8-yl)phenyl)acetate Step A: Isobutyl 2-(4-(4,4,5,5-tetramethyl-1,3,2-dioxaborolan-2-yl)phenyl)acetate (54%) was prepared according to Example 192, Step A described above, substituting 2-methylpropan-1-ol for ethanol.

Step B: Isobutyl 2-(4-((1E,4E)-2-amino-4-((3-hydroxypropyl)(propyl)carbamoyl)-3H-benzo[b]azepin-8-yl)phenyl)acetate (40%) was prepared as follows, substituting isobutyl 2-(4-(4,4,5,5-tetramethyl-1,3,2-dioxaborolan-2-yl)phenyl) acetate for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, CDCl$_3$) δ7.59-7.65 (m, 2H), 7.48-7.51 (m, 1H), 7.29-7.39 (m, 4H), 6.87 (s, 1H), 5.08 (br s, 1H), 3.87-3.92 (m, 2H), 3.58-3.71 (m, 6H), 3.45-3.52 (m, 2H), 2.82 (s, 2H), 1.78-1.99 (m, 3H), 1.64-1.77 (m, 2H), 0.87-0.97 (m, 9H); m/z (APCI-pos) M+1=492.2.

Example 217

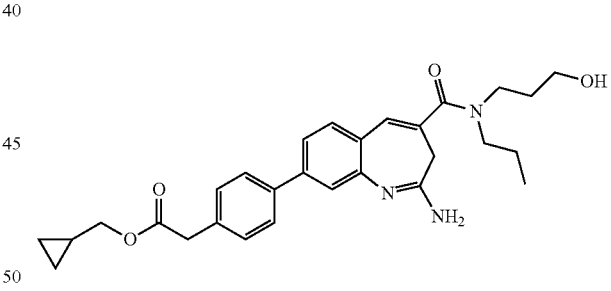

Cyclopropylmethyl 2-(4-((1E,4E)-2-amino-4-((3-hydroxypropyl)(propyl)carbamoyl)-3H-benzo[b]azepin-8-yl)phenyl)acetate Step A: Cyclopropylmethyl 2-(4-(4,4,5,5-tetramethyl-1,3,2-dioxaborolan-2-yl)phenyl)acetate (47%) was prepared according to Example 192, Step A described above, substituting cyclopropylmethanol for ethanol.

Step B: Cyclopropylmethyl 2-(4-((1E,4E)-2-amino-4-((3-hydroxypropyl)(propyl)carbamoyl)-3H-benzo[b]azepin-8-yl)phenyl)acetate (31%) was prepared as follows, substituting cyclopropylmethyl 2-(4-(4,4,5,5-tetramethyl-1,3,2-dioxaborolan-2-yl)

phenyl)acetate for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, CDCl$_3$) δ 7.59-7.65 (m, 2H), 7.47-7.51 (m, 1H), 7.28-7.40 (m, 4H), 6.88 (s, 1H), 5.18 (br s, 1H), 3.92-3.99 (m, 2H), 3.58-3.72 (m, 6H), 3.43-3.53 (m, 2H), 2.83 (s, 2H), 1.79-1.88 (m, 2H), 1.65-1.77 (m, 2H), 1.08-1.20 (m, 1H), 0.90-0.98 (m, 3H), 0.53-0.60 (m, 2H), 0.24-0.31 (m, 2H); m/z (APCI-pos) M+1=490.2.

Example 218

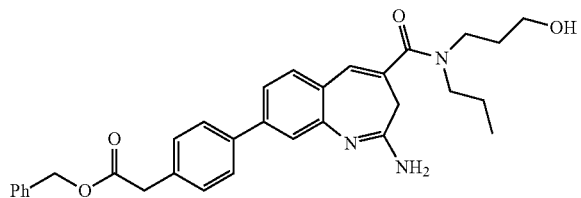 [SMILES: CCCN(CCCO)C(=O)C1=Cc2ccc(-c3ccc(CC(=O)OCc4ccccc4)cc3)cc2N=C(N)C1]

Benzyl 2-(4-((1E,4E)-2-amino-4-((3-hydroxypropyl)(propyl)carbamoyl)-3H-benzo[b]azepin-8-yl)phenyl)acetate Step A: Benzyl 2-(4-((1E,4E)-2-amino-4-((3-hydroxypropyl)(propyl)carbamoyl)-3H-benzo[b]azepin-8-yl)phenyl)acetate (31%) was prepared as follows, substituting benzyl 2-(4-(4,4,5,5-tetramethyl-1,3,2-dioxaborolan-2-yl)phenyl)acetate for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, CDCl$_3$) δ 7.59-7.64 (m, 2H), 7.49-7.51 (m, 1H), 7.29-7.39 (m, 9H), 6.88 (s, 1H), 5.16 (s, 2H), 3.70 (s, 2H), 3.58-3.69 (m, 4H), 3.45-3.52 (m, 2H), 2.84 (s, 2H), 1.79-1.88 (m, 2H), 1.66-1.77 (m, 2H), 0.90-0.97 (m, 3H); m/z (APCI-pos) M+1=526.2.

Example 219

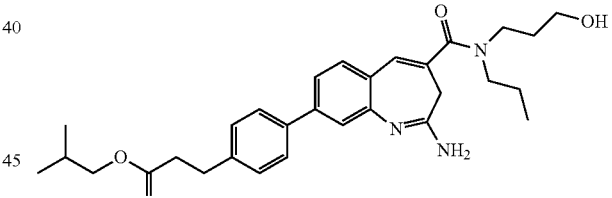

Isobutyl 3-(4-((1E,4E)-2-amino-4-((3-hydroxypropyl)(propyl)carbamoyl)-3H-benzo[b]azepin-8-yl)phenyl)propanoate Step A: Isobutyl 3-(4-(4,4,5,5-tetramethyl-1,3,2-dioxaborolan-2-yl)phenyl)propanoate (67%) was prepared according to Example 192, Step A described above, substituting 3-(4-(4,4,5,5-tetramethyl-1,3,2-dioxaborolan-2-yl)phenyl)propanoic acid for 2-(4-(4,4,5,5-tetramethyl-1,3,2-dioxaborolan-2-yl)phenyl)acetic acid and 2-methylpropan-1-ol for ethanol.

Step B: Isobutyl 3-(4-((1E,4E)-2-amino-4-((3-hydroxypropyl)(propyl)carbamoyl)-3H-benzo[b]azepin-8-yl)phenyl)propanoate (31%) was prepared as follows, substituting isobutyl 3-(4-(4,4,5,5-tetramethyl-1,3,2-dioxaborolan-2-yl)phenyl)

propanoate for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, CDCl$_3$) δ 7.56-7.60 (m, 2H), 7.47-7.50 (m, 1H), 7.26-7.36 (m, 4H), 6.87 (s, 1H), 5.08 (br s, 2H), 3.85-3.89 (m, 2H), 3.58-3.69 (m, 5H), 3.45-3.52 (m, 2H), 2.97-3.03 (m, 2H), 2.82 (s, 2H), 2.65-2.71 (m, 2H), 1.79-1.95 (m, 3H), 1.66-1.76 (m, 2H), 0.88-0.97 (m, 9H); m/z (APCI-pos) M+1=506.3.

Example 221

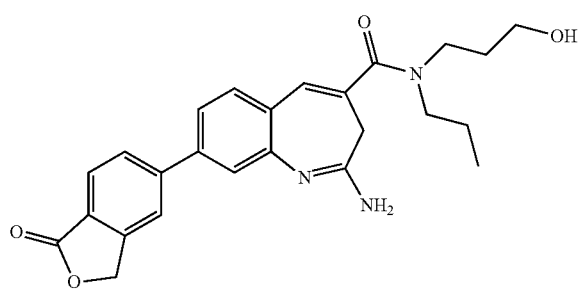 [SMILES: CCCN(CCCO)C(=O)C1=Cc2ccc(-c3ccc4c(c3)COC4=O)cc2N=C(N)C1]

(1E,4E)-2-Amino-N-(3-hydroxypropyl)-8-(1-oxo-1,3-dihydroisobenzofuran-5-yl)-N-propyl-3H-benzo[b]azepine-4-carboxamide Step A: 5-(4,4,5,5-Tetramethyl-1,3,2-dioxaborolan-2-yl)isobenzofuran-1(3H)-one (57%) was prepared according to Example 224/225, Step C described below, substituting 5-bromoisobenzofuran-1(3H)-one for 4-(4-bromophenyl)-1,3-dioxolan-2-one.

Step B: (1E,4E)-2-Amino-N-(3-hydroxypropyl)-8-(1-oxo-1,3-dihydroisobenzofuran-5-yl)-N-propyl-3H-benzo[b]azepine-4-carboxamide (33%) was prepared as follows, substituting 5-(4,4,5,5-tetramethyl-1,3,2-dioxaborolan-2-yl)isobenzofuran-1(3H)-one for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, CDCl$_3$) δ 7.95-8.00 (m, 1H), 7.78-7.82 (m, 1H), 7.70-7.73 (m, 1H), 7.50-7.53 (m, 1H), 7.37-7.42 (m, 1H), 7.28-7.33 (m, 1H), 6.89 (s, 1H), 5.37 (s, 2H), 5.12 (br s, 1H), 3.58-3.71 (m, 4H), 3.43-3.55 (m, 3H), 2.82 (m, 2H), 1.79-1.88 (m, 2H), 1.64-1.77 (m, 2H), 0.90-0.99 (m, 3H); m/z (APCI-pos) M+1=434.2.

Example 222

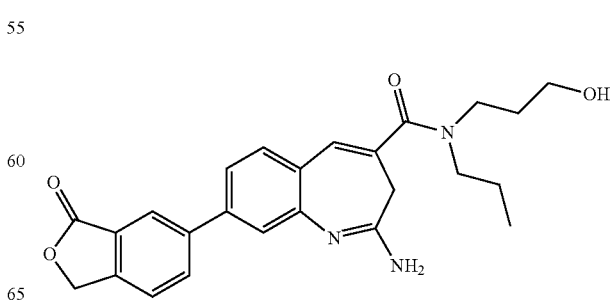

(1E,4E)-2-Amino-N-(3-hydroxypropyl)-8-((3-oxo-1, 3-dihydroisobenzofuran-5-yl)-N-propyl-3H-benzo[b] azepine-4-carboxamide Step A: 6-(4,4,5,5-Tetramethyl-1,3,2-dioxaborolan-2-yl)isobenzofuran-1(3H)-one (67%) was prepared according to Example 224/225, Step C described below, substituting 6-bromoisobenzofuran-1 (3H)-one for 4-(4-bromophenyl)-1,3-dioxolan-2-one.

Step B: (1E,4E)-2-Amino-N-(3-hydroxypropyl)-8-((3-oxo-1,3-dihydroisobenzofuran-5-yl)-N-propyl-3H-benzo[b]azepine-4-carboxamide (36%) was prepared as follows, substituting 6-(4,4,5,5-tetramethyl-1,3,2-dioxaborolan-2-yl)isobenzofuran-1(3H)-one for 4-(ethoxycarbonyl)phenylboronic acid. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (44%) was prepared as follows, substituting tert-butyl (1E,4E)-8-bromo-4-((3-(tert-butyldimethylsilyloxy)propyl)(propyl)carbamoyl)-3H-benzo[b]azepin-2-ylcarbamate for 1E,4E)-2-amino-8-bromo-N,N-dipropyl-3H-benzo[b]azepine-4-carboxamide and 4-(ethoxycarbonyl)phenylboronic acid for 4-(methoxycarbonyl)phenylboronic acid. (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl) benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) was used. $^1$H NMR (400 MHz, DMSO-d$_6$) δ 8.08-8.13 (m, 1H), 8.03-8.06 (m, 1H), 7.74-7.78 (m, 1H), 7.41-7.45 (m, 1H), 7.32-7.36 (m, 2H), 6.91 (br s, 2H), 6.80 (s, 1H), 5.47 (s, 2H), 4.45-4.50 (m, 1H), 53.37-3.48 (m, 2H), 3.28-3.37 (m, 4H, obscured by water peak), 2.75 (s, 2H), 1.66-1.77 (m, 2H), 1.51-1.62 (m, 2H), 0.72-0.91 (m, 3H); m/z (APCI-pos) M+1=434.2.

Example 223

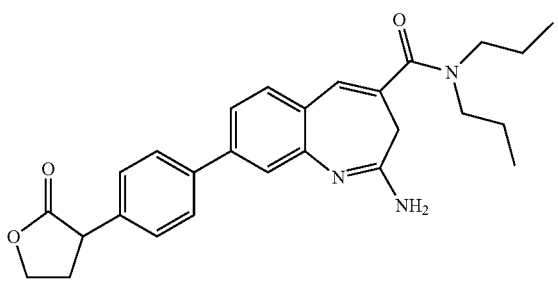 [SMILES: CCCN(CCC)C(=O)C1=Cc2ccc(-c3ccc(C4CCOC4=O)cc3)cc2N=C(N)C1]

(1E,4E)-2-Amino-8-(4-(2-oxotetrahydrofuran-3-yl) phenyl)-N,N-dipropyl-3H-benzo[b]azepine-4-carboxamide Step A 4-Bromophenylacetic acid (1.00 g, 4.65 mmol) was dissolved in 45 mls of dry THF and chilled to −78° C. To this was added LDA (9.30 mls, 18.6 mmol, 2M in THF/heptane), resulting in a dark color, and this mixture was stirred at −78° C. for 20 minutes. (2-bromoethoxy)(tert-butyl)dimethylsilane (1.20 mls, 5.58 mmol) was then added via syringe, and then the cooling bath was removed to allowed the reaction to warm to room temperature. Upon warming, the mixture became an amber color. Once at room temperature, 50 mls of 1N aqueous HCl were then added and the mixture was vigorously stirred for 16 hours, then extracted with EtOAc (2×), extracts washed with 2M aqueous sodium carbonate, dried over sodium sulfate and concentrated to an orange oil. Flash 40 Biotage (40M cartridge, 3:1 Hexane:EtOAc) afforded 211 mgs (19%) of 3-(4-bromophenyl)dihydrofuran-2(3H)-one as an orange oil.

Step B: 3-(4-(4,4,5,5-Tetramethyl-1,3,2-dioxaborolan-2-yl)phenyl)dihydrofuran-2(3H)-one (40%) was prepared according to Example 224/225, Step C described below.

Step C: (1E,4E)-2-Amino-8-(4-(2-oxotetrahydrofuran-3-yl)phenyl)-N,N-dipropyl-3H-benzo[b] azepine-4-carboxamide (9%) was prepared as follows, substituting 3-(4-(4,4,5,5-tetramethyl-1,3,2-dioxaborolan-2-yl)phenyl)dihydrofuran-2 (3H)-one for 4-(methoxycarbonyl)phenylboronic acid. (1E, 4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol, tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. $^1$H NMR (400 MHz, CDCl$_3$) δ 7.64-7.68 (m, 2H), 7.51-7.54 (m, 1H), 7.32-7.39 (m, 4H), 6.84 (s, 1H), 4.48-4.55 (m, 1H), 4.33-4.42 (m, 1H), 3.83-3.90 (m, 1H), 3.41-3.50 (m, 4H), 2.89 (s, 2H), 2.70-2.81 (m, 1H), 2.44-2.56 (m, 1H), 1.59-1.72 (m, 4H), 0.88-0.98 (m, 6H); m/z (APCI-pos) M+1=446.2.

Example 224

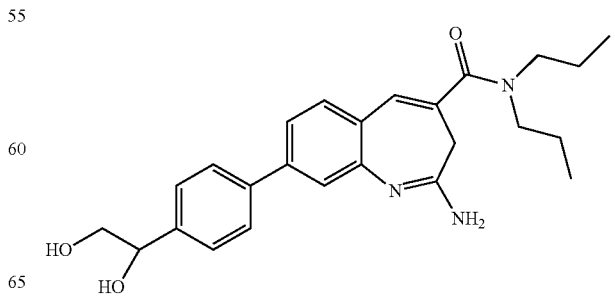

(1E,4E)-2-amino-8-(4-(1,2-dihydroxyethyl)phenyl)-N,N-dipropyl-3H-benzo[b]azepine-4-carboxamide Example 225

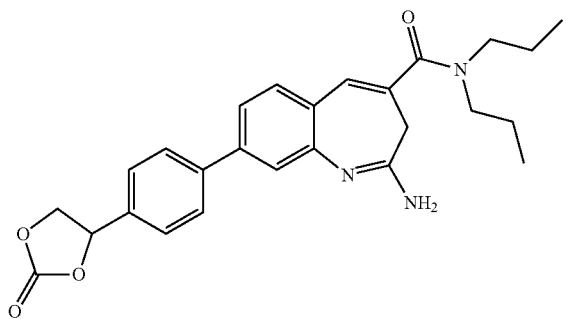 [SMILES: CCCN(CCC)C(=O)C1=Cc2ccc(-c3ccc(C4COC(=O)O4)cc3)cc2N=C(N)C1]

(1E,4E)-2-amino-8-(4-(2-oxo-1,3-dioxolan-4-yl)phenyl)-N,N-dipropyl-3H-benzo[b]azepine-4-carboxamide (1E,4E)-2-amino-8-(4-(1,2-dihydroxyethyl)phenyl)-N,N-dipropyl-3H-benzo[b]azepine-4-carboxamide Step A 4-Bromostyrene (1.00 g, 5.46 mmol) was dissolved in 25 mls of 2:1 water acetone. To this was added 4-methylmorpholine N-oxide (0.704 g, 6.01 mmole) and osmium tetroxide (0.167 g, 0.061 mmole, 2.5% in t-BuOH). This mixture was stirred at room temperature for 16 hours, then diluted with EtOAc, washed once with 1N aq. HCl, once with saturated sodium bicarbonate solution, dried over sodium sulfate and concentrated under reduced pressure. The resulting crude product was purified by Flash 40 Biotage (40M cartridge, 100% EtOAc as the eluant) to give 335 mgs (28%) of 1-(4-bromophenyl)ethane-1,2-diol as a white solid.

Step B 1-(4-bromophenyl)ethane-1,2-diol (0.15 g, 0.69 mmol) was dissolved in 7 mls of dry acetonitrile, followed by the addition of carbonyldiimidazole (0.17 g, 1.04 mmol). This mixture was warmed to 40° C. for 1.5 hours. After cooling to room temperature, the reaction mixture was diluted with EtOAc and washed with saturated ammonium chloride solution, water, dried over sodium sulfate and concentrated under reduced pressure. 10 g Sep Pak purification (1:1 EtOAc:Hexanes) afforded 0.095 g of 4-(4-bromophenyl)-1,3-dioxolan-2-one (57%) as a white solid.

Step C 4-(4-Bromophenyl)-1,3-dioxolan-2-one (0.093 g, 0.383 mmol), 4,4,4',4',5,5,5',5'-octamethyl-2,2'-bi(1,3,2-dioxaborolane) (0.117 g, 0.459 mmol), potassium acetate (0.113 g, 1.15 mmol) and dichloro 1,1'-bis(diphenylphosphino)ferrocene palladium (II) dichloromethane adduct (0.0094 g, 0.012 mmol) were combined in dioxane and warmed to 100° C. for 3 hours. The mixture was then diluted with water, extracted twice with EtOAc; extracts dried over sodium sulfate and concentrated under reduced pressure. 10 g Sep Pak purification (100% DCM as the eluant) afforded 0.070 g of 4-(4-(4,4,5,5-tetramethyl-1,3,2-dioxaborolan-2-yl)phenyl)-1,3-dioxolan-2-one (63%) as a white solid.

Step D

Reaction of (1E,4E)-2-amino-8-bromo-N,N-dipropyl-3H-benzo[b]azepine-4-carboxamide and 4-(4-(4,4,5,5-tetramethyl-1,3,2-dioxaborolan-2-yl)phenyl)-1,3-dioxolan-2-one as follows yielded (1E,4E)-2-amino-8-(4-(2-oxo-1,3-dioxolan-4-yl)phenyl)-N,N-dipropyl-3H-benzo[b]azepine-4-carboxamide (9%). (1E,4E)-2-amino-8-bromo-N,N-dipropyl-3H-benzo[b]azepine-4-carboxamide (75.0 mgs, 0.206 mmol), 4-(methoxycarbonyl)phenylboronic acid (55.6 mgs, 0.309 mmol), tetrakis(triphenylphosphine)palladium(0) (23.8 mgs, 0.021 mmol), 2M aqueous potassium carbonate (0.309 ml, 0.618 mmol) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) was then used. $^1$H NMR (400 MHz, DMSO-$d_6$) δ 7.74-7.80 (m, 2H), 7.55-7.60 (m, 2H), 7.26-7.42 (m, 3H), 6.78 (s, 1H), 5.89-5.96 (m, 1H), 4.88-4.95 (m, 1H), 4.45-4.52 (m, 1H), 2.78 (s, 2H), 1.50-1.63 (m, 4H), 0.71-0.93 (m, 6H); m/z (APCI-pos) M+1=448.2. (1E,4E)-2-amino-8-(4-(1,2-dihydroxyethyl)phenyl)-N,N-dipropyl-3H-benzo[b]azepine-4-carboxamide (19%) was obtained as the more polar product. (19%). $^1$H NMR (400 MHz, DMSO-$d_6$) δ 7.59-7.64 (m, 2H), 7.39-7.44 (m, 2H), 7.33-7.38 (m, 1H), 7.26-7.28 (m, 1H), 7.20-7.24 (m, 1H), 6.84 (br s, 1H), 6.74 (s, 1H), 5.23-5.27 (m, 1H), 4.71-4.75 (m, 1H), 4.54-4.62 (m, 1H), 3.44-3.50 (m, 2H), 3.28-3.35 (m, 4H), 2.74 (s, 2H), 1.51-1.61 (m, 4H), 0.73-0.90 (m, 6H); m/z (APCI-pos) M+1=422.2.

Example 226

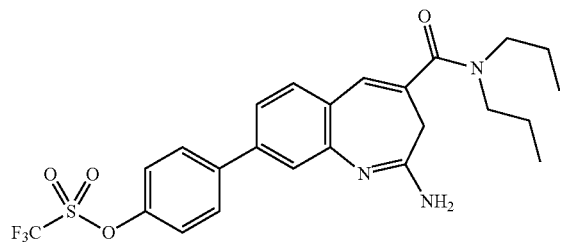 [SMILES: CCCN(CCC)C(=O)C1=Cc2ccc(-c3ccc(OS(=O)(=O)C(F)(F)F)cc3)cc2N=C(N)C1]

4-((1E,4E)-2-amino-4-(dipropylcarbamoyl)-3H-benzo[b]azepin-8-yl)phenyl trifluoromethanesulfonate Step A: Preparation of tert-butyl (1E,4E)-4-(dipropylcarbamoyl)-8-(4-hydroxyphenyl)-3H-benzo[b]azepin-2-ylcarbamate The title compound was prepared by these procedures using tert-butyl (1E,4E)-8-bromo-4-(dipropylcarbamoyl)-3H-benzo[b]azepin-2-ylcarbamate and 4-hydroxyphenylboronic acid. Preparation of tert-butyl (1E,4E)-8-(4-(dimethylcarbamoyl)phenyl)-4-(dipropylcarbamoyl)-3H-benzo[b]azepin-2-ylcarbamate: To Na$_2$CO$_3$ (129 mg, 1.214 mmol) in a 50 mL round-bottom flask was added water (3.7 mL) was bubbled with N₂ for 10 min. To this mixture was added tert-butyl (1E,4E)-8-bromo-4-(dipropylcarbamoyl)-3H-benzo[b]azepin-2-ylcarbamate (200 mg, 0.40 mmol) in EtOH (4.9 mL) at room temperature. The resulting mixture was bubbled with N₂ for 10 min. Pd(OAc)₂ (9.3 mg, 0.040 mmol) and 4,4'-(phenylphosphinidene)bisbenzenesulfonic acid dipotassium hydrate (45 mg, 0.081 mmol) were added. The resulting mixture was warmed to 65° C. with N₂ bubbling. To this mixture was added a solution of 4-(dimethylcarbamoyl)phenylboronic acid (97 mg, 0.49 mmol) in EtOH (0.6 mL). The resulting mixture was stirred at 65° C. for 1 h. The reaction mixture was cooled to room temperature and concentrated under reduced pressure to give the crude material that was diluted with water (5 mL) and EtOAc (10 mL). The mixture was filtered through GF/F filter. The aqueous layer was separated and extracted with EtOAc (10 mL). The combined organic layers were washed with brine (10 mL), dried over MgSO₄, filtered, and concentrated under reduced pressure to give the crude product that was purified by silica gel flash column chromatography (CH₂Cl₂ to 2% MeOH in CH₂Cl₂). MS APCI (+) m/z 478 (M+1) detected.

Step B: Preparation of 4-((1E,4E)-2-(tert-butoxycarbonylamino)-4-(dipropylcarbamoyl)-3H-benzo[b]azepin-8-yl)phenyl trifluoromethanesulfonate To a solution of tert-butyl (1E,4E)-4-(dipropylcarbamoyl)-8-(4-hydroxyphenyl)-3H-benzo[b]azepin-2-ylcarbamate (699 mg, 1.30 mmol) and 1,1,1-trifluoro-N-phenyl-N-(trifluoromethylsulfonyl)methanesulfonamide (698 mg, 1.95 mmol) in CH₂Cl₂ (7 mL) was added TEA (0.27 ml, 1.95 mmol) at room temperature. After stirring for 23 h at room temperature, the reaction mixture was diluted with CH₂Cl₂ (25 mL) and washed with saturated aq NaHCO₃ (15 mL) followed by brine (15 mL). The organic layer was dried over MgSO₄, filtered, and concentrated under reduced pressure to give the crude material that was purified by silica gel flash column chromatography (10 to 30% EtOAc in hexanes, gradient) to afford 526 mg (66%) of 4-((1E,4E)-2-(tert-butoxycarbonylamino)-4-(dipropylcarbamoyl)-3H-benzo[b]azepin-8-yl)phenyl trifluoromethanesulfonate. MS APCI (+) m/z 610 (M+1) detected.

Step C: Preparation of 4-((1E,4E)-2-amino-4-(dipropylcarbamoyl)-3H-benzo[b]azepin-8-yl)phenyl trifluoromethanesulfonate The title compound was prepared by these procedures. Preparation of (1E,4E)-2-amino-N-propyl-8-(4-(pyrrolidine-1-carbonyl)phenyl)-3H-benzo[b]azepine-4-carboxamide: To a solution of tert-butyl (1E,4E)-4-(propylcarbamoyl)-8-(4-(pyrrolidine-1-carbonyl)phenyl)-3H-benzo[b]azepin-2-ylcarbamate (450 mg, 0.87 mmol) in CH₂Cl₂ (5 mL) was added 2,2,2-trifluoroacetic acid (1.36 mL, 17.4 mmol) at 0° C. The reaction mixture was warmed to room temperature and stirred for 2 h. The reaction mixture was concentrated under reduced pressure to give the crude material that was diluted with CH₂Cl₂ (10 mL) and saturated aq NaHCO₃ (15 mL) again. The resulting mixture was stirred for 30 min at room temperature. The aqueous layer was separated and extracted with CH₂Cl₂ (1×10 mL). The combined organic layers were washed with saturated aq NaHCO₃ (2×10 mL) and brine (1×10 mL), dried over MgSO₄, filtered, and concentrated under reduced pressure to give the crude material again that was purified by silica gel flash column chromatography (1 to 5% MeOH in CH₂Cl₂, gradient). MS APCI (+) m/z 510 (M+1) detected; ¹H-NMR (400 MHz, CDCl₃) δ 7.69-7.72 (m, 2H), 7.45 (d, 1H), 7.33-7.37 (m, 3H), 7.24-7.26 (m, 1H), 6.83 (s, 1H), 3.47 (br s, 4H), 2.81 (s, 2H), 1.62-1.72 (m, 4H), 0.94 (t, 6H); ¹⁹F-NMR (376 MHz, CDCl₃) δ −73.2.

Example 227

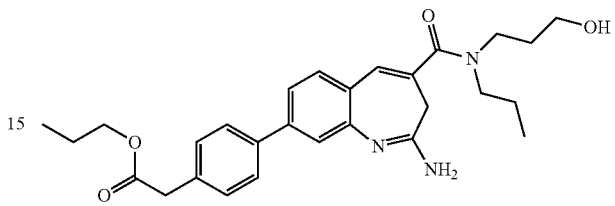

Propyl 2-(4-((1E,4E)-2-amino-4-((3-hydroxypropyl)(propyl)carbamoyl)-3H-benzo[b]azepin-8-yl)phenyl)acetate Step A Propyl 2-(4-(4,4,5,5-tetramethyl-1,3,2-dioxaborolan-2-yl)phenyl)acetate (43%) was prepared according to Example 192, Step A, substituting propanol for ethanol.

Step B

Propyl 2-(4-((1E,4E)-2-amino-4-((3-hydroxypropyl)(propyl)carbamoyl)-3H-benzo[b]azepin-8-yl)phenyl)acetate (10%) was prepared as follows:

Step 1 tert-butyl (1E,4E)-8-bromo-4-((3-(tert-butyldimethylsilyloxy)propyl)(propyl)carbamoyl)-3H-benzo[b]azepin-2-ylcarbamate, propyl 2-(4-(4,4,5,5-tetramethyl-1,3,2-dioxaborolan-2-yl)phenyl)acetate (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded propyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate.

Step 2

Propyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/ 0.5% NH4OH) afforded propyl 2-(4-((1E,4E)-2-amino-4-((3-hydroxypropyl)(propyl)carbamoyl)-3H-benzo[b]azepin-8-yl)phenyl)acetate. 1H NMR (400 MHz, DMSO-d6) δ 7.60-7.68 (m, 2H), 7.20-7.41 (m, 5H), 6.73-6.85 (m, 3H), 4.42-4.52 (m, 1H), 4.05-4.16 (m, 2H), 3.71 (s, 2H), 3.24-3.52 (m, 6H, partially obscured by water peak), 2.75 (s, 2H), 1.66-1.78 (m, 2H), 1.50-1.65 (m, 2H), 1.15-1.23 (m, 3H), 0.75-0.92 (m, 3H); m/z (APCI-pos) M+1=464.2.

Example 228

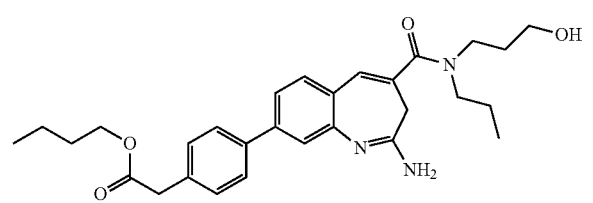 [SMILES: CCCCOC(=O)Cc1ccc(-c2ccc3c(c2)N=C(N)CC(C(=O)N(CCC)CCCO)=C3)cc1]

Butyl 2-(4-((1E,4E)-2-amino-4-((3-hydroxypropyl) (propyl)carbamoyl)-3H-benzo[b]azepin-8-yl)phenyl) acetate Step A: Butyl 2-(4-(4,4,5,5-tetramethyl-1,3,2-dioxaborolan-2-yl)phenyl)acetate (40%) was prepared according to Example 192, Step A, substituting 1-butanol for ethanol.

Step B: Butyl 2-(4-((1E,4E)-2-amino-4-((3-hydroxypropyl)(propyl)carbamoyl)-3H-benzo[b]azepin-8-yl)phenyl)acetate (8%) was prepared as follows:

Step 1 tert-butyl (1E,4E)-8-bromo-4-((3-(tert-butyldimethylsilyloxy)propyl)(propyl)carbamoyl)-3H-benzo[b]azepin-2-ylcarbamate, butyl 2-(4-(4,4,5,5-tetramethyl-1,3,2-dioxaborolan-2-yl)phenyl)acetate (1.5 equiv), tetrakis (triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded butyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl) acetate.

Step 2

Butyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH4OH) afforded butyl 2-(4-((1E,4E)-2-amino-4-((3-hydroxypropyl)(propyl)carbamoyl)-3H-benzo[b]azepin-8-yl) phenyl)acetate. 1H NMR (400 MHz, CDCl3) δ 7.59-7.63 (m, 2H), 7.50-7.51 (m, 1H), 7.34-7.38 (m 2H), 7.32-7.34 (m, 2H), 6.88 (s, 2H), 4.09-4.14 (m, 2H), 3.58-3.68 (m, 6H), 3.45-3.51 (m, 2H), 2.87 (s, 2H), 1.79-1.88 (m, 2H), 1.57-1.76 (m, 4H), 1.30-1.42 (m, 2H), 0.89-0.96 (m, 6H); m/z (APCI-pos) M+1=492.2.

Example 229

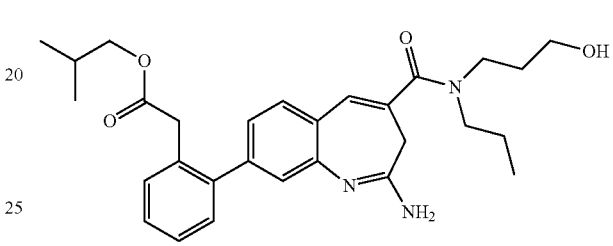

Isobutyl 2-(2-((1E,4E)-2-amino-4-((3-hydroxypropyl)(propyl)carbamoyl)-3H-benzo[b]azepin-8-yl) phenyl)acetate Step A 2-(2-Bromophenyl)acetic acid (1.00 g, 4.65 mmol) was dissolved in 45 mls of dry dichloromethane. To this solution was added oxalyl chloride (0.609 ml, 6.98 mmol), followed by a drop of DMF. This mixture was stirred for two hours at room temperature, then concentrated under reduced pressure. The resulting residue was then re-dissolved in dry dichloromethane (45 mls), and 2 mls of 2-methylpropan-1-ol were then added and the mixture stirred at room temperature for 1.5 hours, then concentrated to isobutyl 2-(2-bromophenyl)acetate (100%).

Step B: Isobutyl 2-(2-(4,4,5,5-tetramethyl-1,3,2-dioxaborolan-2-yl)phenyl)acetate (49%) was prepared according to Example 224/225, Step C, substituting isobutyl 2-(2-bromophenyl)acetate for 4-(4-bromophenyl)-1,3-dioxolan-2-one.

Step C: Isobutyl 2-(2-((1E,4E)-2-amino-4-((3-hydroxypropyl)(propyl)carbamoyl)-3H-benzo[b]azepin-8-yl)phenyl)acetate (30%) was prepared as follows:

Step 1 tert-butyl (1E,4E)-8-bromo-4-((3-(tert-butyldimethylsilyloxy)propyl)(propyl)carbamoyl)-3H-benzo[b]azepin-2-ylcarbamate, isobutyl 2-(2-bromophenyl)acetate (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded isobutyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate.

Step 2

Isobutyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) afforded isobutyl 2-(4-((1E,4E)-2-amino-4-((3-hydroxypropyl)(propyl)carbamoyl)-3H-benzo[b]azepin-8-yl)phenyl)acetate. 1H NMR (400 MHz, CDCl3) δ 7.27-7.39 (m, 5H), 7.19-7.21 (m, 1H), 7.01-7.06 (m, 1H), 6.87 (s, 1H), 3.80-3.85 (m, 2H), 3.58-3.69 (m, 6H), 3.46-3.53 (m, 2H), 2.82 (s, 2H), 1.80-1.89 (m, 3H), 1.66-1.75 (m, 2H), 0.90-0.98 (m, 3H), 0.81-0.87 (m, 6H); m/z (APCI-pos) M+1=492.3.

Example 230

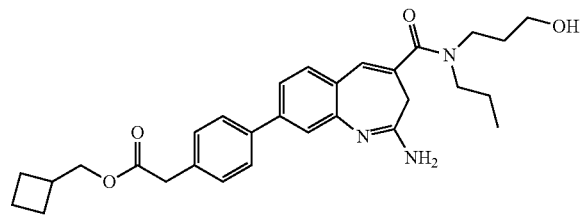 [SMILES: CCCN(CCCO)C(=O)C1=Cc2ccc(-c3ccc(CC(=O)OCC4CCC4)cc3)cc2N=C(N)C1]

Cyclobutylmethyl 2-(4-((1E,4E)-2-amino-4-((3-hydroxypropyl)(propyl)carbamoyl)-3H-benzo[b]azepin-8-yl)phenyl)acetate Step A: Cyclobutylmethyl 2-(4-(4,4,5,5-tetramethyl-1,3,2-dioxaborolan-2-yl)phenyl)acetate (100%) was prepared according to Example 192, Step A, substituting cyclobutylmethanol for ethanol.

Step B: Cyclobutylmethyl 2-(4-((1E,4E)-2-amino-4-((3-hydroxypropyl)(propyl)carbamoyl)-3H-benzo[b]azepin-8-yl)phenyl)acetate (10%) was prepared as follows:

Step 1 tert-butyl (1E,4E)-8-bromo-4-((3-(tert-butyldimethylsilyloxy)propyl)(propyl)carbamoyl)-3H-benzo[b]azepin-2-yl-carbamate, cyclobutylmethyl 2-(4-(4,4,5,5-tetramethyl-1,3,2-dioxaborolan-2-yl)phenyl)acetate (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded cyclobutylmethyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)benzoate.

Step 2

Cyclobutylmethyl 4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) afforded cyclobutylmethyl 2-(4-((1E,4E)-2-amino-4-((3-hydroxypropyl)(propyl)carbamoyl)-3H-benzo[b]azepin-8-yl)phenyl)acetate. 1H NMR (400 MHz, CDCl3) δ 7.59-7.64 (m, 2H), 7.49-7.51 (m, 1H), 7.29-7.39 (m, 4H), 6.87 (s, 1H), 4.06-4.12 (m, 2H), 3.57-3.70 (m, 6H), 3.44-3.53 (m, 2H), 2.83 (s, 2H), 2.56-2.67 (m, 1H), 1.96-2.07 (m, 2H), 1.66-1.92 (m, 8H), 0.91-0.97 (m, 3H); m/z (APCI-pos) M+1=504.2.

Example 231

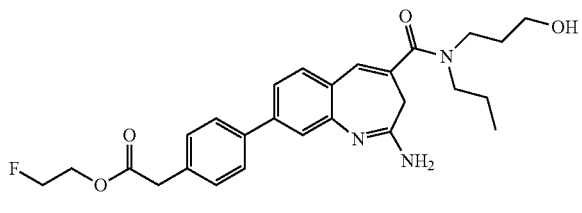 [SMILES: CCCN(CCCO)C(=O)C1=Cc2ccc(-c3ccc(CC(=O)OCCF)cc3)cc2N=C(N)C1]

2-Fluoroethyl 2-(4-((1E,4E)-2-amino-4-((3-hydroxypropyl)(propyl)carbamoyl)-3H-benzo[b]azepin-8-yl)phenyl)acetate Step A: 2-Fluoroethyl 2-(4-(4,4,5,5-tetramethyl-1,3,2-dioxaborolan-2-yl)phenyl)acetate (35%) was prepared according to Example 192, Step A, substituting 2-fluoroethanol for ethanol.

Step B: 2-Fluoroethyl 2-(4-((1E,4E)-2-amino-4-((3-hydroxypropyl)(propyl)carbamoyl)-3H-benzo[b]azepin-8-yl)phenyl)acetate (25%) was prepared according as follows:

Step 1 tert-butyl (1E,4E)-8-bromo-4-((3-(tert-butyldimethylsilyloxy)propyl)(propyl)carbamoyl)-3H-benzo[b]azepin-2-yl-carbamate, 2-fluoroethyl 2-(4-(4,4,5,5-tetramethyl-1,3,2-dioxaborolan-2-yl)phenyl)acetate (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded 2-fluoroethyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate.

Step 2

2-Fluoroethyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) afforded 0.012 g (35%) of 2-fluoroethyl 2-(4-((1E,4E)-2-amino-4-((3-hydroxypropyl)(propyl)carbamoyl)-3H-benzo[b]azepin-8-yl)phenyl)acetate. 1H NMR (400 MHz, CDCl3) δ 7.60-7.65 (m, 2H), 7.49-7.51 (m, 1H), 7.29-7.39 (m, 4H), 6.87 (s, 1H), 4.66-4.69 (m, 1H), 4.54-4.58 (m, 1H), 4.39-4.43 (m, 1H), 4.32-4.36 (m, 1H), 3.73 (s, 2H), 3.58-3.68 (m, 4H), 3.43-3.52 (m, 2H), 1.78-1.87 (m, 2H), 1.65-1.75 (m, 2H), 0.90-0.96 (m, 3H); m/z (APCI-pos) M+1=482.2.

Example 232

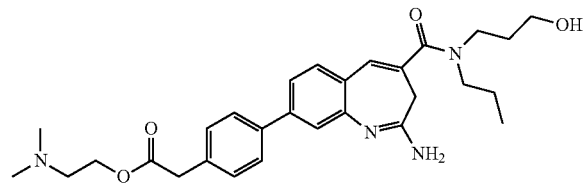 [SMILES: CCCN(CCCO)C(=O)C1=Cc2ccc(-c3ccc(CC(=O)OCCN(C)C)cc3)cc2N=C(N)C1]

2-(Dimethylamino)ethyl 2-(4-((1E,4E)-2-amino-4-((3-hydroxypropyl)(propyl)carbamoyl)-3H-benzo[b]azepin-8-yl)phenyl)acetate Step A: 2-(Dimethylamino)ethyl 2-(4-(4,4,5,5-tetramethyl-1,3,2-dioxaborolan-2-yl)phenyl)acetate (60%) was prepared according to Example 192, Step A, substituting 2-(dimethylamino)ethanol for ethanol.

Step B: 2-(Dimethylamino)ethyl 2-(4-((1E,4E)-2-amino-4-((3-hydroxypropyl)(propyl)carbamoyl)-3H-benzo[b]azepin-8-yl)phenyl)acetate (5%) was prepared according as follows:

Step 1 tert-butyl (1E,4E)-8-bromo-4-((3-(tert-butyldimethylsilyloxy)propyl)(propyl)carbamoyl)-3H-benzo[b]azepin-2-yl-carbamate, 2-(dimethylamino)ethyl 2-(4-(4,4,5,5-tetramethyl-1,3,2-dioxaborolan-2-yl)phenyl)acetate (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded 2-(dimethylamino)ethyl-2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate.

Step 2

2-(dimethylamino)ethyl-2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) afforded 2-(dimethylamino)ethyl-2-(4-((1E,4E)-2-amino-4-((3-hydroxypropyl)(propyl)carbamoyl)-3H-benzo[b]azepin-8-yl)phenyl)acetate. 1H NMR (400 MHz, CDCl3) δ 7.59-7.64 (m, 2H), 7.48-7.51 (m, 1H), 7.28-7.38 (m, 4H), 6.87 (s, 1H), 4.19-4.24 (m, 2H), 3.58-3.74 (m, 6H), 3.44-3.52 (m, 2H), 2.84 (s, 2H), 2.54-2.61 (m, 2H), 2.27 (s, 6H), 1.79-1.86 (m, 2H), 1.65-1.76 (m, 2H), 0.89-0.97 (m, 3H); m/z (APCI-pos) M+1=507.2.

Example 233

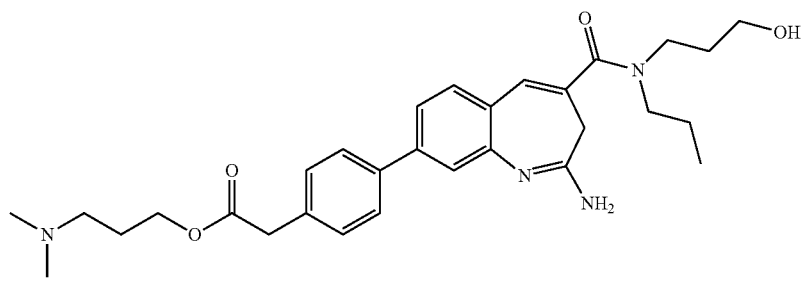 [SMILES: CCCN(CCCO)C(=O)C1=Cc2ccc(-c3ccc(CC(=O)OCCCN(C)C)cc3)cc2N=C(N)C1]

3-(Dimethylamino)propyl 2-(4-((1E,4E)-2-amino-4-((3-hydroxypropyl)(propyl)carbamoyl)-3H-benzo[b]azepin-8-yl)phenyl)acetate Step A: 3-(Dimethylamino)propyl 2-(4-(4,4,5,5-tetramethyl-1,3,2-dioxaborolan-2-yl)phenyl)acetate (45%) was prepared according to Example 192, Step A, substituting 3-(dimethylamino)propan-1-ol for ethanol.

Step B: 3-(Dimethylamino)propyl 2-(4-((1E,4E)-2-amino-4-((3-hydroxypropyl)(propyl)carbamoyl)-3H-benzo[b]azepin-8-yl)phenyl)acetate (6%) was prepared as follows:

Step 1 tert-butyl (1E,4E)-8-bromo-4-((3-(tert-butyldimethylsilyloxy)propyl)(propyl)carbamoyl)-3H-benzo[b]azepin-2-ylcarbamate, 3-(dimethylamino)propyl 2-(4-(4,4,5,5-tetramethyl-1,3,2-dioxaborolan-2-yl)phenyl)acetate (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded 3-(dimethylamino)propyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate.

Step 2

3-(dimethylamino)propyl 2-(4-((1E,4E)-2-(tert-butoxycarbonylamino)-4-((3-(tert-butyldimethylsilyloxy)propyl)(propyl)carbamoyl)-3H-benzo[b]azepin-8-yl)phenyl)acetate was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) afforded 3-(dimethylamino)propyl 2-(4-((1E,4E)-2-amino-4-((3-hydroxypropyl)(propyl)carbamoyl)-3H-benzo[b]azepin-8-yl)phenyl)acetate. 1H NMR (400 MHz, CDCl3) δ 7.57-7.65 (m, 2H), 7.46-7.51 (m, 1H), 7.28-7.40 (m, 4H), 6.87 (s, 2H), 4.07-4.21 (m, 2H), 3.56-3.71 (m, 6H), 3.40-3.54 (m, 2H), 2.82 (s, 2H), 2.26-2.36 (m, 2H), 2.20 (s, 6H), 1.59-1.87 (m, 6H), 0.86-0.99 (m, 3H); m/z (APCI-pos) M+1=521.3.

Example 234

Isobutyl 2-(4-((1E,4E)-2-amino-4-((2-amino-2-oxoethyl)(propyl)carbamoyl)-3H-benzo[b]azepin-8-yl)phenyl)acetate Step A: Isobutyl 2-(4-((1E,4E)-2-amino-4-((2-amino-2-oxoethyl)(propyl)carbamoyl)-3H-benzo[b]azepin-8-yl)phenyl)acetate (23%) was prepared as described below in Steps 1 and 2, except for substituting isobutyl 2-(4-(4,4,5,5-tetramethyl-1,3,2-dioxaborolan-2-yl)phenyl)acetate for 4-(ethoxycarbonyl)phenylboronic acid and tert-butyl (1E,4E)-4-((2-amino-2-oxoethyl)(propyl)carbamoyl)-8-bromo-3H-benzo[b]azepin-2-ylcarbamate for tert-butyl (1E,4E)-8-bromo-4-((3-(tert-butyldimethylsilyloxy)propyl)(propyl)carbamoyl)-3H-benzo[b]azepin-2-ylcarbamate.

Step 1 tert-butyl (1E,4E)-8-bromo-4-((3-(tert-butyldimethylsilyloxy)propyl)(propyl)carbamoyl)-3H-benzo[b]azepin-2-ylcarbamate, 4-(ethoxycarbonyl)phenylboronic acid (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate.

Step 2

Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH$_4$OH) afforded 0.012 g (35%) of ethyl 4-((1E,4E)-2-amino-4-((3-hydroxypropyl)(propyl)carbamoyl)-3H-benzo[b]azepin-8-yl)benzoate.

1H NMR (400 MHz, DMSO-d6) δ 7.59-7.66 (m, 2H), 7.32-7.38 (m, 2H), 7.22-7.30 (m, 2H), 7.07-7.13 (m, 1H), 3.92-4.00 (m, 2H), 3.83-3.87 (m, 2H), 3.73 (s, 2H), 2.75 (s, 2H), 1.82-1.92 (m, 1H), 1.51-1.61 (m, 2H), 0.84-0.89 (m, 9H); m/z (APCI-pos) M+1=491.2.

Example 235

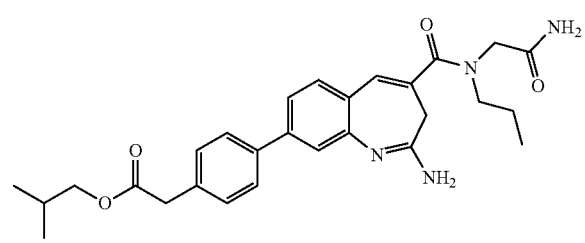 [SMILES: CCCN(CC(N)=O)C(=O)C1=Cc2ccc(-c3ccc(CC(=O)OCC(C)C)cc3)cc2N=C(N)C1]

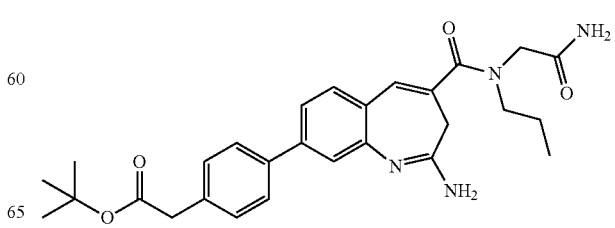

tert-Butyl 2-(4-((1E,4E)-2-amino-4-((2-amino-2-oxoethyl)(propyl)carbamoyl)-3H-benzo[b]azepin-8-yl)phenyl)acetate

Step A: 2-(4-(4,4,5,5-Tetramethyl-1,3,2-dioxaborolan-2-yl)phenyl)acetic acid (0.250 g, 0.954 mmol) was dissolved in 10 mls of dry THF. To this solution was added (Z)-tert-butyl N,N'-diisopropylcarbamimidate (3.82 g, 19.08 mmol) and the mixture was allowed to stir at room temperature for 16 hours. The mixture was then filtered, filtrate concentrated under reduced pressure and purified by a 50 g Snap cartridge (Biotage, 10% EtOAc/Hexanes) to give 280 mgs (92%) of tert-butyl 2-(4-(4,4,5,5-tetramethyl-1,3,2-dioxaborolan-2-yl)phenyl)acetate as a thick oil.

Step B: tert-Butyl 2-(4-((1E,4E)-2-amino-4-((2-amino-2-oxoethyl)(propyl)carbamoyl)-3H-benzo[b]azepin-8-yl)phenyl)acetate (32%) was prepared as described below in Steps 1 and 2, except for substituting isobutyl tert-butyl 2-(4-(4,4,5,5-tetramethyl-1,3,2-dioxaborolan-2-yl)phenyl)acetate for 4-(ethoxycarbonyl)phenylboronic acid and (1E,4E)-2-amino-N-(2-amino-2-oxoethyl)-8-bromo-N-propyl-3H-benzo[b]azepine-4-carboxamide for tert-butyl (1E,4E)-8-bromo-4-((3-(tert-butyldimethylsilyloxy)propyl)(propyl)carbamoyl)-3H-benzo[b]azepin-2-ylcarbamate.

Step 1 tert-butyl (1E,4E)-8-bromo-4-((3-(tert-butyldimethylsilyloxy)propyl)(propyl)carbamoyl)-3H-benzo[b]azepin-2-ylcarbamate, 4-(ethoxycarbonyl)phenylboronic acid (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate.

Step 2

Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH₄OH) afforded 0.012 g (35%) of ethyl 4-((1E,4E)-2-amino-4-((3-hydroxypropyl)(propyl)carbamoyl)-3H-benzo[b]azepin-8-yl)benzoate.
1H NMR (400 MHz, DMSO-d6) δ 7.50-7.65 (m, 2H), 7.23-7.36 (m, 5H), 7.09-7.14 (br s, 1H), 6.84-6.91 (br s, 1H), 3.92-4.00 (br s, 2H), 3.61 (s, 2H), 3.51 (s, 1H), 2.77 (br s, 2H), 1.51-1.61 (m, 2H), 1.42 (s, 9H), 0.73-0.91 (m, 3H); m/z (APCI-pos) M+1=491.2.

Example 236

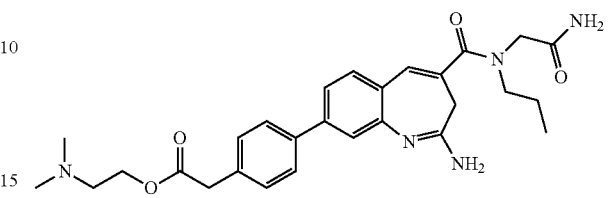

2-(Dimethylamino)ethyl 2-(4-((1E,4E)-2-amino-4-((2-amino-2-oxoethyl)(propyl)carbamoyl)-3H-benzo[b]azepin-8-yl)phenyl)acetate

Step A: 2-(Dimethylamino)ethyl 2-(4-((1E,4E)-2-amino-4-((2-amino-2-oxoethyl)(propyl)carbamoyl)-3H-benzo[b]azepin-8-yl)phenyl)acetate (19%) was prepared according as described below in Steps 1 and 2, except for substituting 2-(dimethylamino)ethyl 2-(4-(4,4,5,5-tetramethyl-1,3,2-dioxaborolan-2-yl)phenyl)acetate for 4-(ethoxycarbonyl)phenylboronic acid and (1E,4E)-2-amino-N-(2-amino-2-oxoethyl)-8-bromo-N-propyl-3H-benzo[b]azepine-4-carboxamide for tert-butyl (1E,4E)-8-bromo-4-((3-(tert-butyldimethylsilyloxy)propyl)(propyl)carbamoyl)-3H-benzo[b]azepin-2-ylcarbamate.

Step 1 tert-butyl (1E,4E)-8-bromo-4-((3-(tert-butyldimethylsilyloxy)propyl)(propyl)carbamoyl)-3H-benzo[b]azepin-2-ylcarbamate, 4-(ethoxycarbonyl)phenylboronic acid (1.5 equiv), tetrakis(triphenylphosphine)palladium(0), 2M aqueous potassium carbonate (3 equiv) were combined in 2 mls of acetonitrile in a microwave reaction vial. This mixture was heated in a microwave to 100° C. for 30 minutes. The mixture was then diluted with EtOAc, washed twice with brine, dried over sodium sulfate, and concentrated under reduced pressure. Preparative thin layer chromatography (2×0.5 mm plates, 7% MeOH/DCM) afforded ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate.

Step 2

Ethyl 4-((1E,4E)-2-(tert-butoxycarbonylamino)-4-((3-(tert-butyldimethylsilyloxy)propyl)(propyl)carbamoyl)-3H-benzo[b]azepin-8-yl)benzoate (0.050 g, 0.075 mmol) was dissolved in 2 mls of dichloromethane and 0.5 ml of TFA. After about one hour, the mixture was concentrated under reduced pressure and the resulting residue was then re-dissolved in dichloromethane and 1 ml of concentrated ammonium hydroxide added and the mixture vigorously stirred for 15 minutes. This mixture was then diluted with water, extracted with dichloromethane (2×), extracts dried over sodium sulfate and concentrated under reduced pressure. Preparative thin layer chromatography (2×0.5 mm plates, 10% MeOH/DCM/0.5% NH₄OH) afforded 0.012 g (35%) of ethyl 4-((1E,4E)-2-amino-4-((3-hydroxypropyl)(propyl)carbamoyl)-3H-benzo[b]azepin-8-yl)benzoate.

1H NMR (400 MHz, DMSO-d6) δ 7.60-7.64 (m, 2H), 7.33-7.37 (m, 2H), 7.26-7.28 (m, 1H), 7.21-7.25 (m, 1H), 7.11 (br s, 1H), 6.75-6.90 (br m, 3H), 4.11-4.16 (m, 2H), 3.96 (br s, 2H), 3.71 (s, 2H), 3.51 (s, 2H), 2.73 (s, 2H), 2.16 (s, 6H), 1.50-1.62 (m, 2H), 0.75-0.91 (m, 3H); m/z (APCI-pos) M+1=506.2.

Example 237

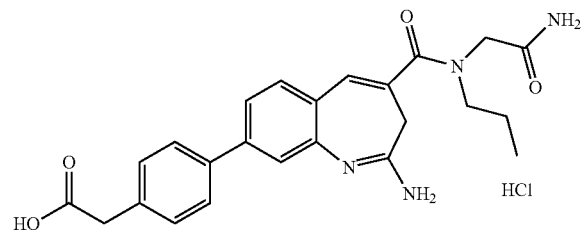 [SMILES: CCCN(CC(N)=O)C(=O)C1=Cc2ccc(-c3ccc(CC(=O)O)cc3)cc2N=C(N)C1 ; Cl]

2-(4-((1E,4E)-2-Amino-4-((2-amino-2-oxoethyl)(propyl)carbamoyl)-3H-benzo[b]azepin-8-yl)phenyl)acetic acid hydrochloride Step A: tert-Butyl 2-(4-((1E,4E)-2-amino-4-((2-amino-2-oxoethyl)(propyl)carbamoyl)-3H-benzo[b]azepin-8-yl)phenyl)acetate (0.037 g, 0.0754 mmol) was dissolved in 1 ml of dioxane and chilled to 0° C. HCl gas was bubbled in for 15 minutes, reaction vessel sealed tightly and the mixture was allowed to warm to room temperature overnight. The gas pressure was carefully released and the mixture was concentrated to 2-(4-((1E,4E)-2-amino-4-((2-amino-2-oxoethyl)(propyl)carbamoyl)-3H-benzo[b]azepin-8-yl)phenyl)acetic acid hydrochloride (100%). m/z (APCI-pos) M+1=435.1.

Example 238

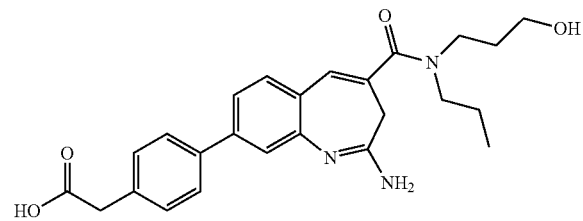 [SMILES: CCCN(CCCO)C(=O)C1=Cc2ccc(-c3ccc(CC(=O)O)cc3)cc2N=C(N)C1]

2-(4-((1E,4E)-2-Amino-4-((3-hydroxypropyl)(propyl)carbamoyl)-3H-benzo[b]azepin-8-yl)phenyl)acetic acid Step A: 2-(4-((1E,4E)-2-Amino-4-((3-hydroxypropyl)(propyl)carbamoyl)-3H-benzo[b]azepin-8-yl)phenyl)acetic acid (8%) %) was prepared as described below in Step 1, except for substituting benzyl 2-(4-((1E,4E)-2-amino-4-((3-hydroxypropyl)(propyl)carbamoyl)-3H-benzo[b]azepin-8-yl)phenyl)acetate for benzyl 4-((1E,4E)-2-amino-4-(dipropylcarbamoyl)-3H-benzo[b]azepin-8-yl)benzoate.

Step 1

Benzyl 4-((1E,4E)-2-amino-4-(dipropylcarbamoyl)-3H-benzo[b]azepin-8-yl)benzoate (0.025 g, 0.0504 mmol) was suspended in 1 ml of methanol, and 25 mgs of 10% Pd/C (Degussa type) was added and the mixture was hydrogenated under a balloon of hydrogen for one hour. This mixture was then filtered through GF/F filter paper, and the filtrate was concentrated to 16 mgs of 4-((1E,4E)-2-amino-4-(dipropylcarbamoyl)-3H-benzo[b]azepin-8-yl)benzoic acid (78%).

m/z (APCI-pos) M+1=436.2.

Example 2

HEK/TLR Assays

The activity of the compounds of this invention may be determined by the following assays.

The HEK-293 hTLR transfectant assay employs HEK293 cells stably transfected with various hTLRs and transiently co-transfected with a plasmid containing an NF-κB driven secreted embryonic alkaline phosphate (SEAP) reporter gene. Stimulation of TLRs activates their downstream signaling pathways and induces nuclear translocation of the transcription factor NF-κB. Reporter gene activity is then measured using a spectrophotometric assay.

To measure agonist activity, human embryonic kidney (HEK) cells which stably express various human TLR genes, including TLR7 and TLR8, and a NFkB-luciferase reporter gene (e.g., 293XL-hTLR8 cells available from InvivoGen, San Diego, Calif.) are prepared according to supplier's instructions and incubated with various concentrations of test compound overnight. The amount of induced luciferase is measured by reading the absorbance at 650 mu. Agonist compounds of the invention have an $MC_{50}$ of 25 μM or less, wherein $MC_{50}$ is defined as the concentration at which 50% of maximum induction is seen.

Example 3

PBMC Assays for TLR7 and TLR8

Peripheral blood mononuclear cells (PBMCs) from human blood were isolated using BD Vacutainer Cell Preparation Tubes with sodium citrate. Cells were incubated with compound overnight. TLR8 activity was assayed by measuring the amount of TNFα in supernatants by ELISA. TLR7 activity was assayed by measuring the amount of IFNα in supernatants by ELISA (R&D Systems). Compounds of this invention had an $MC_{50}$ of 25,000 (nM) or less, wherein $MC_{50}$ is the concentration at which 50% of the maximum induction is seen. The results of this assay are shown below in Tables 2 and 3.

$MC_{50}$ numbers are represented as factors of ten, for example, + indicates an $MC_{50}$ value of X $10^4$, or a value in the tens of thousands of nanomolar (nM range); ++ indicates an $MC_{50}$ value of X $10^3$, or a value in the thousands; +++ indicates an $MC_{50}$ value of X $10^2$, or a value in the hundreds; and ++++ indicates an $MC_{50}$ value of X $10^1$ or $10^0$, or a value in the tens or ones.

TABLE 2

| Cmpd # | Structure | TLR8 MC$_{50}$ |
|---|---|---|
| 113 | 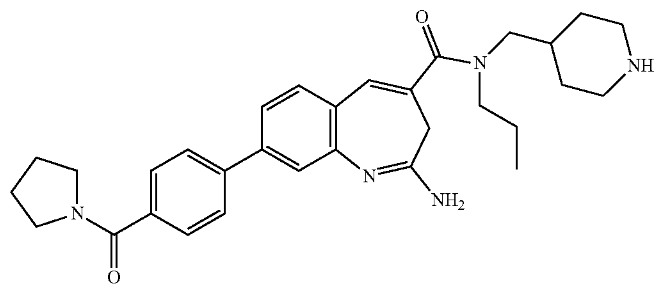 [SMILES: CCCN(CC1CCNCC1)C(=O)C1=Cc2ccc(-c3ccc(C(=O)N4CCCC4)cc3)cc2N=C(N)C1] | +++ |
| 175 | 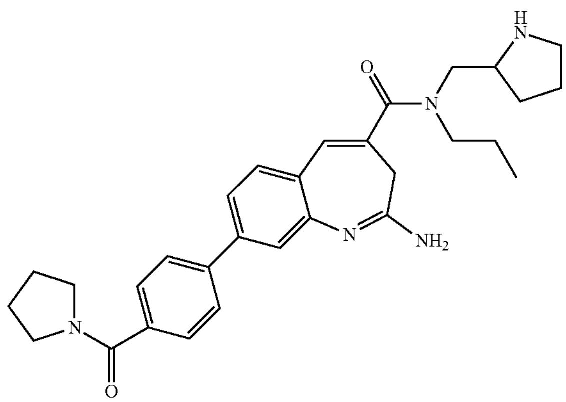 [SMILES: CCCN(CC1CCCN1)C(=O)C1=Cc2ccc(-c3ccc(C(=O)N4CCCC4)cc3)cc2N=C(N)C1] | ++ |
| 116 | 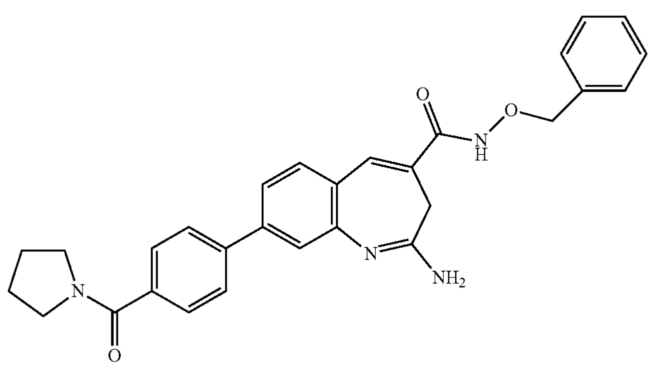 [SMILES: NC1=Nc2cc(-c3ccc(C(=O)N4CCCC4)cc3)ccc2C=C(C(=O)NOCc2ccccc2)C1] | ++ |
| 118 | 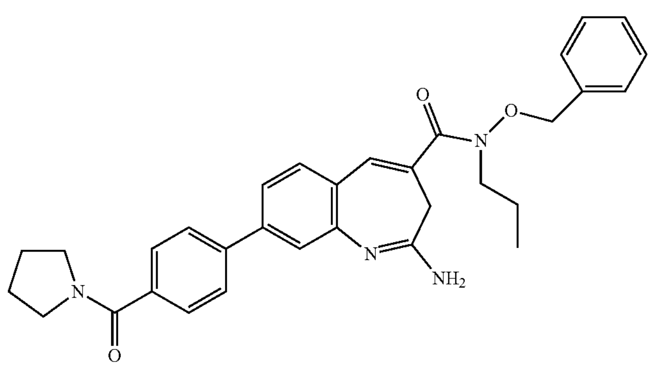 [SMILES: CCCN(OCc1ccccc1)C(=O)C1=Cc2ccc(-c3ccc(C(=O)N4CCCC4)cc3)cc2N=C(N)C1] | ++++ |

TABLE 2-continued

| Cmpd # | Structure | TLR8 MC$_{50}$ |
|---|---|---|
| 177 | 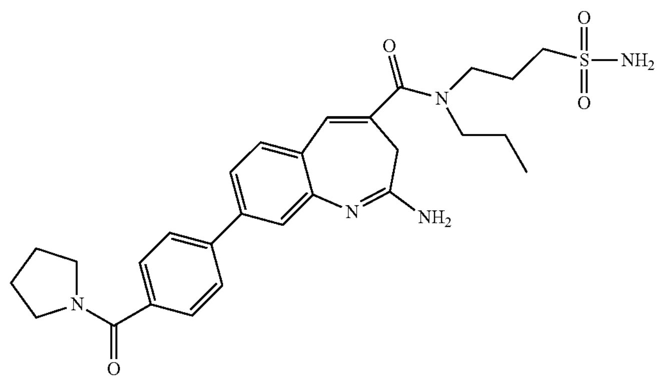 [SMILES: CCCN(CCCS(N)(=O)=O)C(=O)C1=Cc2ccc(-c3ccc(C(=O)N4CCCC4)cc3)cc2N=C(N)C1] | +++ |
| 148 | 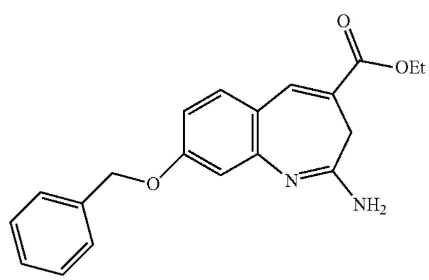 [SMILES: CCOC(=O)C1=Cc2ccc(OCc3ccccc3)cc2N=C(N)C1] | +++ |
| 185 | 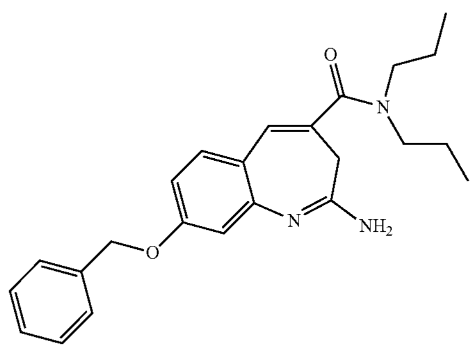 [SMILES: CCCN(CCC)C(=O)C1=Cc2ccc(OCc3ccccc3)cc2N=C(N)C1] | +++ |
| 196 | 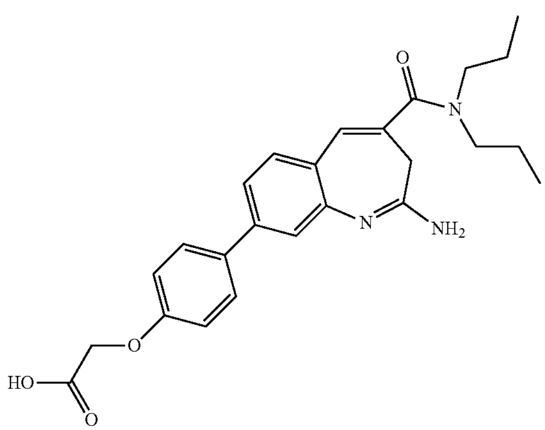 [SMILES: CCCN(CCC)C(=O)C1=Cc2ccc(-c3ccc(OCC(=O)O)cc3)cc2N=C(N)C1] | + |

TABLE 2-continued

| Cmpd # | Structure | TLR8 MC$_{50}$ |
|---|---|---|
| 197 | 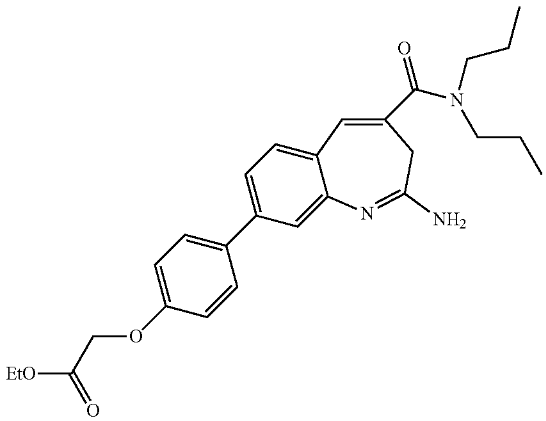 [SMILES: CCCN(CCC)C(=O)C1=Cc2ccc(-c3ccc(OCC(=O)OCC)cc3)cc2N=C(N)C1] | +++ |
| 184 | 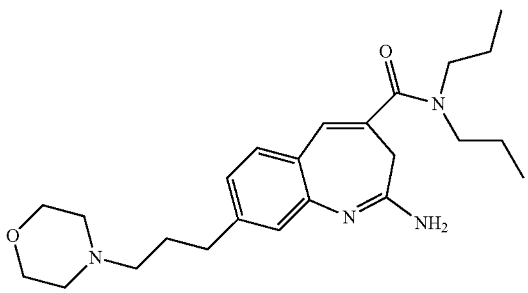 [SMILES: CCCN(CCC)C(=O)C1=Cc2ccc(CCCN3CCOCC3)cc2N=C(N)C1] | ++++ |
| 200 | 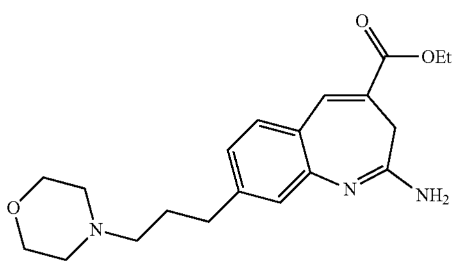 [SMILES: CCOC(=O)C1=Cc2ccc(CCCN3CCOCC3)cc2N=C(N)C1] | ++++ |
| 183 | 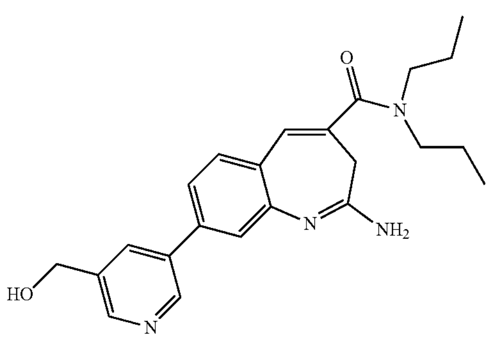 [SMILES: CCCN(CCC)C(=O)C1=Cc2ccc(-c3cncc(CO)c3)cc2N=C(N)C1] | ++++ |

TABLE 2-continued

| Cmpd # | Structure | TLR8 MC$_{50}$ |
|---|---|---|
| 191 | 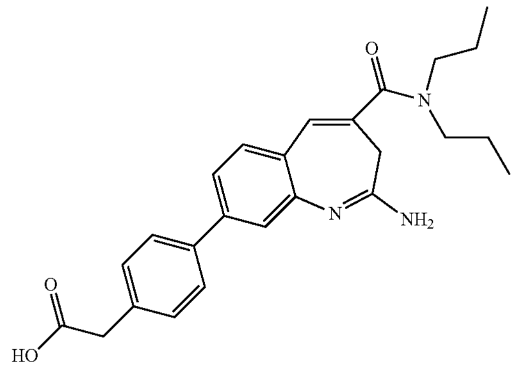 [SMILES: CCCN(CCC)C(=O)C1=Cc2ccc(-c3ccc(CC(=O)O)cc3)cc2N=C(N)C1] | ++ |
| 192 | 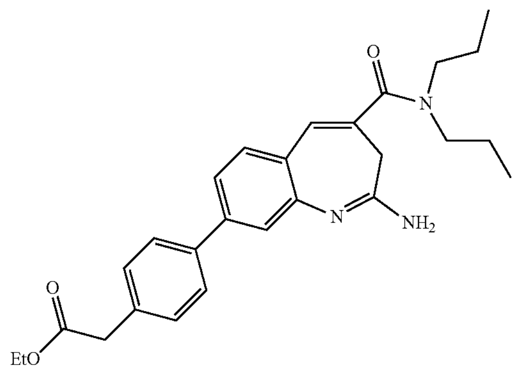 [SMILES: CCCN(CCC)C(=O)C1=Cc2ccc(-c3ccc(CC(=O)OCC)cc3)cc2N=C(N)C1] | +++ |
| 193 | 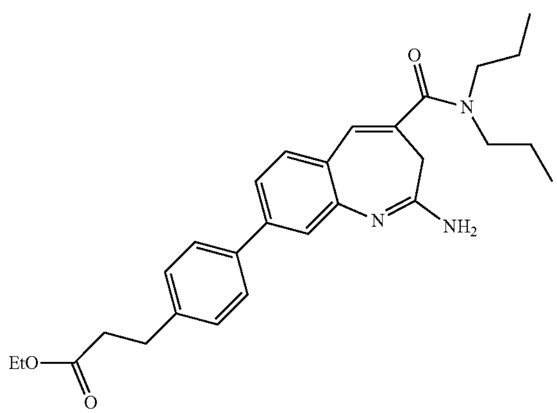 [SMILES: CCCN(CCC)C(=O)C1=Cc2ccc(-c3ccc(CCC(=O)OCC)cc3)cc2N=C(N)C1] | ++ |
| 198 | 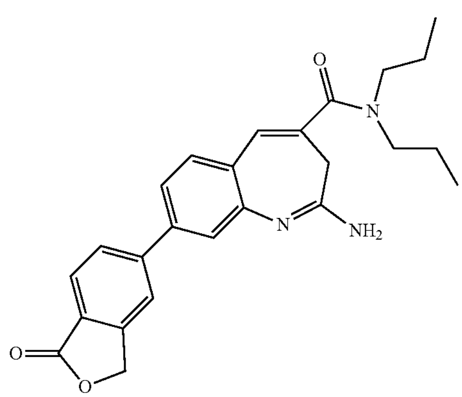 [SMILES: CCCN(CCC)C(=O)C1=Cc2ccc(-c3ccc4c(c3)COC4=O)cc2N=C(N)C1] | +++ |

TABLE 2-continued

| Cmpd # | Structure | TLR8 MC$_{50}$ |
|---|---|---|
| 199 | 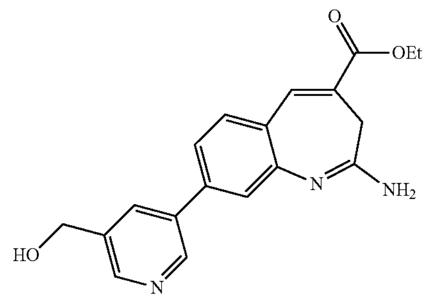 [SMILES: CCOC(=O)C1=Cc2ccc(-c3cncc(CO)c3)cc2N=C(N)C1] | ++++ |
| 201 | 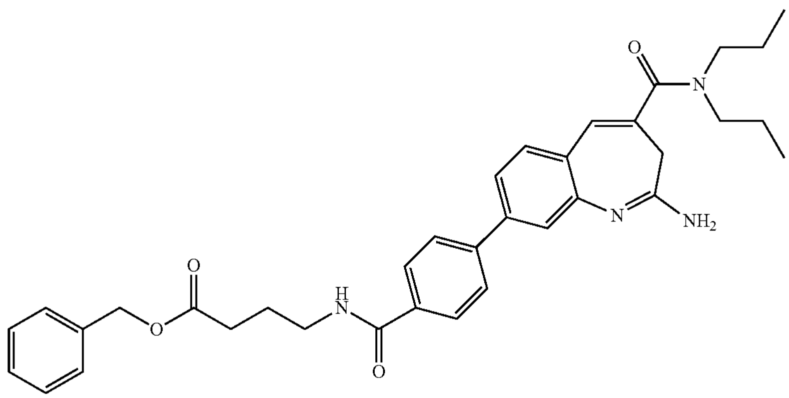 [SMILES: CCCN(CCC)C(=O)C1=Cc2ccc(-c3ccc(C(=O)NCCCC(=O)OCc4ccccc4)cc3)cc2N=C(N)C1] | +++ |
| 205 | 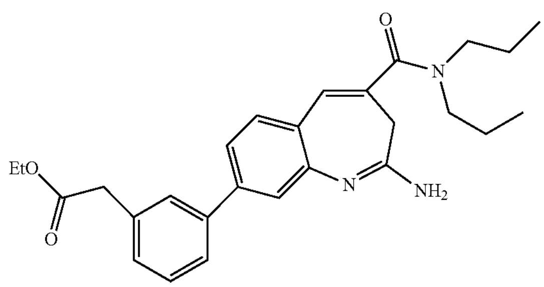 [SMILES: CCCN(CCC)C(=O)C1=Cc2ccc(-c3cccc(CC(=O)OCC)c3)cc2N=C(N)C1] | +++ |
| 213 | 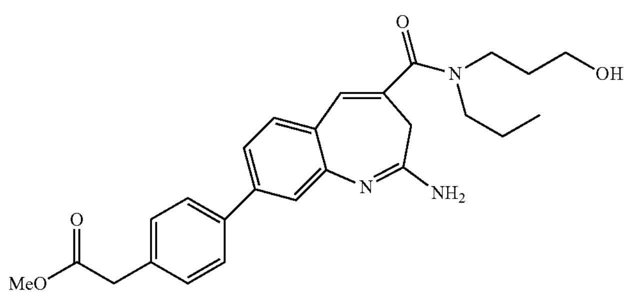 [SMILES: CCCN(CCCO)C(=O)C1=Cc2ccc(-c3ccc(CC(=O)OC)cc3)cc2N=C(N)C1] | +++ |
| 214 | 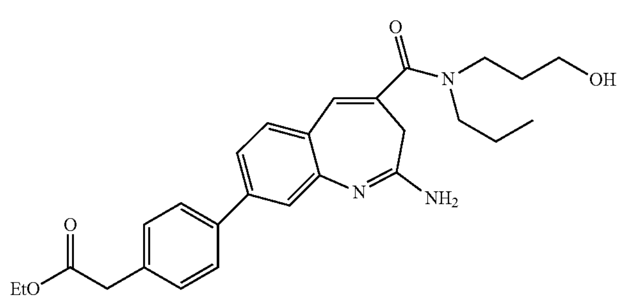 [SMILES: CCCN(CCCO)C(=O)C1=Cc2ccc(-c3ccc(CC(=O)OCC)cc3)cc2N=C(N)C1] | ++++ |

TABLE 2-continued

| Cmpd # | Structure | TLR8 MC$_{50}$ |
|---|---|---|
| 215 | benzazepine-2-amine with 4-carboxamide N-(3-hydroxypropyl)-N-propyl and 8-(4-(isopropoxycarbonylmethyl)phenyl) substituent | ++++ |
| 216 | benzazepine-2-amine with 4-carboxamide N-(3-hydroxypropyl)-N-propyl and 8-(4-(isobutoxycarbonylmethyl)phenyl) substituent | ++++ |
| 217 | benzazepine-2-amine with 4-carboxamide N-(3-hydroxypropyl)-N-propyl and 8-(4-(cyclopropylmethoxycarbonylmethyl)phenyl) substituent | ++++ |
| 218 | benzazepine-2-amine with 4-carboxamide N-(3-hydroxypropyl)-N-propyl and 8-(4-(benzyloxycarbonylmethyl)phenyl) substituent | +++ |
| 219 | benzazepine-2-amine with 4-carboxamide N-(3-hydroxypropyl)-N-propyl and 8-(4-(3-isobutoxy-3-oxopropyl)phenyl) substituent | ++ |

TABLE 2-continued

| Cmpd # | Structure | TLR8 MC$_{50}$ |
|---|---|---|
| 221 | 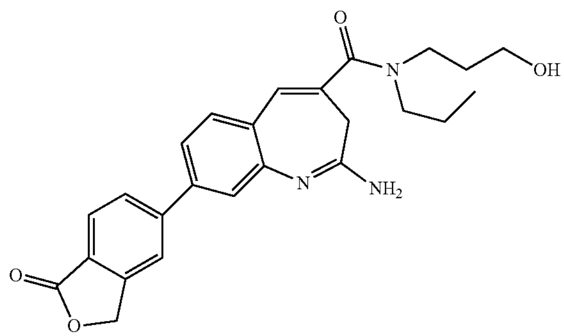 [SMILES: CCCN(CCCO)C(=O)C1=Cc2ccc(-c3ccc4c(c3)COC4=O)cc2N=C(N)C1] | +++ |
| 222 | 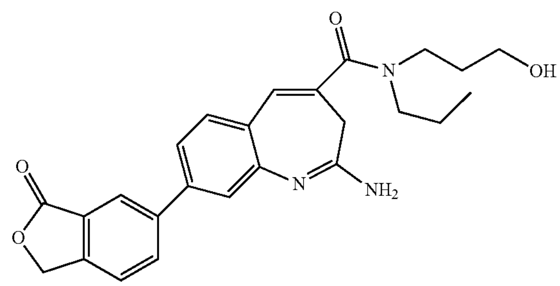 [SMILES: CCCN(CCCO)C(=O)C1=Cc2ccc(-c3ccc4c(c3)C(=O)OC4)cc2N=C(N)C1] | ++++ |
| 223 | 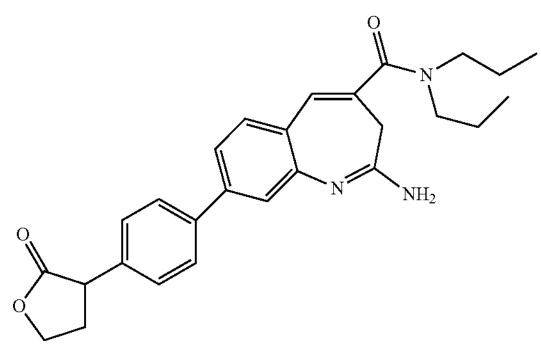 [SMILES: CCCN(CCC)C(=O)C1=Cc2ccc(-c3ccc(C4CCOC4=O)cc3)cc2N=C(N)C1] | +++ |
| 224 | 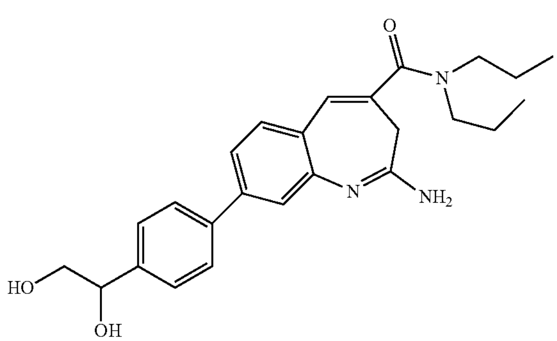 [SMILES: CCCN(CCC)C(=O)C1=Cc2ccc(-c3ccc(C(O)CO)cc3)cc2N=C(N)C1] | +++ |

TABLE 2-continued

| Cmpd # | Structure | TLR8 MC$_{50}$ |
|---|---|---|
| 226 | (structure) | +++ |
| 225 | (structure) | +++ |

TABLE 3

| Cmpd # | Structure | TLR7 MC$_{50}$ |
|---|---|---|
| 116 | (structure) | + |

TABLE 3-continued

| Cmpd # | Structure | TLR7 MC$_{50}$ |
|---|---|---|
| 197 | (structure: 2-amino-N,N-dipropyl-8-[4-(ethoxycarbonylmethoxy)phenyl]-3H-benzo[b]azepine-4-carboxamide) | ++ |
| 184 | (structure: 2-amino-N,N-dipropyl-8-[3-(morpholin-4-yl)propyl]-3H-benzo[b]azepine-4-carboxamide) | ++ |
| 183 | (structure: 2-amino-N,N-dipropyl-8-[5-(hydroxymethyl)pyridin-3-yl]-3H-benzo[b]azepine-4-carboxamide) | ++ |
| 191 | (structure: 2-amino-N,N-dipropyl-8-[4-(carboxymethyl)phenyl]-3H-benzo[b]azepine-4-carboxamide) | + |

TABLE 3-continued

| Cmpd # | Structure | TLR7 MC$_{50}$ |
|---|---|---|
| 192 | 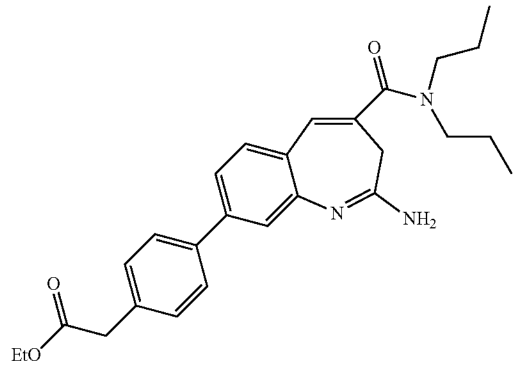 [SMILES: CCCN(CCC)C(=O)C1=Cc2ccc(-c3ccc(CC(=O)OCC)cc3)cc2N=C(N)C1] | + |
| 193 | 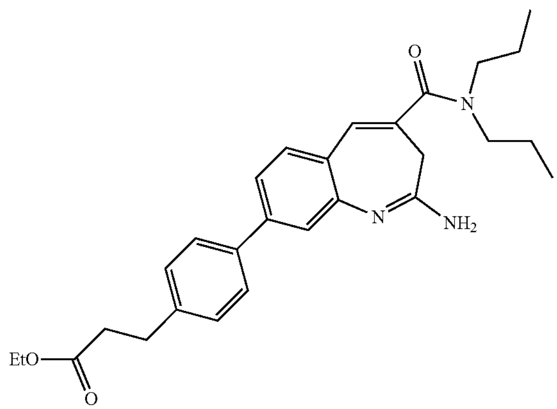 [SMILES: CCCN(CCC)C(=O)C1=Cc2ccc(-c3ccc(CCC(=O)OCC)cc3)cc2N=C(N)C1] | ++ |
| 199 | 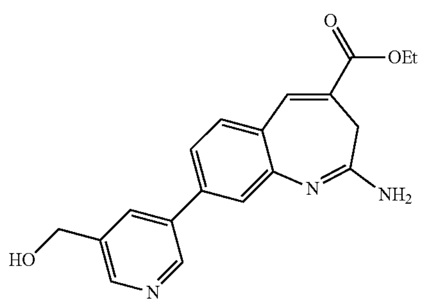 [SMILES: CCOC(=O)C1=Cc2ccc(-c3cncc(CO)c3)cc2N=C(N)C1] | ++ |
| 213 | 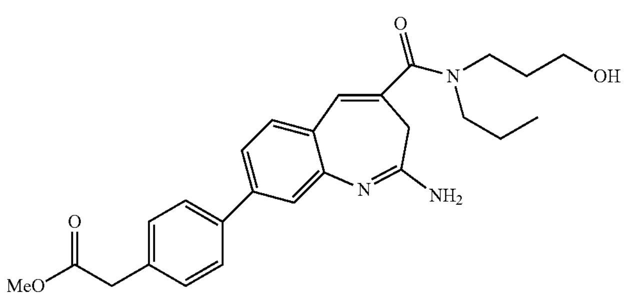 [SMILES: CCCN(CCCO)C(=O)C1=Cc2ccc(-c3ccc(CC(=O)OC)cc3)cc2N=C(N)C1] | ++ |

TABLE 3-continued
| Cmpd # | Structure | TLR7 MC$_{50}$ |
|---|---|---|
| 214 | 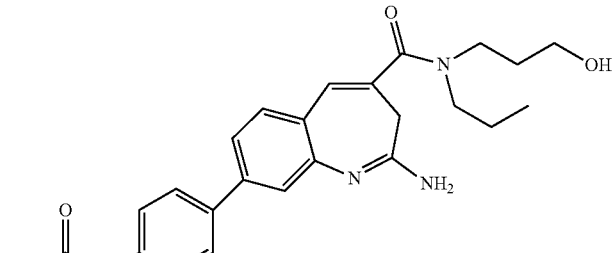 | ++ |
| 215 | 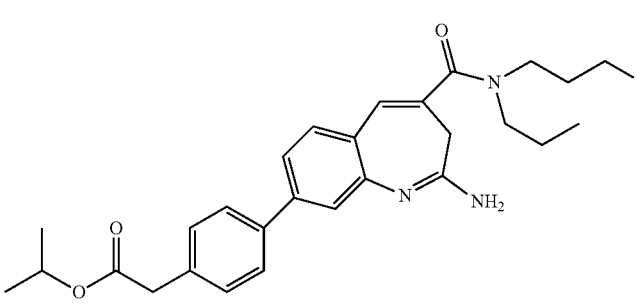 | + |
| 216 | 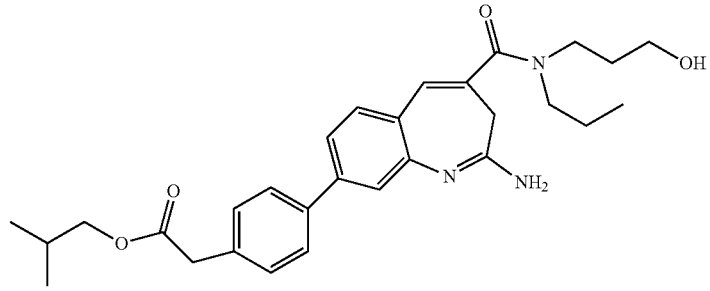 [SMILES: CCCN(CCCO)C(=O)C1=Cc2ccc(-c3ccc(CC(=O)OCC(C)C)cc3)cc2N=C(N)C1] | + |
| 219 | 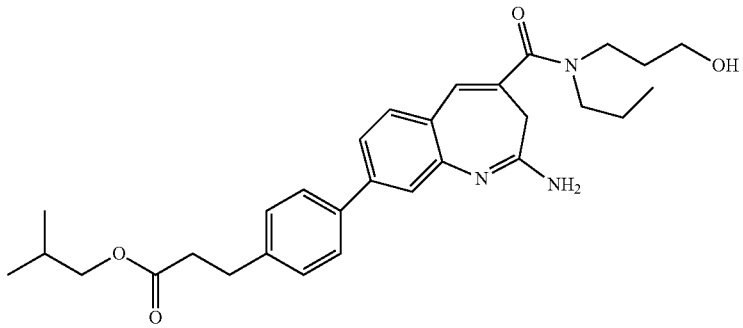 [SMILES: CCCN(CCCO)C(=O)C1=Cc2ccc(-c3ccc(CCC(=O)OCC(C)C)cc3)cc2N=C(N)C1] | ++ |
| 222 | 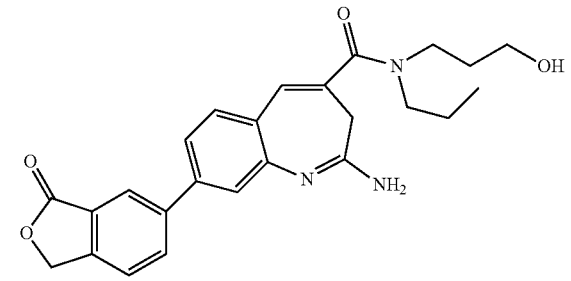 [SMILES: CCCN(CCCO)C(=O)C1=Cc2ccc(-c3ccc4c(c3)C(=O)OC4)cc2N=C(N)C1] | +++ |

TABLE 3-continued

| Cmpd # | Structure | TLR7 MC$_{50}$ |
|---|---|---|
| 223 | 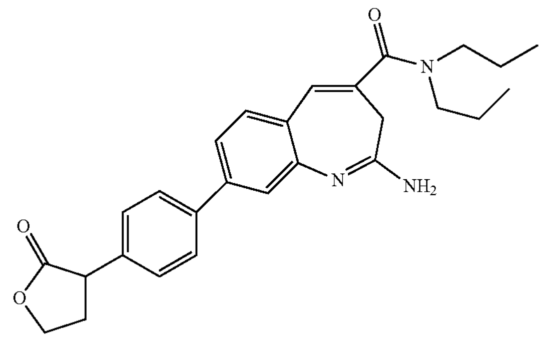 [SMILES: CCCN(CCC)C(=O)C1=Cc2ccc(-c3ccc(C4CCOC4=O)cc3)cc2N=C(N)C1] | ++ |
| 224 | 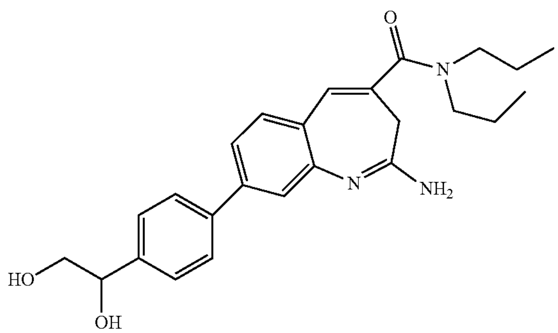 [SMILES: CCCN(CCC)C(=O)C1=Cc2ccc(-c3ccc(C(O)CO)cc3)cc2N=C(N)C1] | + |
| 225 | 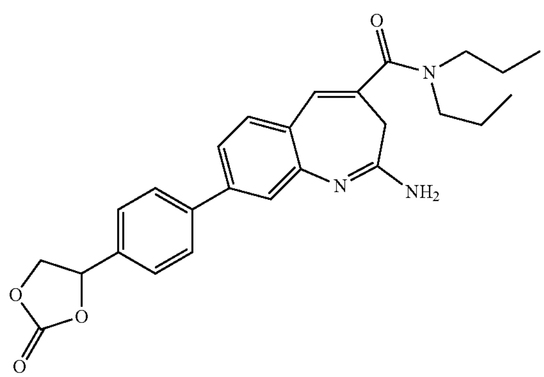 [SMILES: CCCN(CCC)C(=O)C1=Cc2ccc(-c3ccc(C4COC(=O)O4)cc3)cc2N=C(N)C1] | + |

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

Unless otherwise noted, all references listed herein are specifically incorporated by reference.

What is claimed is:

1. A method of treating oral cancer comprising administering to a subject suffering from oral cancer an effective amount of a compound having the formula I:

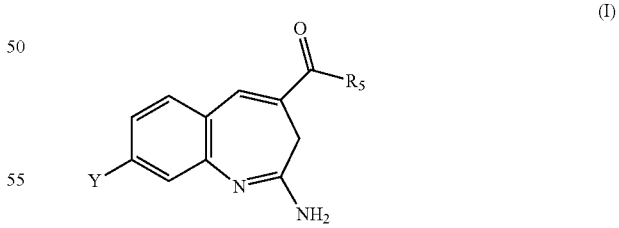

or a tautomer, enantiomer or salt thereof, wherein:

Y is —(O)$_x$(CH$_2$)$_y$R$^{11}$;

x is selected from 0 and 1;

y is selected from 0, 1, 2, and 3;

R$^{11}$ is selected from aryl, heteroaryl, and saturated or partially saturated heterocycle, wherein when x is 0, said aryl or heteroaryl is substituted with —C(O)NR$^1$R$^2$ or T;

$R^1$ and $R^2$ are independently selected from hydrogen and alkyl, wherein said alkyl is optionally substituted with —C(O)O(CH$_2$)$_r$R$^{12}$ or $R^1$ and $R^2$ together with the nitrogen atom to which they are attached form a saturated heterocyclic ring;

t is selected from 0, 1, 2, and 3;

$R^{12}$ is selected from cycloalkyl and aryl;

T is selected from heterocycle, —(CHR$^7$)$_z$OR$^9$, —(O)$_u$(CH$_2$)$_s$C(O)R$^8$, —OSO$_2$R$^{13}$, and —CH(OH)CH$_2$OH;

$R^7$ is H or —OH;

$R^8$ is selected from —OR$^{10}$ and alkyl;

$R^9$ is selected from alkyl and H;

$R^{10}$ is selected from alkyl, —(CH$_2$)R$^{12}$, and hydrogen, wherein said alkyl is optionally substituted with halogen, amine, alkylamine, or dialkylamine;

$R^{13}$ is selected from —OH, alkyl, CF$_3$, cycloalkyl, heterocycle, aryl, and heteroaryl;

u is selected from 0 and 1;

z is selected from 1, 2, and 3;

s is selected from 1 and 2;

$R^5$ is selected from —NR$^3$R$^4$ and —OR$^{10}$;

$R^3$ and $R^4$ are independently selected from H, alkyl, and —(O)$_q$(CH$_2$)$_r$P; wherein said alkyl is optionally substituted with one or more —OH;

q is selected from 0 and 1;

r is selected from 0, 1, 2, and 3;

P is selected from aryl, —SO$_2$R$^6$, and heterocycle; and $R^6$ is selected from —NH$_2$, —NH(alkyl), and —N(alkyl)$_2$, provided that when $R^{11}$ is aryl or heteroaryl, then
a) x+y≥1; or
b) $R^{11}$ is substituted with T; or
c) $R^5$ is NR$^3$R$^4$ and at least one of $R^3$ or $R^4$ is —(O)$_q$(CH$_2$)$_r$P and q+r≥1; or
d) at least one of $R^1$ or $R^2$ is alkyl substituted with —C(O)O(CH$_2$)$_r$R$^{12}$.

2. The method according to claim 1, wherein the compound is of formula II, III, IV or V:

(II)

wherein W is selected from N, C-T and CH;

(III)

provided that when $R^{11}$ is aryl or heteroaryl, then x+y≥1;

(IV)

wherein q+r≥1; or (V)

wherein at least one of $R^1$ or $R^2$ is alkyl substituted with —C(O)O(CH$_2$)$_r$R$^{12}$;

or a tautomer, enantiomer or salt thereof.

3. The method according to claim 1, wherein the compound is of formula VI:

(VI)

or a tautomer, enantiomer or salt thereof, wherein:

$R^{11}$ is selected from aryl and saturated or partially saturated heterocycle, wherein said aryl is substituted with T;

T is selected from heterocycle, —(O)$_u$(CH$_2$)$_s$C(O)R$^8$, and —CH(OH)CH$_2$OH;

$R^8$ is selected from —OR$^{10}$ and alkyl;

$R^{10}$ is selected from alkyl, —(CH$_2$)R$^{12}$, and hydrogen, wherein said alkyl is optionally substituted with halogen, amine, alkylamine, or dialkylamine;

$R^{12}$ is selected from cycloalkyl and aryl;

u is selected from 0 and 1;

s is selected from 1 and 2; and $R^3$ and $R^4$ are independently alkyl; wherein said alkyl is optionally substituted with one or more —OH.

4. The method according to claim 3, wherein:

$R^{11}$ is aryl substituted with T;

T is selected from —(O)$_u$(CH$_2$)$_s$C(O)R$^8$, and —CH(OH)CH$_2$OH;

$R^8$ is selected from —OR$^{10}$ and alkyl;

$R^{10}$ is selected from alkyl, —(CH$_2$)R$^{12}$, and hydrogen, wherein said alkyl is optionally substituted with halogen, amine, alkylamine, or dialkylamine;

$R^{12}$ is selected from cycloalkyl and aryl;
u is selected from 0 and 1;
s is selected from 1 and 2; and
$R^3$ and $R^4$ are independently alkyl; wherein said alkyl is optionally substituted with one or more —OH.

5. A method of treating oral cancer, comprising administering to a subject suffering from oral cancer an effective amount of a compound selected from the group consisting of:

113
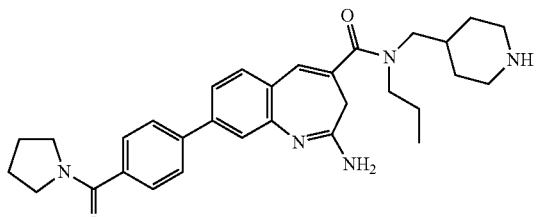

116
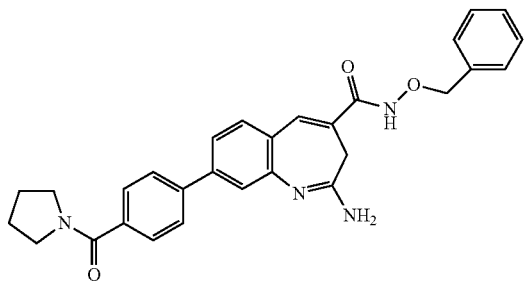

148
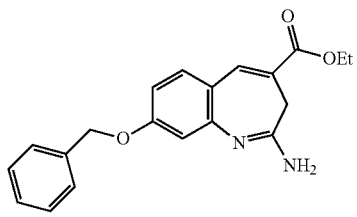

118
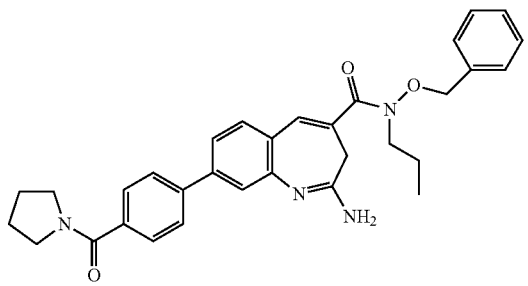

175
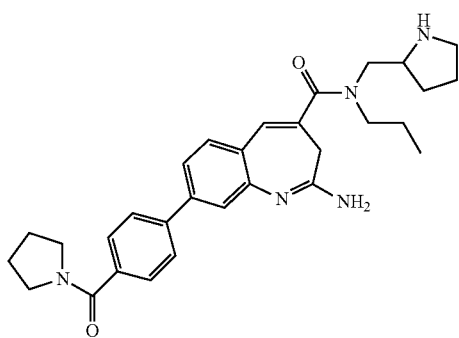

177
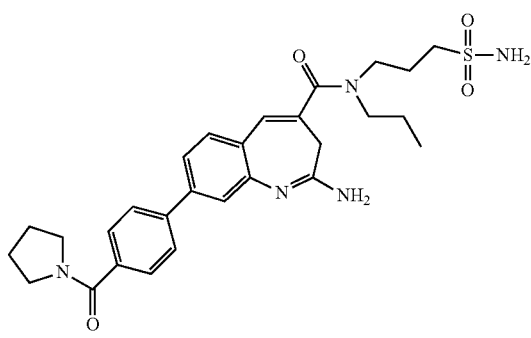

183
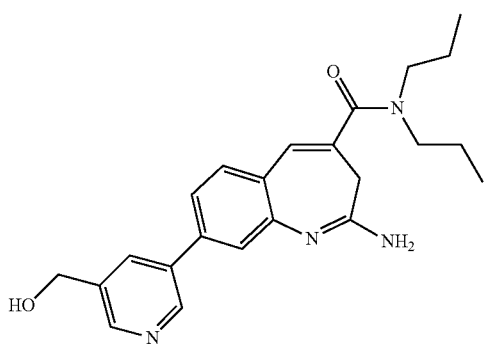

184
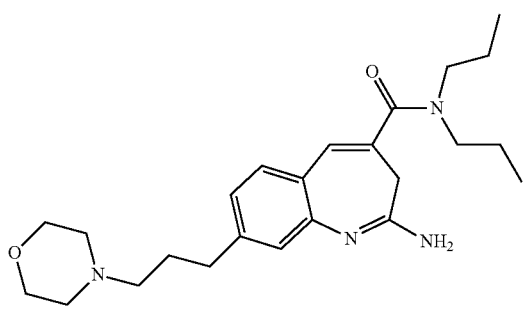

185
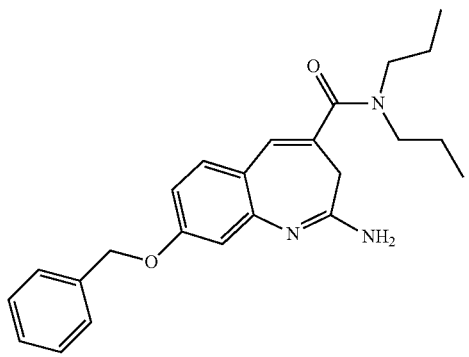
225
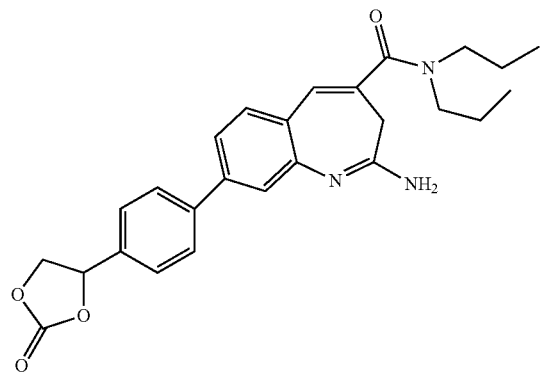
191
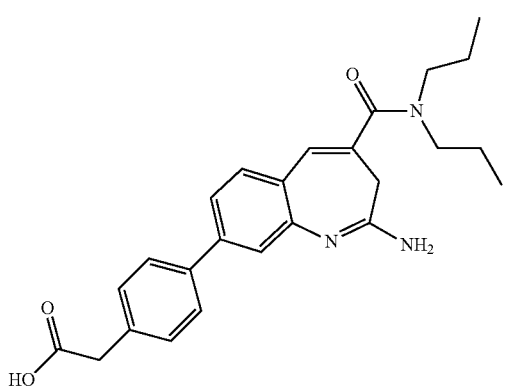
192
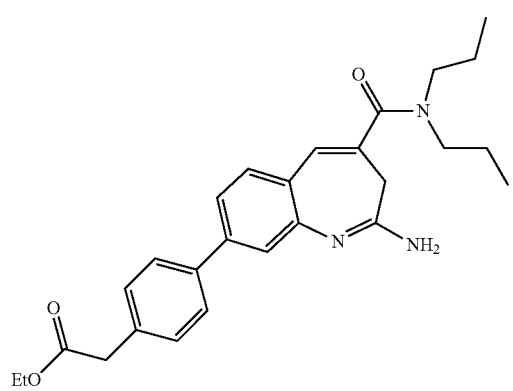
193
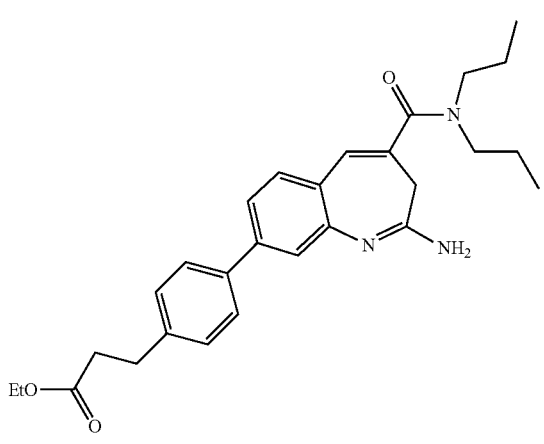
196
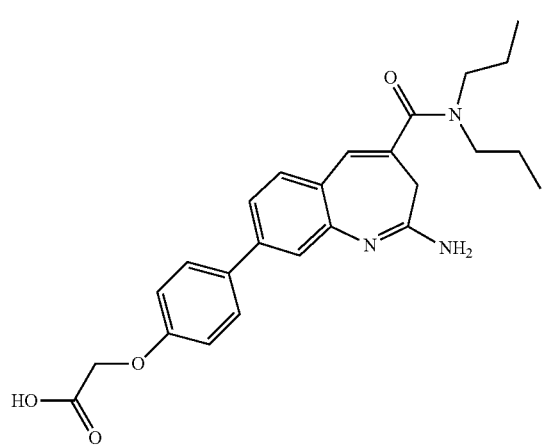

-continued
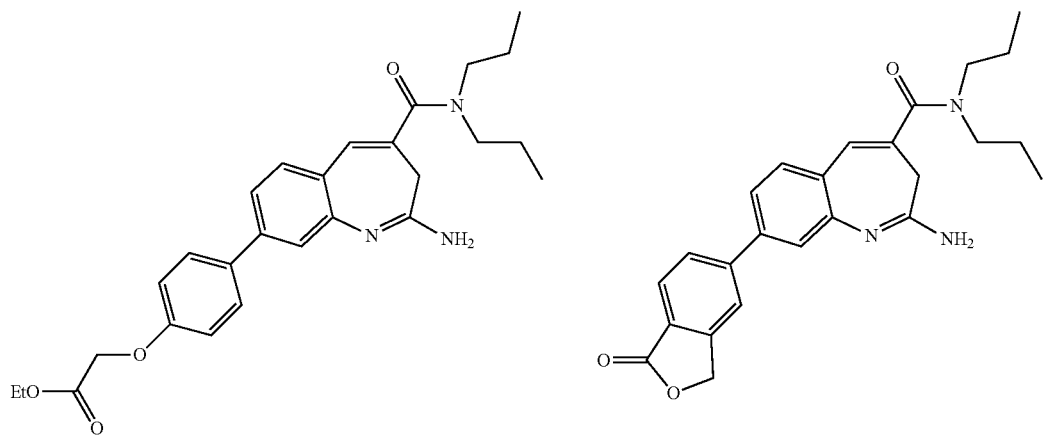
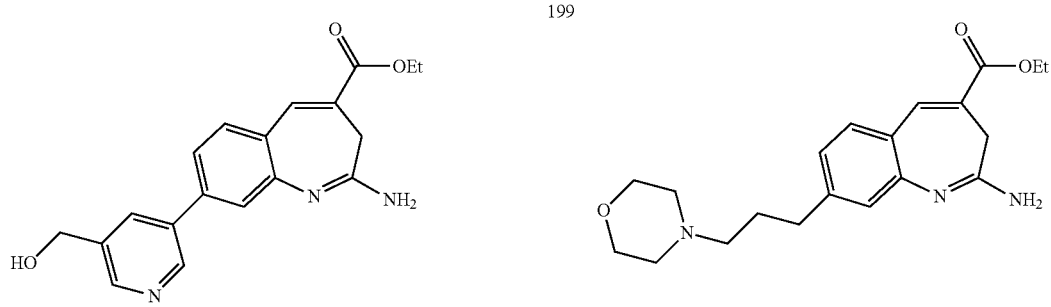
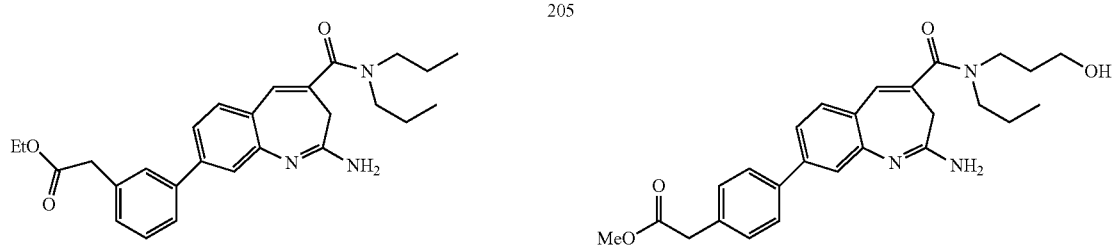
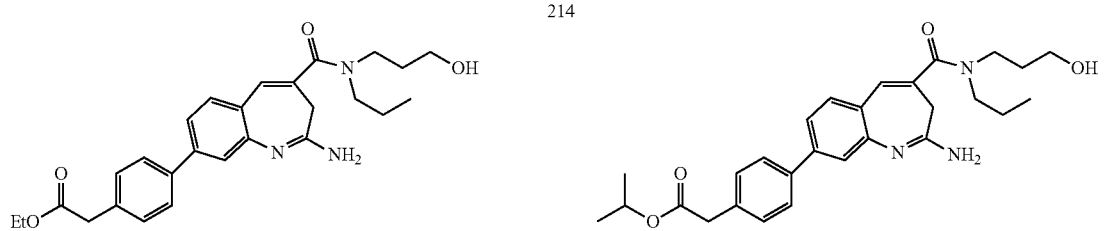
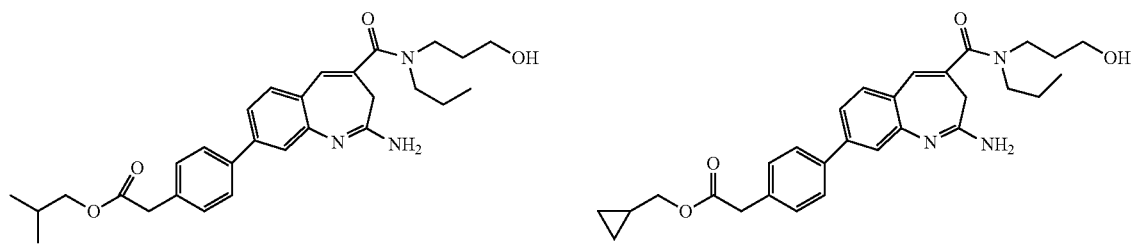

-continued
218 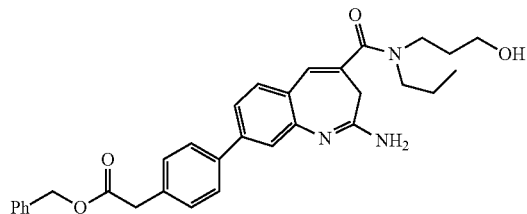
219 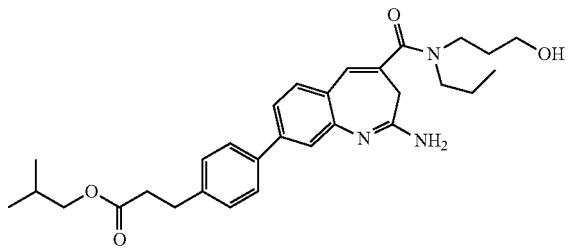
221 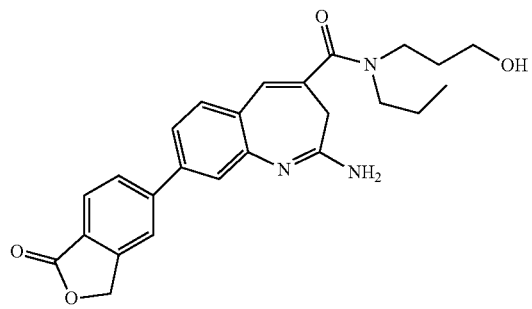
222 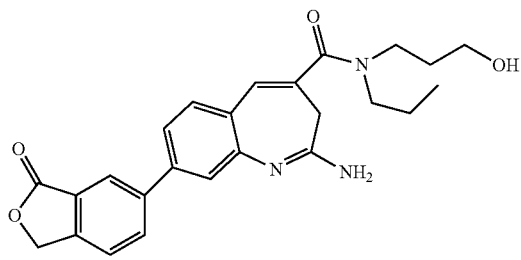
223 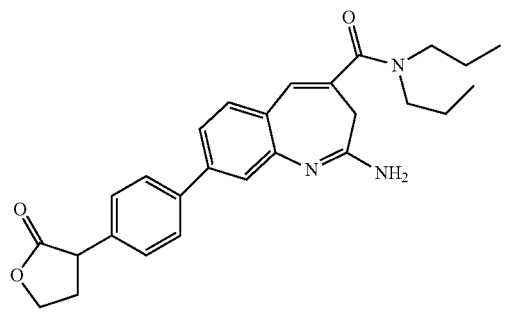
224 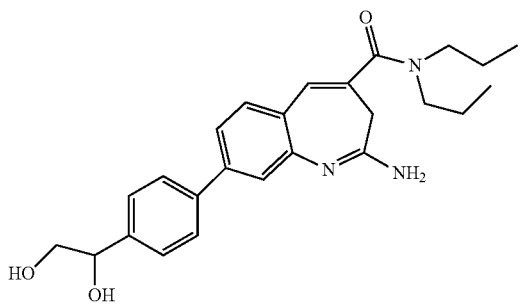
226 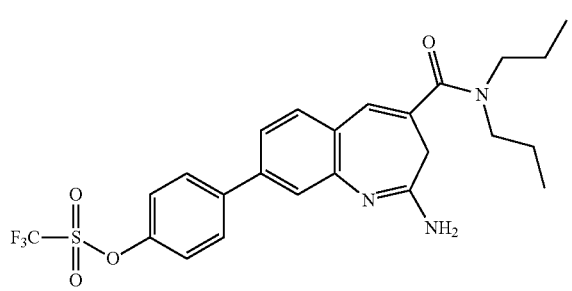
201 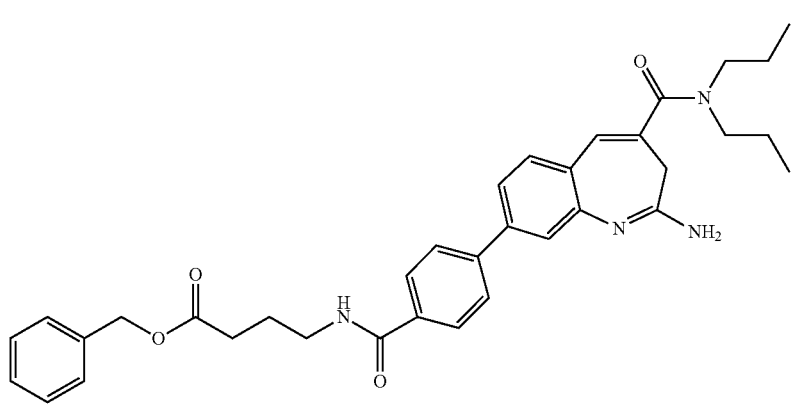

-continued
227
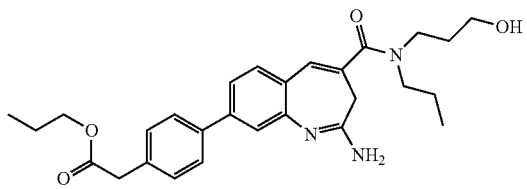
228
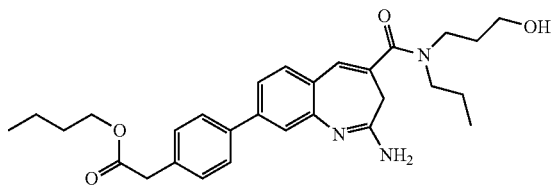
229
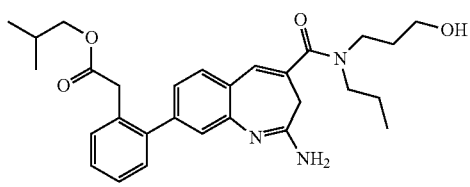
230
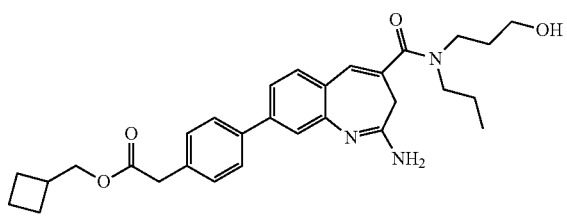
231
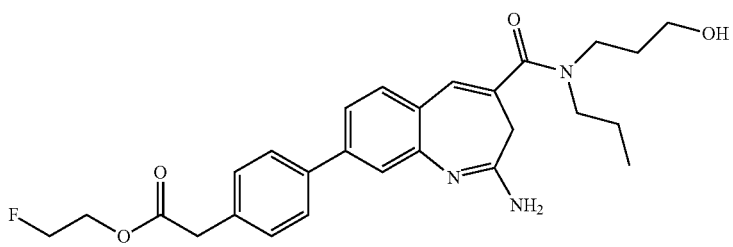
232
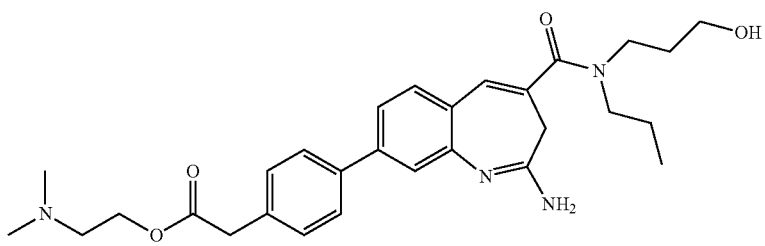
233
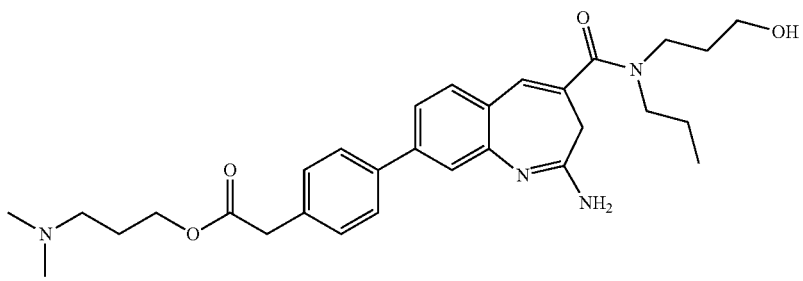
234
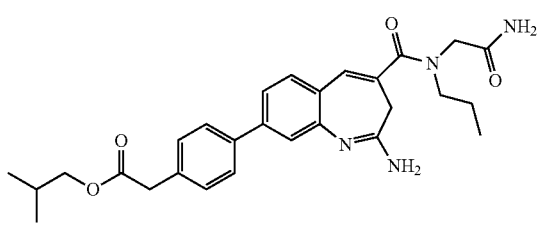
235
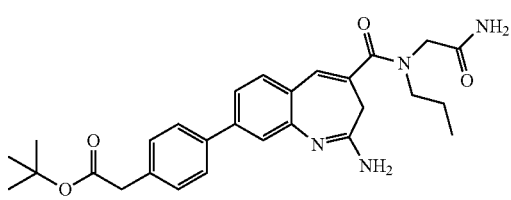

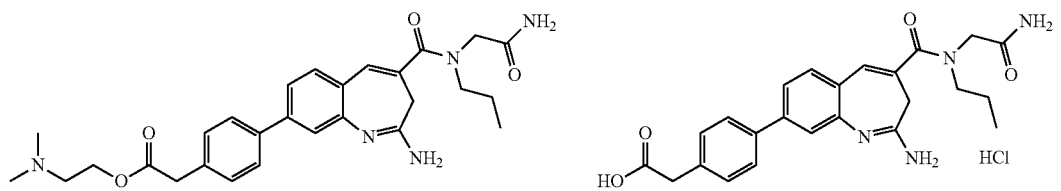
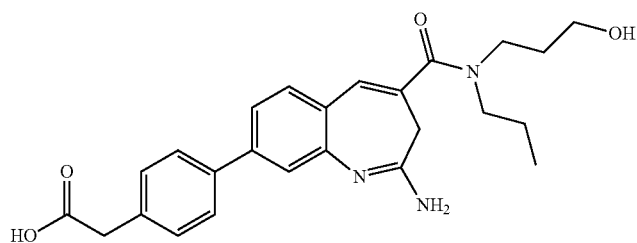
and tautomers, enantiomers and salts thereof.
6. The method according to claim 5, wherein the compound is selected from the group consisting of:
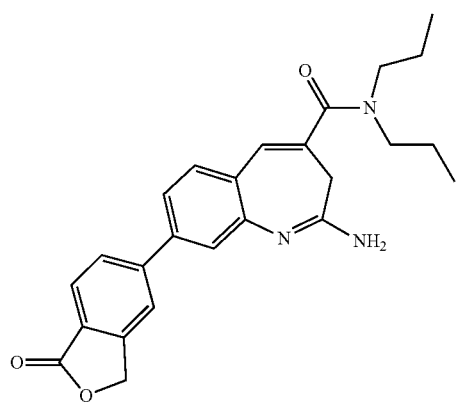
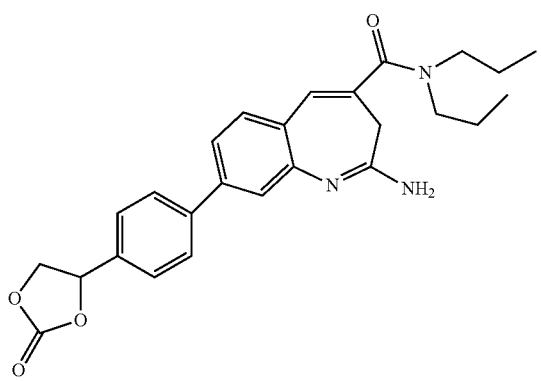
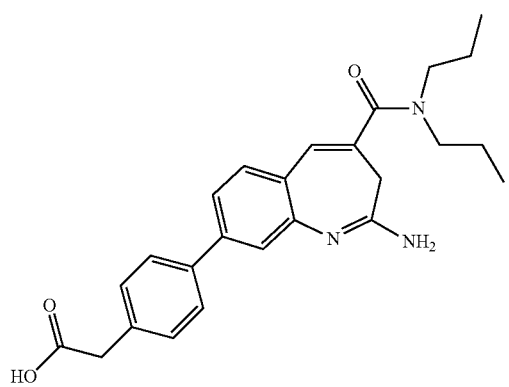
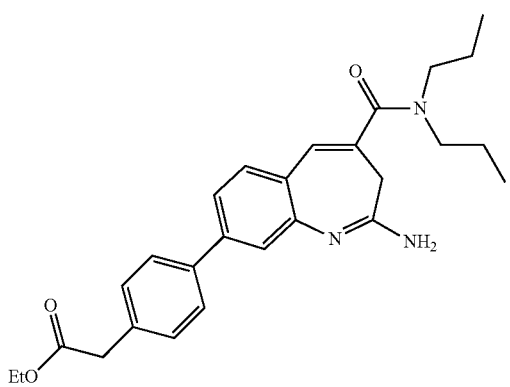

-continued
147
193
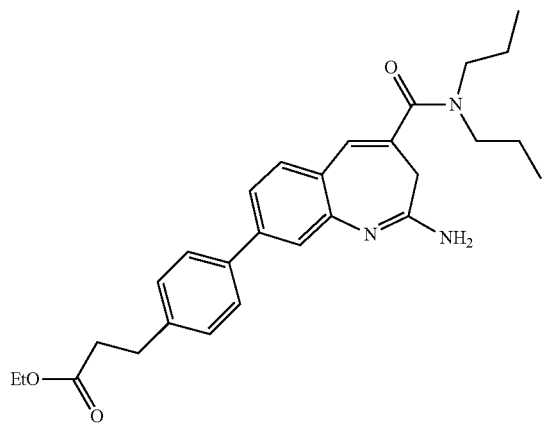
148
196
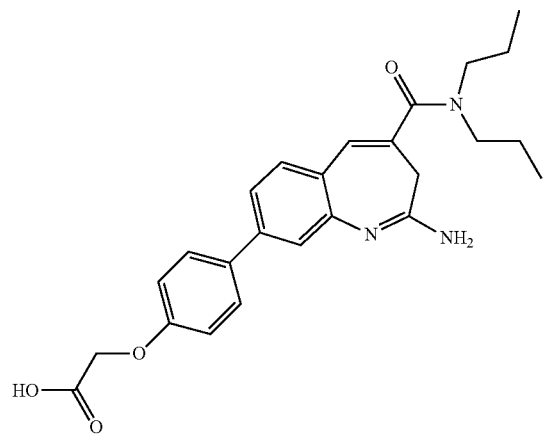
197
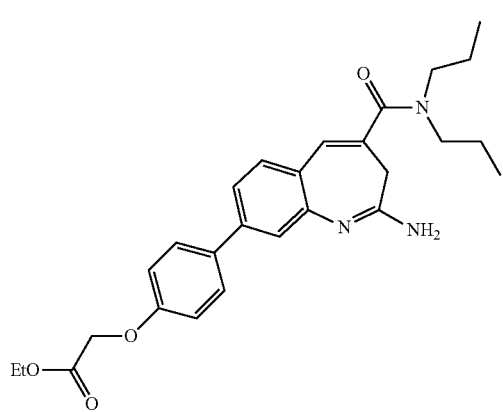
221
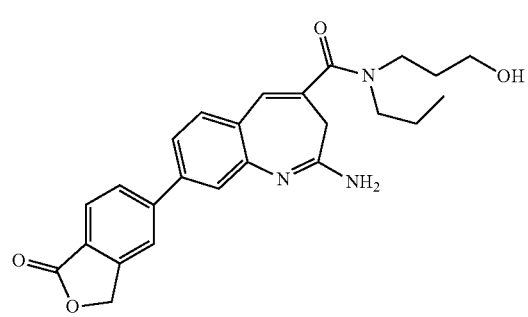
205
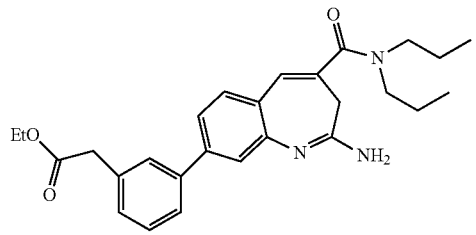
213
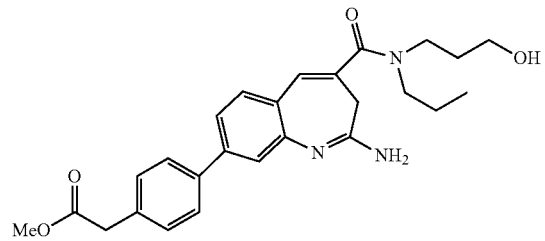
214
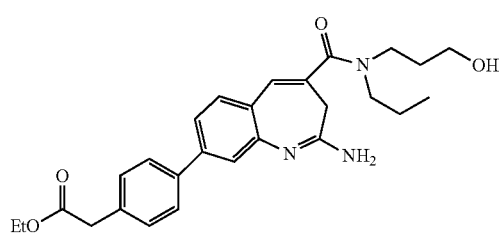
215
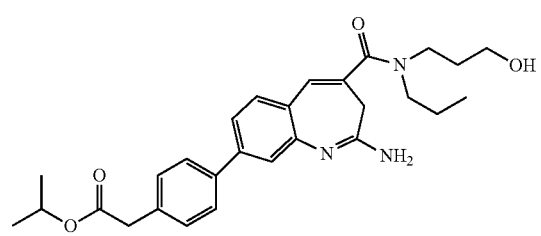
216
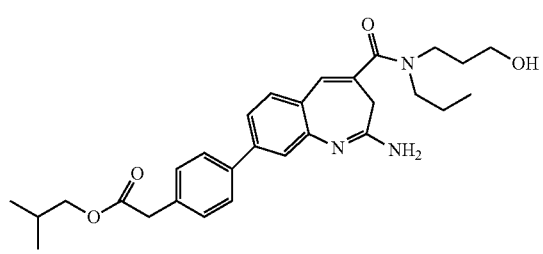
217
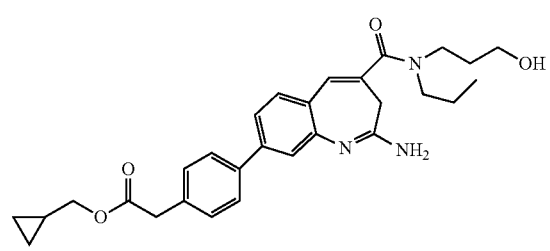

218
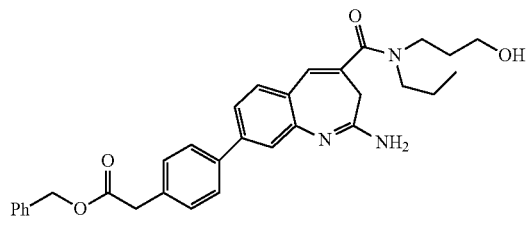
219
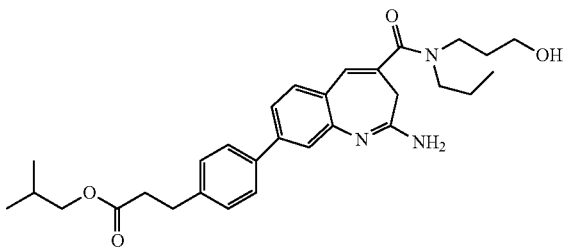
223
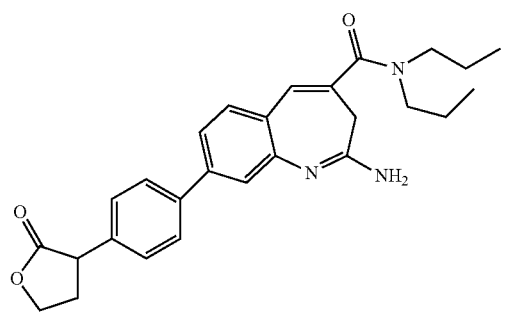
224
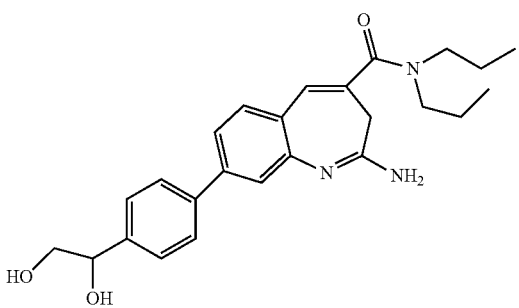
222
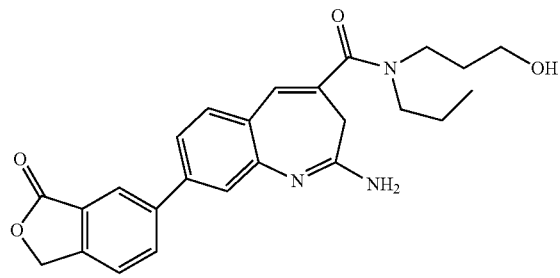
and tautomers, enantiomers and salts thereof.
7. The method according to claim 5, wherein the compound is selected from the group consisting of:
198
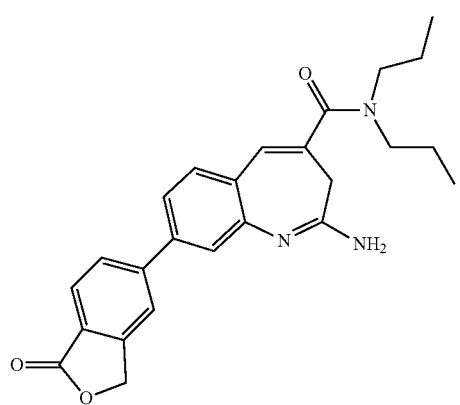
225
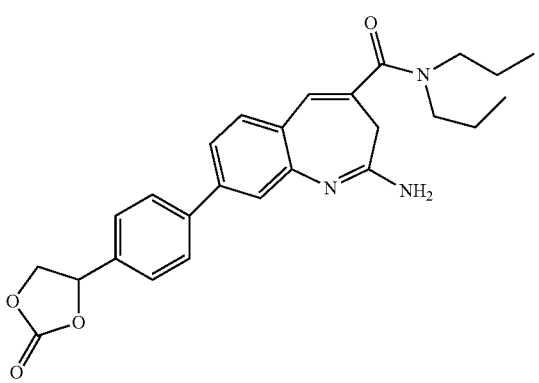

-continued
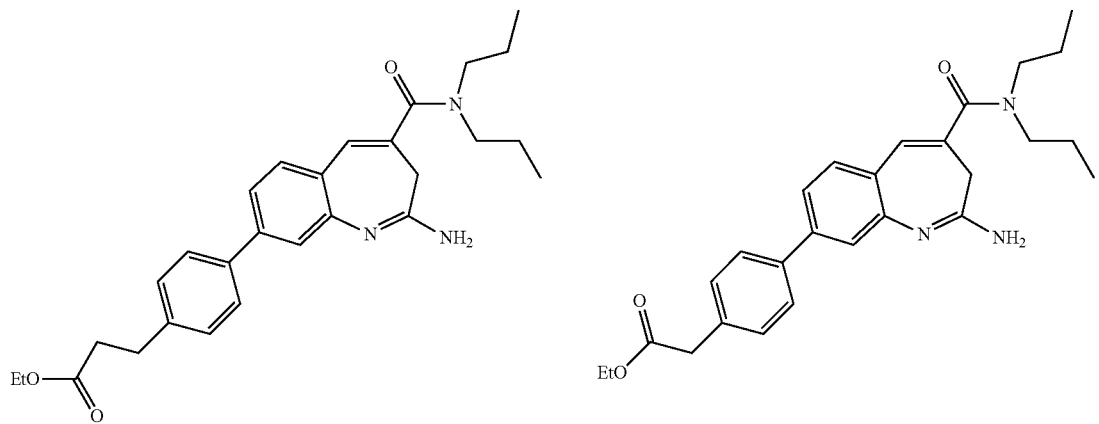
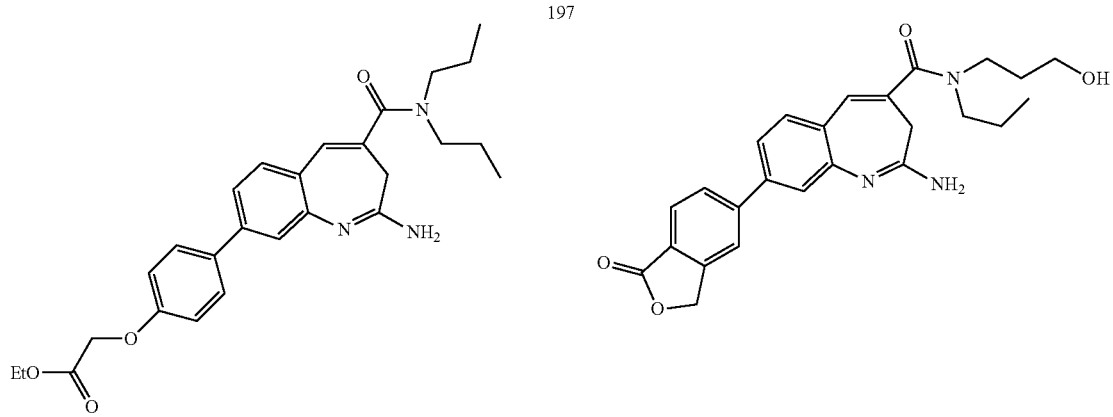
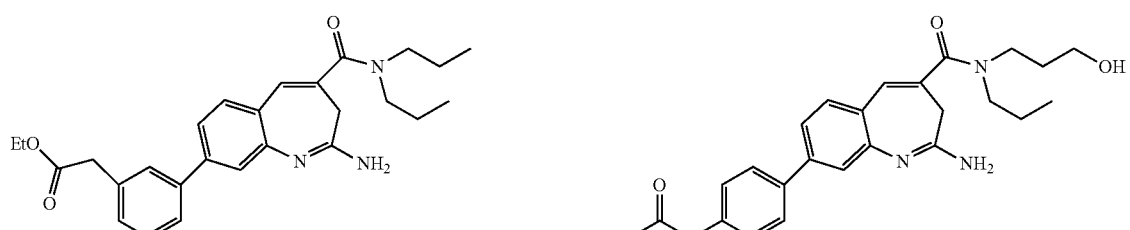
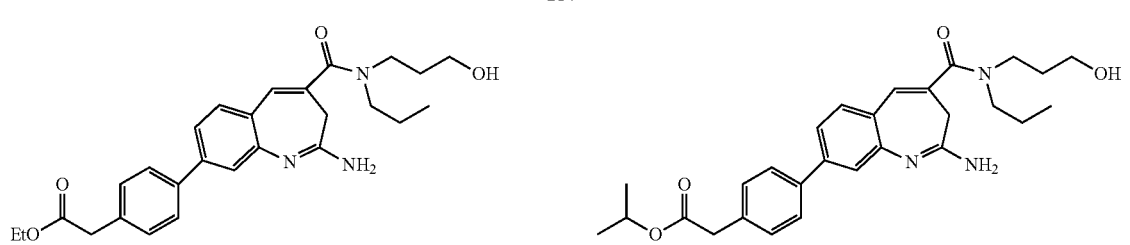
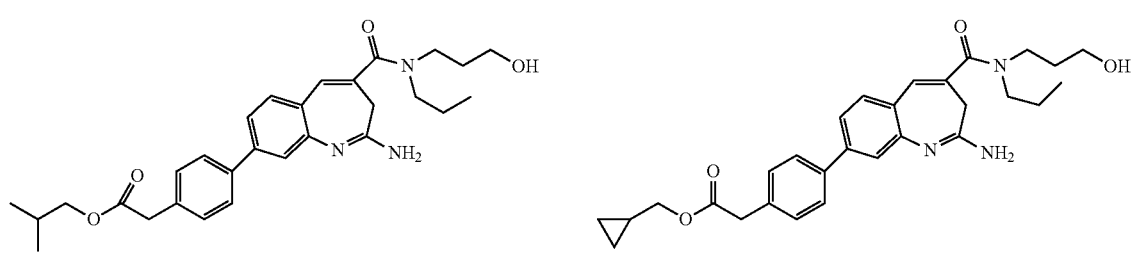

-continued
218 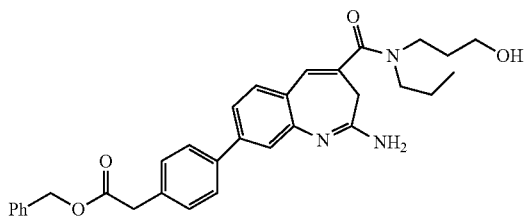
219 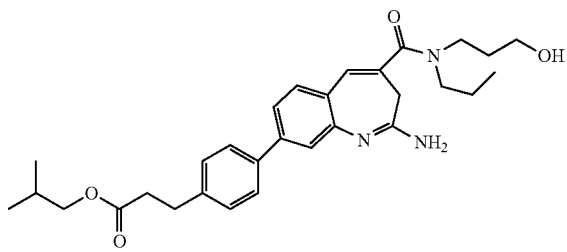
223 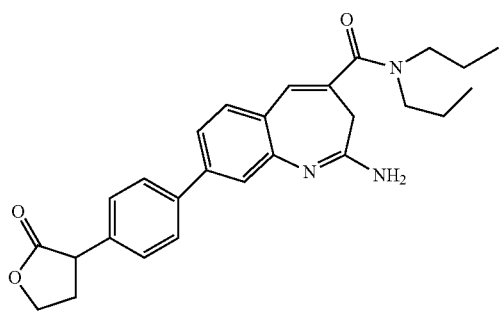
222 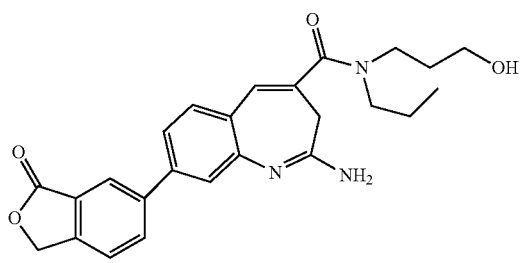
and tautomers, enantiomers and salts thereof.
8. The method according to claim 5, wherein the compound is selected from the group consisting of:
-continued
196 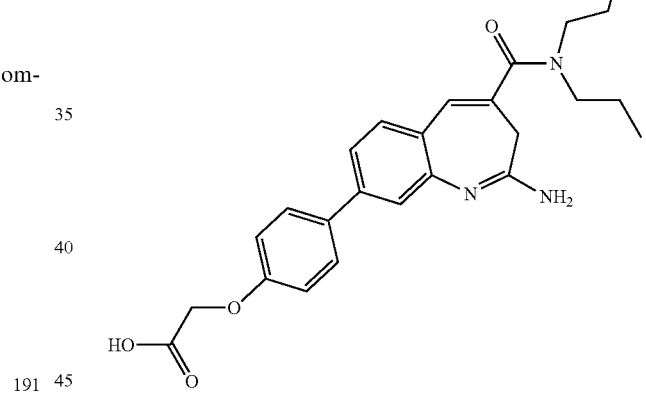
191 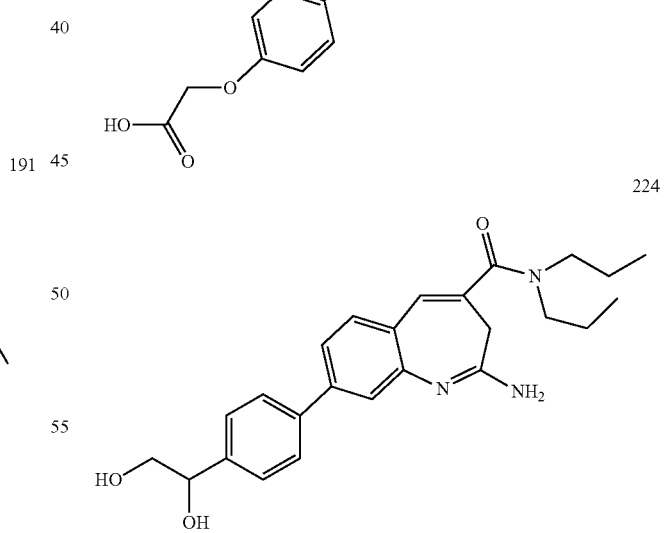
224 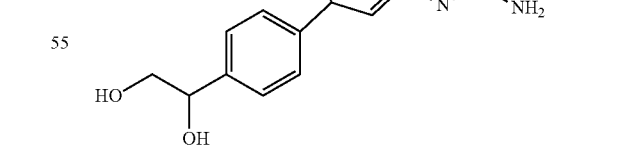
and tautomers, enantiomers and salts thereof.
* * * * *